US011896618B2

(12) United States Patent
Schreiber et al.

(10) Patent No.: US 11,896,618 B2
(45) Date of Patent: Feb. 13, 2024

(54) FLT3L-BASED CHIMERIC PROTEINS

(71) Applicant: Shattuck Labs, Inc., Austin, TX (US)

(72) Inventors: Taylor Schreiber, Austin, TX (US); George Fromm, Austin, TX (US); Suresh De Silva, Austin, TX (US)

(73) Assignee: Shattuck Labs, Inc., Austin, TX (US)

( * ) Notice: Subject to any disclaimer, the term of this patent is extended or adjusted under 35 U.S.C. 154(b) by 459 days.

(21) Appl. No.: 16/992,511

(22) Filed: Aug. 13, 2020

(65) Prior Publication Data

US 2021/0046116 A1  Feb. 18, 2021

Related U.S. Application Data

(63) Continuation of application No. 16/570,553, filed on Sep. 13, 2019, now Pat. No. 10,780,121, which is a continuation of application No. PCT/US2019/048922, filed on Aug. 29, 2019.

(60) Provisional application No. 62/724,596, filed on Aug. 29, 2018.

(51) Int. Cl.
| C07K 14/705 | (2006.01) |
| C07K 19/00 | (2006.01) |
| A61K 35/17 | (2015.01) |
| C07K 14/725 | (2006.01) |
| C12N 5/0783 | (2010.01) |
| C07K 16/22 | (2006.01) |

(52) U.S. Cl.
CPC .......... *A61K 35/17* (2013.01); *C07K 14/7051* (2013.01); *C07K 14/7056* (2013.01); *C07K 14/70521* (2013.01); *C07K 14/70578* (2013.01); *C07K 16/22* (2013.01); *C12N 5/0636* (2013.01); *C07K 2317/53* (2013.01); *C07K 2319/03* (2013.01)

(58) Field of Classification Search
None
See application file for complete search history.

(56) References Cited

U.S. PATENT DOCUMENTS

| 5,844,095 | A | 12/1998 | Linsley et al. |
| 7,569,663 | B2 | 8/2009 | Tykocinski et al. |
| 7,696,168 | B2 | 4/2010 | Kuliopulos et al. |
| 8,039,437 | B2 | 10/2011 | Tykocinski et al. |
| 8,080,246 | B2 | 12/2011 | Lin et al. |
| 8,329,657 | B2 | 12/2012 | Tykocinski et al. |
| 8,735,553 | B1 | 5/2014 | Li et al. |
| 9,029,315 | B2 | 5/2015 | Chen et al. |
| 9,221,895 | B2 | 12/2015 | Tykocinski et al. |
| 9,352,037 | B2 | 5/2016 | Van Den Berg |
| 9,388,230 | B2 | 7/2016 | Elhalel |
| 9,493,575 | B2 | 11/2016 | Jaiswal et al. |
| 9,657,082 | B2 | 5/2017 | Tykocinski |
| 9,845,345 | B2 | 12/2017 | Ring et al. |
| 9,969,789 | B2 | 5/2018 | Uger et al. |
| 2003/0232323 | A1 | 12/2003 | Freeman et al. |
| 2007/0036783 | A1 | 2/2007 | Humeau et al. |
| 2008/0131431 | A1 | 6/2008 | Smith et al. |
| 2009/0226435 | A1 | 9/2009 | Khare |
| 2011/0041190 | A1 | 2/2011 | Tykocinski et al. |
| 2013/0039911 | A1 | 2/2013 | Bedi et al. |
| 2013/0065815 | A1 | 3/2013 | Tykocinski et al. |
| 2013/0243697 | A1 | 9/2013 | Tykocinski et al. |
| 2014/0113370 | A1 | 4/2014 | Camphausen et al. |
| 2014/0154252 | A1 | 6/2014 | Thompson et al. |
| 2014/0227315 | A1 | 8/2014 | Tykocinski et al. |
| 2014/0242077 | A1 | 8/2014 | Choi et al. |
| 2014/0286858 | A1 | 9/2014 | Zimmerman et al. |
| 2015/0098942 | A1 | 4/2015 | Curti et al. |
| 2015/0174268 | A1 | 6/2015 | Li |
| 2015/0183881 | A1 | 7/2015 | Bedi et al. |
| 2015/0190506 | A1 | 7/2015 | Cheung et al. |
| 2015/0191525 | A1 | 7/2015 | Epstein et al. |
| 2015/0266942 | A1 | 9/2015 | Tian |
| 2015/0353642 | A1 | 12/2015 | Tykocinski |
| 2015/0368350 | A1 | 12/2015 | Tykocinski et al. |
| 2015/0376260 | A1 | 12/2015 | Elhalel et al. |
| 2016/0024176 | A1 | 1/2016 | Damschroder et al. |
| 2016/0166685 | A1 | 6/2016 | Cheung et al. |
| 2016/0177276 | A1 | 6/2016 | Lo et al. |
| 2016/0186150 | A1 | 6/2016 | Deming et al. |
| 2016/0250322 | A1 | 9/2016 | Schreiber et al. |
| 2016/0256527 | A1 | 9/2016 | Gurney |
| 2016/0340409 | A1 | 11/2016 | Dranitzki-Elhalel |
| 2016/0340430 | A1 | 11/2016 | Bedi et al. |

(Continued)

FOREIGN PATENT DOCUMENTS

| WO | WO 94/26891 | 11/1994 |
| WO | WO 2001049318 | 12/2001 |

(Continued)

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Compaan, et al., "The Crystal Structure of the Costimulatory OX40-OX40L Complex," Structure, 14, Aug. 2006, pp. 1321-1330.
Fromm, et al., "Agonist redirected checkpoint, PD1-Fc-OX40L, for cancer immunotherapy," Journal for ImmunoTherapy of Cancer, (2018) 6:149, 16 pages.

(Continued)

*Primary Examiner* — Christine J Saoud
*Assistant Examiner* — Jon M Lockard
(74) *Attorney, Agent, or Firm* — Morgan, Lewis & Bockius LLP

(57) ABSTRACT

The present invention relates, inter alia, to compositions and methods, including chimeric proteins comprising an extracellular domain of FMS like tyrosine kinase 3 ligand (FLT3L) and an extracellular domain of a Type II transmembrane protein that find use in the treatment of disease, such as cancer.

3 Claims, 18 Drawing Sheets

Specification includes a Sequence Listing.

(56) References Cited

U.S. PATENT DOCUMENTS

| | | |
|---|---|---|
| 2016/0347846 A1 | 12/2016 | Tykocinski |
| 2017/0107270 A1 | 4/2017 | Pons et al. |
| 2018/0142019 A1 | 5/2018 | Manning et al. |

FOREIGN PATENT DOCUMENTS

| | | |
|---|---|---|
| WO | WO 2005047334 | 5/2005 |
| WO | WO 2007/149880 A2 | 12/2007 |
| WO | WO 2008061377 | 5/2008 |
| WO | WO 2010003118 | 1/2010 |
| WO | WO 2010005519 | 1/2010 |
| WO | WO 2010070047 | 6/2010 |
| WO | WO 2010105068 | 9/2010 |
| WO | WO 2012042480 | 4/2012 |
| WO | WO 2013000234 | 1/2013 |
| WO | WO 2013019615 | 2/2013 |
| WO | WO 2013164694 | 11/2013 |
| WO | WO 2013173820 | 11/2013 |
| WO | WO 2014094122 | 6/2014 |
| WO | WO 2014106839 | 6/2014 |
| WO | WO 2014121085 | 8/2014 |
| WO | WO 2014121093 | 8/2014 |
| WO | WO 2014121099 | 8/2014 |
| WO | WO 2014134165 | 9/2014 |
| WO | WO 2014164427 | 10/2014 |
| WO | WO 2015095423 | 6/2015 |
| WO | WO 2015104406 | 7/2015 |
| WO | WO 2015112534 | 7/2015 |
| WO | WO 2015116178 | 8/2015 |
| WO | WO 2015183902 | 12/2015 |
| WO | WO 2015200828 | 12/2015 |
| WO | WO 2016025385 | 2/2016 |
| WO | WO 2016126608 | 8/2016 |
| WO | WO 2016166139 | 10/2016 |
| WO | WO 2017/059168 A1 | 4/2017 |

OTHER PUBLICATIONS

Graddis, et al., "Structure-Function Analysis of FLT3 Ligand-FLT3 Receptor Interactions Using a Rapid Functional Screen," The Journal of Biological Chemistry, vol. 273, No. 28, Jul. 10, 1998, pp. 17626-17633.
Savvides, et al., "Flt3 ligand structure and unexpected commonalities of helical bundles and cystine knots," Nat Struct Biol. 7(6):486-91 (2000).
Zhang, et al., "Structural and Functional Analysis of the Costimulatory Receptor Programmed Death-1," Immunity, vol. 20, Mar. 2004, pp. 337-347.
Zorn, et al., "Crystal Structure of the FLT3 Kinase Domain Bound to the Inhibitor Quizartinib (AC220)," PLoS One 10(4): e0121177, 15 pages.
Ali, et al. "Anti-tumour therapeutic efficacy of OX40L in murine tumour model." Vaccine, 22: 3585-3594, 2004.
Anderson, et al. "Lag-3, Tim-3, and TIGIT: Co-Inhibitory Receptors with Specialized Functions in Immune Regulation," Immunity vol. 44, 2016, pp. 989-1004.
Barclay, "Signal Regulatory protein akpha (SIRPα)/CD47 interaction and function," Current Opinion in Immunology, 21:47-52, 2009.
Barclay, et al., "The Interaction Between Signal Regulatory Protein Alpha (SIRPα) and CD47: Structure, Function, and Therapeutic Target," Annu. Rev. Immunol, 32:25-50, 2014.
Bartkowiak, et al. "4-1 BB agonists: Multi-Potent Potentiators of Tumor Immunity," Frontiers in Oncology, 2015, vol. 5, Article 117, pp. 1-16.
Batlevi, et al. "Novel Immunotherapies in Lymphoid Malignancies," Nature Reviews, Clinical Oncology, vol. 13, 2016, pp. 25-40.
Callahan, et al. "Targeting T Cell Co-receptors for Cancer Therapy," Immunity, vol. 44, 2016, pp. 1069-1078.
Chao, et al. "The CD47-SIRPα pathway in cancer immune evasion and potential therapeutic implications." Current Opinion in Immunology, 24: 225-232, 2012.
Curran et al. "Editorial: Advances in Combination Tumor Immunotherapy," Frontiers in Oncology, 2015, vol. 5, Article 198, pp. 1-2.
Daver, et al., "Targeting FLT3 mutations in AML: review of current knowledge and evidence," Leukemia, 2019, 33: 299-312.
de Visser, et al., "The interplay between innate and adaptive immunity regulates cancer development," Cancer Immunology, Immunotherapy, vol. 54, No. 11, pp. 1143-1152, May 12, 2005.
de Visser et al., "Paradoxial Roles of the Immune System During Cancer Development," Nature Reviews Cancer, (2006) 6:24-37.
Guo, et al. "PD-1 Blockade and OX40 Triggering Synergistically Protects Against Tumor Growth in a Murine Model of Ovarian Cancer," PLOS One, 2014, vol. 9, issue 2, pp. 1-10.
Hatherley, et al., "The Structure of the Macrophage Signal Regulatory Protein α (SIRPα) Inhibitory Receptor Reveals a Binding Face Reminiscent of That Used by T Cell Receptors," The Journal Of Biological Chemistry, vol. 282, No. 19, pp. 14567-14575, 2007.
Hirano, et al. "Inhibition of human breast carcinoma growth by a soluble recombinant human CD40 ligand." Blood, 93(9): 2999-3007, 1999.
Huang, et al. "CTLA-4-FAS ligand functions as a trans signal converter protein in bridging antigen-presenting cells and T cells," International Immunology, vol. 13, No. 4, 2001, pp. 529-539.
International Search Report and Written Opinion, International Application No. PCT/US2016/054598, dated Jan. 9, 2017, 17 pages.
Karman, et al. "Ligation of Cytoxic T Lymphocyte Antigen-4 to T Cell Receptor Inhibits T Cell Activation and Directs Differentiation into Foxp3+ Regulatory T Cells," The Journal of Biological Chemistry, vol. 287, No. 14, 2012, pp. 11098-11107.
Karpusas, et al., "2 Å crystal structure of an extracellular fragment of human CD40 ligand," Structure, 3:1031-1039, 1995.
Karsunky, et al., "Flt3 Ligand Regulates Dendritic Cell Development from Flt3+ Lymphoid and Myeloid-committed Progenitors to Flt3+ Dendritic Cells In Vivo," J. Exp. Med, vol. 198, No. 2, Jul. 21, 2003, pp. 305-313.
Kermer, et al. "An Antibody Fusion Protein for Cancer Immunotherapy Mimicking IL-15 trans-Presentation at the Tumor Site," Molecular Cancer Therapeutics, vol. 11, No. 6, 2012, pp. 1279-1288.
Khalil, et al. "The Future of Cancer Treatment: Immunomodulation, CARs and Combination Immunotherapy," Nature Reviews Clinical Oncology, 2016, pp. 1-18.
Ledford, "The Perfect Blend," Nature, vol. 532, 2016, pp. 162-164.
Lee, et al., "Novel Structural Determinants of SIRPα that Mediate Binding of CD47," The Journal of Immunology, 179, 7741-7750, 2007.
Linch, et al. "OX40 Agonists and Combination Immunotherapy: Putting the Pedal to the Metal," Frontiers in Oncology, vol. 5, article 34, 2015, pp. 1-14.
Ma, et al. "The role of CD40 and CD40L in Dendritic Cells" Sem. in Immuno., 21: 265-272, 2009.
Mahoney, Combination Cancer Immunotherapy and New Immunomodulatory Targets Nature Reviews Drug Discovery (2015) 14: 561-585.
Marcus, et al., "Recognition of tumors by the innate immune system and natural killer cells," Advances in Immunology, vol. 122, pp. 91-128, Jan. 1, 2015.
Orbach, et al. "CD40•FasL and CTGLA-4•FasL Fusion Proteins Induce Apoptosis in Malignant Cell Lines by Dual Signaling," American Journal of Pathology, vol. 177, No. 6, 2010, pp. 3159-3168.
Pardoll, "The Blockade of Immune Checkpoints in Cancer Immunotherapy," Nature Reviews Cancer, vol. 12, 2012, pp. 252-264.
Schildberg, et al. "Coinhibitory Pathways in B7-CD28 Ligand-Receptor Family," Immunity, vol. 44, 2016, pp. 955-972.
Scott, et al. "Antibody Therapy of Cancer," Nature Reviews Cancer, vol. 12, 2012, pp. 278-287.
Spiess, et al. "Alternative Molecular Formats and Therapeutic Applications for Bispecific Antibodies," Molecular Immunology, vol. 67, 2015, pp. 95-106.
Verstraete, et al., "Structural insights into the extracellular assembly of the hematopoietic Flt3 signaling complex," Blood, vol. 118, No. 1, Jul. 7, 2011, pp. 60-68.

(56) References Cited

OTHER PUBLICATIONS

Ward-Kavanagh, et al. "The TNF Receptor Superfamily in Co-stimulating and Co-inhibitory Responses," Immunity, vol. 44, 2016, pp. 1005-1019.
Xu, et al., "Differential Development of Murine Dendritic Cells by GM-CSF versus Flt3 Ligand Has Implications for Inflammation and Trafficking," J Immunol 2007, 179 (11): 7577-7584.
Zhang, et al. "Targeted and Untargeted CD 137L Fusion Proteins for the Immunotherapy of Experimental Solid Tumors," Clin Cancer Res 2007, vol. 13, No. 9, pp. 2578-2767.
Zhao et al., "A Bispecific Protein Capable of Engaging CTLA-4 and MHCII Protects Non-Obese Diabetic Mice from Autoimmune Diabetes," Plos One, vol. 8, Issue 5, 2013, pp. 1-11.

\* cited by examiner

| Sample ID | Loading | Conc. (nM) | KD (nM) | Kon (1/Ms) | Koff (1/s) | Full $R^2$ |
|---|---|---|---|---|---|---|
| mFLT3L-Fc-CD40L | mFLT3-his | 142.9 | 15.2 | 2.05 E+05 | 3.12 E-03 | 0.9654 |
| mFLT3L-Fc-CD40L | mCD40-his | 142.9 | 14.2 | 6.18 E+04 | 8.58 E-04 | 0.995 |

SEQUENCE LISTING

```
<160> NUMBER OF SEQ ID NOS: 63

<210> SEQ ID NO 1
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 1

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Ser Gly Lys Glu Tyr Lys Cys Lys Val Ser Ser Lys
                85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Ser Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 2
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 2
```

-continued

Ala Pro Glu Phe Leu Gly Gly Pro Ser Val Phe Leu Phe Pro Pro Lys
1               5                   10                  15

Pro Lys Asp Gln Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
50                  55                  60

Gln Phe Asn Ser Thr Tyr Arg Val Val Ser Val Leu Thr Thr Pro His
65                  70                  75                  80

Ser Asp Trp Leu Ser Gly Lys Glu Tyr Lys Cys Lys Val Ser Ser Lys
                85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Ser Trp Gln Glu Gly Asn Val
            180                 185                 190

Phe Ser Cys Ser Val Leu His Glu Ala Leu His Asn His Tyr Thr Gln
        195                 200                 205

Lys Ser Leu Ser Leu Ser Leu Gly Lys
    210                 215

<210> SEQ ID NO 3
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 3

Ala Pro Glu Phe Leu Gly Gly Pro Ser Val Phe Leu Phe Pro Pro Lys
1               5                   10                  15

Pro Lys Asp Gln Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
50                  55                  60

Gln Phe Asn Ser Thr Tyr Arg Val Val Ser Val Leu Thr Val Leu His
65                  70                  75                  80

Gln Asp Trp Leu Ser Gly Lys Glu Tyr Lys Cys Lys Val Ser Ser Lys
                85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

```
Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Leu His Glu Ala Leu His Asn His Tyr Thr Gln
        195                 200                 205

Lys Ser Leu Ser Leu Ser Leu Gly Lys
    210                 215

<210> SEQ ID NO 4
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 4

Ser Lys Tyr Gly Pro Pro Cys Pro Ser Cys Pro
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 5

Ser Lys Tyr Gly Pro Pro Cys Pro Pro Cys Pro
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 6

Ser Lys Tyr Gly Pro Pro
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 7

Ile Glu Gly Arg Met Asp
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 8

Gly Gly Gly Val Pro Arg Asp Cys Gly
1               5
```

<210> SEQ ID NO 9
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 9

```
Ile Glu Gly Arg Met Asp Gly Gly Gly Ala Gly Gly Gly Gly
1               5                   10                  15
```

<210> SEQ ID NO 10
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 10

```
Gly Gly Gly Ser Gly Gly Gly Ser
1               5
```

<210> SEQ ID NO 11
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 11

```
Gly Gly Gly Ser Gly Gly Gly Ser Gly Gly Gly
1               5                   10
```

<210> SEQ ID NO 12
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 12

```
Glu Gly Lys Ser Ser Gly Ser Gly Ser Glu Ser Lys Ser Thr
1               5                   10
```

<210> SEQ ID NO 13
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 13

```
Gly Gly Ser Gly
1
```

<210> SEQ ID NO 14
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 14

```
Gly Gly Ser Gly Gly Gly Ser Gly Gly Gly Ser Gly
1               5                   10
```

```
<210> SEQ ID NO 15
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 15

Glu Ala Ala Ala Lys Glu Ala Ala Ala Lys Glu Ala Ala Ala Lys
1               5                   10                  15

<210> SEQ ID NO 16
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 16

Glu Ala Ala Ala Arg Glu Ala Ala Ala Arg Glu Ala Ala Ala Arg Glu
1               5                   10                  15

Ala Ala Ala Arg
            20

<210> SEQ ID NO 17
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 17

Gly Gly Gly Gly Ser Gly Gly Gly Gly Ser Gly Gly Gly Gly Ser Ala
1               5                   10                  15

Ser

<210> SEQ ID NO 18
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 18

Gly Gly Gly Gly Ala Gly Gly Gly Gly
1               5

<210> SEQ ID NO 19

<400> SEQUENCE: 19

000

<210> SEQ ID NO 20
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 20

Gly Ser Gly Ser Gly Ser
1               5

<210> SEQ ID NO 21
```

```
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 21

Gly Ser Gly Ser Gly Ser Gly Ser Gly Ser
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 22

Gly Gly Gly Gly Ser Ala Ser
1               5

<210> SEQ ID NO 23
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 23

Ala Pro Ala Pro Ala Pro Ala Pro Ala Pro Ala Pro Ala Pro Ala Pro
1               5                   10                  15

Ala Pro Ala Pro
            20

<210> SEQ ID NO 24
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 24

Cys Pro Pro Cys
1

<210> SEQ ID NO 25
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 25

Gly Gly Gly Gly Ser
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 26

Gly Gly Gly Gly Ser Gly Gly Gly Gly Ser
1               5                   10
```

```
<210> SEQ ID NO 27
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 27

Gly Gly Gly Gly Ser Gly Gly Gly Gly Ser Gly Gly Gly Gly Ser
1               5                   10                  15

<210> SEQ ID NO 28
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 28

Gly Gly Gly Gly Ser Gly Gly Gly Gly Ser Gly Gly Gly Gly Ser Gly
1               5                   10                  15

Gly Gly Gly Ser
            20

<210> SEQ ID NO 29
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 29

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 30
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 30

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 31
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 31

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35
```

<210> SEQ ID NO 32
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 32

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 33
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 33

Gly Gly Ser Gly Gly Ser Gly Gly Gly Gly Ser Gly Gly Gly Gly Ser
1               5                   10                  15

<210> SEQ ID NO 34
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 34

Gly Gly Gly Gly Gly Gly Gly Gly
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 35

Gly Gly Gly Gly Gly Gly
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 36

Glu Ala Ala Ala Lys
1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic Polypeptide

```
<400> SEQUENCE: 37

Glu Ala Ala Ala Lys Glu Ala Ala Ala Lys
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 38

Glu Ala Ala Ala Lys Glu Ala Ala Ala Lys Glu Ala Ala Ala Lys
1               5                   10                  15

<210> SEQ ID NO 39
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 39

Ala Glu Ala Ala Ala Lys Glu Ala Ala Ala Lys Ala
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 40

Ala Glu Ala Ala Ala Lys Glu Ala Ala Ala Lys Glu Ala Ala Ala Lys
1               5                   10                  15

Ala

<210> SEQ ID NO 41
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 41

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 42
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 42

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25
```

```
<210> SEQ ID NO 43
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 43

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
        35                  40                  45

<210> SEQ ID NO 44
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 44

Pro Ala Pro Ala Pro
1               5

<210> SEQ ID NO 45
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 45

Lys Glu Ser Gly Ser Val Ser Ser Glu Gln Leu Ala Gln Phe Arg Ser
1               5                   10                  15

Leu Asp

<210> SEQ ID NO 46
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 46

Gly Ser Ala Gly Ser Ala Ala Gly Ser Gly Glu Phe
1               5                   10

<210> SEQ ID NO 47
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 47

Gly Gly Gly Ser Glu
1               5

<210> SEQ ID NO 48
<211> LENGTH: 5
<212> TYPE: PRT
<213> ORGANISM: Artificial Sequence
<220> FEATURE:
```

```
<223> OTHER INFORMATION: Synthetic Polypeptide

<400> SEQUENCE: 48

Gly Ser Glu Ser Gly
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 49

Gly Ser Glu Gly Ser
1               5

<210> SEQ ID NO 50
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 50

Gly Glu Gly Gly Ser Gly Glu Gly Ser Ser Gly Glu Gly Ser Ser Ser
1               5                   10                  15

Glu Gly Gly Gly Ser Glu Gly Gly Ser Glu Gly Gly Gly Ser Glu
            20                  25                  30

Gly Gly Ser
        35

<210> SEQ ID NO 51
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 51

Ser Lys Tyr Gly Pro Pro Cys Pro Ser Cys Pro Ala Pro Glu Phe Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160
```

Glu Trp Glu Ser Asn Gly Gln Pro Glu Asn Asn Tyr Lys Thr Thr Pro
                    165                 170                 175

Pro Val Leu Asp Ser Asp Gly Ser Phe Phe Leu Tyr Ser Arg Leu Thr
            180                 185                 190

Val Asp Lys Ser Ser Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys Ile Glu Gly Arg Met Asp
225                 230

<210> SEQ ID NO 52
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 52

Ser Lys Tyr Gly Pro Pro Cys Pro Ser Cys Pro Ala Pro Glu Phe Leu
1               5                   10                  15

Gly Gly Pro Ser Val Phe Leu Phe Pro Pro Lys Pro Lys Asp Gln Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Thr Pro His Ser Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Ser Trp Gln Glu Gly Asn Val Phe Ser Cys Ser Val
        195                 200                 205

Leu His Glu Ala Leu His Asn His Tyr Thr Gln Lys Ser Leu Ser Leu
    210                 215                 220

Ser Leu Gly Lys Ile Glu Gly Arg Met Asp
225                 230

<210> SEQ ID NO 53
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 53

Ser Lys Tyr Gly Pro Pro Cys Pro Ser Cys Pro Ala Pro Glu Phe Leu
1               5                   10                  15

Gly Gly Pro Ser Val Phe Leu Phe Pro Pro Lys Pro Lys Asp Gln Leu
            20                  25                  30

Met Ile Ser Arg Thr Pro Glu Val Thr Cys Val Val Asp Val Ser
            35                  40                  45

Gln Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
            115                 120                 125

Val Tyr Thr Leu Pro Pro Ser Gln Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
            165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
            195                 200                 205

Leu His Glu Ala Leu His Asn His Tyr Thr Gln Lys Ser Leu Ser Leu
        210                 215                 220

Ser Leu Gly Lys Ile Glu Gly Arg Met Asp
225                 230

<210> SEQ ID NO 54
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 54

Ser Lys Tyr Gly Pro Pro Cys Pro Ser Cys Pro Ala Pro Glu Phe Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Asp Val Ser
            35                  40                  45

Gln Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
            115                 120                 125

```
Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                    165                 170                 175

Pro Val Leu Asp Ser Asp Gly Ser Phe Phe Leu Tyr Ser Arg Leu Thr
                180                 185                 190

Val Asp Lys Ser Ser Trp Gln Glu Gly Asn Val Phe Ser Cys Ser Val
            195                 200                 205

Met His Glu Ala Leu His Asn His Tyr Thr Gln Lys Ser Leu Ser Leu
        210                 215                 220

Ser Leu Gly Lys Ile Glu Gly Arg Met Asp
225                 230

<210> SEQ ID NO 55
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 55

Ser Lys Tyr Gly Pro Pro Cys Pro Pro Cys Pro Ala Pro Glu Phe Leu
1               5                   10                  15

Gly Gly Pro Ser Val Phe Leu Phe Pro Pro Lys Pro Lys Asp Gln Leu
                20                  25                  30

Met Ile Ser Arg Thr Pro Glu Val Thr Cys Val Val Val Asp Val Ser
            35                  40                  45

Gln Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Tyr Arg Val Val Ser Val Leu Thr Thr Pro His Ser Asp Trp Leu Ser
                85                  90                  95

Gly Lys Glu Tyr Lys Cys Lys Val Ser Ser Lys Gly Leu Pro Ser Ser
                100                 105                 110

Ile Glu Lys Thr Ile Ser Asn Ala Thr Gly Gln Pro Arg Glu Pro Gln
            115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                    165                 170                 175

Pro Val Leu Asp Ser Asp Gly Ser Phe Phe Leu Tyr Ser Arg Leu Thr
                180                 185                 190

Val Asp Lys Ser Ser Trp Gln Glu Gly Asn Val Phe Ser Cys Ser Val
            195                 200                 205

Leu His Glu Ala Leu His Asn His Tyr Thr Gln Lys Ser Leu Ser Leu
        210                 215                 220

Ser Leu Gly Lys Ile Glu Gly Arg Met Asp
225                 230

<210> SEQ ID NO 56
```

```
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 56
```

| Ser | Lys | Tyr | Gly | Pro | Pro | Cys | Pro | Pro | Cys | Pro | Ala | Pro | Glu | Phe | Leu |
|---|---|---|---|---|---|---|---|---|---|---|---|---|---|---|---|
| 1 | | | | 5 | | | | | 10 | | | | | 15 | |

| Gly | Gly | Pro | Ser | Val | Phe | Leu | Phe | Pro | Pro | Lys | Pro | Lys | Asp | Gln | Leu |
|---|---|---|---|---|---|---|---|---|---|---|---|---|---|---|---|
| | | | 20 | | | | | 25 | | | | | 30 | | |

| Met | Ile | Ser | Arg | Thr | Pro | Glu | Val | Thr | Cys | Val | Val | Val | Asp | Val | Ser |
|---|---|---|---|---|---|---|---|---|---|---|---|---|---|---|---|
| | | 35 | | | | | 40 | | | | | 45 | | | |

| Gln | Glu | Asp | Pro | Glu | Val | Gln | Phe | Asn | Trp | Tyr | Val | Asp | Gly | Val | Glu |
|---|---|---|---|---|---|---|---|---|---|---|---|---|---|---|---|
| | 50 | | | | | 55 | | | | | 60 | | | | |

| Val | His | Asn | Ala | Lys | Thr | Lys | Pro | Arg | Glu | Glu | Gln | Phe | Asn | Ser | Thr |
|---|---|---|---|---|---|---|---|---|---|---|---|---|---|---|---|
| 65 | | | | | 70 | | | | | 75 | | | | | 80 |

| Tyr | Arg | Val | Val | Ser | Val | Leu | Thr | Val | Leu | His | Gln | Asp | Trp | Leu | Ser |
|---|---|---|---|---|---|---|---|---|---|---|---|---|---|---|---|
| | | | | 85 | | | | | 90 | | | | | 95 | |

| Gly | Lys | Glu | Tyr | Lys | Cys | Lys | Val | Ser | Ser | Lys | Gly | Leu | Pro | Ser | Ser |
|---|---|---|---|---|---|---|---|---|---|---|---|---|---|---|---|
| | | | 100 | | | | | 105 | | | | | 110 | | |

| Ile | Glu | Lys | Thr | Ile | Ser | Asn | Ala | Thr | Gly | Gln | Pro | Arg | Glu | Pro | Gln |
|---|---|---|---|---|---|---|---|---|---|---|---|---|---|---|---|
| | | 115 | | | | | 120 | | | | | 125 | | | |

| Val | Tyr | Thr | Leu | Pro | Pro | Ser | Gln | Glu | Glu | Met | Thr | Lys | Asn | Gln | Val |
|---|---|---|---|---|---|---|---|---|---|---|---|---|---|---|---|
| | 130 | | | | | 135 | | | | | 140 | | | | |

| Ser | Leu | Thr | Cys | Leu | Val | Lys | Gly | Phe | Tyr | Pro | Ser | Asp | Ile | Ala | Val |
|---|---|---|---|---|---|---|---|---|---|---|---|---|---|---|---|
| 145 | | | | | 150 | | | | | 155 | | | | | 160 |

| Glu | Trp | Glu | Ser | Asn | Gly | Gln | Pro | Glu | Asn | Asn | Tyr | Lys | Thr | Thr | Pro |
|---|---|---|---|---|---|---|---|---|---|---|---|---|---|---|---|
| | | | | 165 | | | | | 170 | | | | | 175 | |

| Pro | Val | Leu | Asp | Ser | Asp | Gly | Ser | Phe | Phe | Leu | Tyr | Ser | Arg | Leu | Thr |
|---|---|---|---|---|---|---|---|---|---|---|---|---|---|---|---|
| | | | 180 | | | | | 185 | | | | | 190 | | |

| Val | Asp | Lys | Ser | Arg | Trp | Gln | Glu | Gly | Asn | Val | Phe | Ser | Cys | Ser | Val |
|---|---|---|---|---|---|---|---|---|---|---|---|---|---|---|---|
| | | 195 | | | | | 200 | | | | | 205 | | | |

| Leu | His | Glu | Ala | Leu | His | Asn | His | Tyr | Thr | Gln | Lys | Ser | Leu | Ser | Leu |
|---|---|---|---|---|---|---|---|---|---|---|---|---|---|---|---|
| | 210 | | | | | 215 | | | | | 220 | | | | |

| Ser | Leu | Gly | Lys | Ile | Glu | Gly | Arg | Met | Asp |
|---|---|---|---|---|---|---|---|---|---|
| 225 | | | | | 230 | | | | |

```
<210> SEQ ID NO 57
<211> LENGTH: 158
<212> TYPE: PRT
<213> ORGANISM: Artificial Sequence
<220> FEATURE:
<223> OTHER INFORMATION: Synthetic polypeptide

<400> SEQUENCE: 57
```

| Thr | Gln | Asp | Cys | Ser | Phe | Gln | His | Ser | Pro | Ile | Ser | Ser | Asp | Phe | Ala |
|---|---|---|---|---|---|---|---|---|---|---|---|---|---|---|---|
| 1 | | | | 5 | | | | | 10 | | | | | 15 | |

| Val | Lys | Ile | Arg | Glu | Leu | Ser | Asp | Tyr | Leu | Leu | Gln | Asp | Tyr | Pro | Val |
|---|---|---|---|---|---|---|---|---|---|---|---|---|---|---|---|
| | | | 20 | | | | | 25 | | | | | 30 | | |

| Thr | Val | Ala | Ser | Asn | Leu | Gln | Asp | Glu | Glu | Leu | Cys | Gly | Gly | Leu | Trp |
|---|---|---|---|---|---|---|---|---|---|---|---|---|---|---|---|
| | | 35 | | | | | 40 | | | | | 45 | | | |

| Arg | Leu | Val | Leu | Ala | Gln | Arg | Trp | Met | Glu | Arg | Leu | Lys | Thr | Val | Ala |
|---|---|---|---|---|---|---|---|---|---|---|---|---|---|---|---|
| | 50 | | | | | 55 | | | | | 60 | | | | |

| Gly | Ser | Lys | Met | Gln | Gly | Leu | Leu | Glu | Arg | Val | Asn | Thr | Glu | Ile | His |
|---|---|---|---|---|---|---|---|---|---|---|---|---|---|---|---|
| 65 | | | | | 70 | | | | | 75 | | | | | 80 |

| Phe | Val | Thr | Lys | Cys | Ala | Phe | Gln | Pro | Pro | Pro | Ser | Cys | Leu | Arg | Phe |
|---|---|---|---|---|---|---|---|---|---|---|---|---|---|---|---|

```
                    85                  90                  95
Val Gln Thr Asn Ile Ser Arg Leu Leu Gln Glu Thr Ser Glu Gln Leu
                100                 105                 110

Val Ala Leu Lys Pro Trp Ile Thr Arg Gln Asn Phe Ser Arg Cys Leu
            115                 120                 125

Glu Leu Gln Cys Gln Pro Asp Ser Ser Thr Leu Pro Pro Trp Ser
130                 135                 140

Pro Arg Pro Leu Glu Ala Thr Ala Pro Thr Ala Pro Gln Pro
145                 150                 155

<210> SEQ ID NO 58
<211> LENGTH: 205
<212> TYPE: PRT
<213> ORGANISM: Artificial Sequence
<220> FEATURE:
<223> OTHER INFORMATION: Synthetic polypeptide

<400> SEQUENCE: 58

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
                100                 105                 110

Ser Leu Ala Leu His Leu Gln Pro Leu Arg Ser Ala Ala Gly Ala Ala
            115                 120                 125

Ala Leu Ala Leu Thr Val Asp Leu Pro Pro Ala Ser Ser Glu Ala Arg
        130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
                180                 185                 190

Pro Glu Ile Pro Ala Gly Leu Pro Ser Pro Arg Ser Glu
            195                 200                 205

<210> SEQ ID NO 59
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 59

His Arg Arg Leu Asp Lys Ile Glu Asp Glu Arg Asn Leu His Glu Asp
1               5                   10                  15

Phe Val Phe Met Lys Thr Ile Gln Arg Cys Asn Thr Gly Glu Arg Ser
            20                  25                  30
```

Leu Ser Leu Leu Asn Cys Glu Glu Ile Lys Ser Gln Phe Glu Gly Phe
            35                  40                  45

Val Lys Asp Ile Met Leu Asn Lys Glu Thr Lys Lys Glu Asn Ser
 50                  55                  60

Phe Glu Met Gln Lys Gly Asp Gln Asn Pro Gln Ile Ala Ala His Val
 65                  70                  75                  80

Ile Ser Glu Ala Ser Ser Lys Thr Thr Ser Val Leu Gln Trp Ala Glu
                    85                  90                  95

Lys Gly Tyr Tyr Thr Met Ser Asn Asn Leu Val Thr Leu Glu Asn Gly
               100                 105                 110

Lys Gln Leu Thr Val Lys Arg Gln Gly Leu Tyr Tyr Ile Tyr Ala Gln
               115                 120                 125

Val Thr Phe Cys Ser Asn Arg Glu Ala Ser Ser Gln Ala Pro Phe Ile
130                 135                 140

Ala Ser Leu Cys Leu Lys Ser Pro Gly Arg Phe Glu Arg Ile Leu Leu
145                 150                 155                 160

Arg Ala Ala Asn Thr His Ser Ser Ala Lys Pro Cys Gly Gln Gln Ser
                    165                 170                 175

Ile His Leu Gly Gly Val Phe Glu Leu Gln Pro Gly Ala Ser Val Phe
               180                 185                 190

Val Asn Val Thr Asp Pro Ser Gln Val Ser His Gly Thr Gly Phe Thr
               195                 200                 205

Ser Phe Gly Leu Leu Lys Leu
               210                 215

<210> SEQ ID NO 60
<211> LENGTH: 155
<212> TYPE: PRT
<213> ORGANISM: Artificial Sequence
<220> FEATURE:
<223> OTHER INFORMATION: Synthetic polypeptide

<400> SEQUENCE: 60

Gln Arg Phe Ala Gln Ala Gln Gln Leu Pro Leu Glu Ser Leu Gly
 1               5                  10                  15

Trp Asp Val Ala Glu Leu Gln Leu Asn His Thr Gly Pro Gln Gln Asp
                20                  25                  30

Pro Arg Leu Tyr Trp Gln Gly Gly Pro Ala Leu Gly Arg Ser Phe Leu
            35                  40                  45

His Gly Pro Glu Leu Asp Lys Gly Gln Leu Arg Ile His Arg Asp Gly
 50                  55                  60

Ile Tyr Met Val His Ile Gln Val Thr Leu Ala Ile Cys Ser Ser Thr
 65                  70                  75                  80

Thr Ala Ser Arg His His Pro Thr Thr Leu Ala Val Gly Ile Cys Ser
                    85                  90                  95

Pro Ala Ser Arg Ser Ile Ser Leu Leu Arg Leu Ser Phe His Gln Gly
               100                 105                 110

Cys Thr Ile Ala Ser Gln Arg Leu Thr Pro Leu Ala Arg Gly Asp Thr
               115                 120                 125

Leu Cys Thr Asn Leu Thr Gly Thr Leu Leu Pro Ser Arg Asn Thr Asp
130                 135                 140

Glu Thr Phe Phe Gly Val Gln Trp Val Arg Pro
145                 150                 155

<210> SEQ ID NO 61
<211> LENGTH: 133

```
<212> TYPE: PRT
<213> ORGANISM: Artificial Sequence
<220> FEATURE:
<223> OTHER INFORMATION: Synthetic polypeptide

<400> SEQUENCE: 61

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 62
<211> LENGTH: 126
<212> TYPE: PRT
<213> ORGANISM: Artificial Sequence
<220> FEATURE:
<223> OTHER INFORMATION: Synthetic polypeptide

<400> SEQUENCE: 62

Glu Thr Ala Lys Glu Pro Cys Met Ala Lys Phe Gly Pro Leu Pro Ser
1               5                   10                  15

Lys Trp Gln Met Ala Ser Ser Glu Pro Pro Cys Val Asn Lys Val Ser
            20                  25                  30

Asp Trp Lys Leu Glu Ile Leu Gln Asn Gly Leu Tyr Leu Ile Tyr Gly
        35                  40                  45

Gln Val Ala Pro Asn Ala Asn Tyr Asn Asp Val Ala Pro Phe Glu Val
    50                  55                  60

Arg Leu Tyr Lys Asn Lys Asp Met Ile Gln Thr Leu Thr Asn Lys Ser
65                  70                  75                  80

Lys Ile Gln Asn Val Gly Gly Thr Tyr Glu Leu His Val Gly Asp Thr
                85                  90                  95

Ile Asp Leu Ile Phe Asn Ser Glu His Gln Val Leu Lys Asn Asn Thr
            100                 105                 110

Tyr Trp Gly Ile Ile Leu Leu Ala Asn Pro Gln Phe Ile Ser
        115                 120                 125

<210> SEQ ID NO 63
<211> LENGTH: 192
<212> TYPE: PRT
<213> ORGANISM: Artificial Sequence
<220> FEATURE:
<223> OTHER INFORMATION: Synthetic polypeptide

<400> SEQUENCE: 63

Arg Ala Gln Gly Glu Ala Cys Val Gln Phe Gln Ala Leu Lys Gly Gln
```

```
1               5                   10                  15
Glu Phe Ala Pro Ser His Gln Gln Val Tyr Ala Pro Leu Arg Ala Asp
            20                  25                  30

Gly Asp Lys Pro Arg Ala His Leu Thr Val Val Arg Gln Thr Pro Thr
            35                  40                  45

Gln His Phe Lys Asn Gln Phe Pro Ala Leu His Trp Glu His Glu Leu
            50                  55                  60

Gly Leu Ala Phe Thr Lys Asn Arg Met Asn Tyr Thr Asn Lys Phe Leu
65                      70                  75                  80

Leu Ile Pro Glu Ser Gly Asp Tyr Phe Ile Tyr Ser Gln Val Thr Phe
                85                  90                  95

Arg Gly Met Thr Ser Glu Cys Ser Glu Ile Arg Gln Ala Gly Arg Pro
                100                 105                 110

Asn Lys Pro Asp Ser Ile Thr Val Val Ile Thr Lys Val Thr Asp Ser
            115                 120                 125

Tyr Pro Glu Pro Thr Gln Leu Leu Met Gly Thr Lys Ser Val Cys Glu
            130                 135                 140

Val Gly Ser Asn Trp Phe Gln Pro Ile Tyr Leu Gly Ala Met Phe Ser
145                 150                 155                 160

Leu Gln Glu Gly Asp Lys Leu Met Val Asn Val Ser Asp Ile Ser Leu
                165                 170                 175

Val Asp Tyr Thr Lys Glu Asp Lys Thr Phe Phe Gly Ala Phe Leu Leu
                180                 185                 190
```

FLT3L-BASED CHIMERIC PROTEINS

PRIORITY

This application is a continuation of U.S. application Ser. No. 16/570,553, filed Sep. 13, 2019. Application Ser. No. 16/570,553 (now U.S. Pat. No. 10,780,121) is a continuation of International Application Serial No. PCT/US2019/048922, filed Aug. 29, 2019. International Application Serial No. PCT/US2019/048922 claims the benefit of, and priority to, U.S. Provisional Application No. 62/724,596, filed Aug. 29, 2018, the content of each of which is herein incorporated by reference in its entirety.

TECHNICAL FIELD

The present invention relates to, inter alia, compositions and methods, including chimeric proteins that find use in the treatment of disease, such as immunotherapies for cancer and autoimmunity.

DESCRIPTION OF THE TEXT FILE SUBMITTED ELECTRONICALLY

This application contains a sequence listing. It has been submitted electronically via EFS-Web as an ASCII text file entitled "SHK-010C2_SequenceListinq_ST25". The sequence listing is 40,938 bytes in size, and was created on Aug. 13, 2020. The sequence listing is hereby incorporated by reference in its entirety.

BACKGROUND

The immune system is central to the body's response to foreign entities that can cause disease and to the body's response to cancer cells. However, many anti-cancer therapeutics do not directly stimulate and/or activate the immune response. Thus, there remains a need to develop therapeutics that, at least, directly stimulate and/or activate a patient's anti-cancer immune response.

SUMMARY

Accordingly, in various aspects, the present invention provides for compositions and methods that are useful for cancer immunotherapy. For instance, the present invention, in part, relates to specific chimeric proteins that provide immune activating or co-stimulatory signals, e.g., to expand and activate dendritic cells.

The present invention relates to chimeric proteins comprising an extracellular domain of FMS like tyrosine kinase 3 ligand (FLT3L) and an extracellular domain of a Type II transmembrane protein. In embodiments, such chimeric proteins have "dual costimulatory" capability, since each domain of the chimeric protein can independently stimulate a single immune system cell or can simultaneously or contemporaneously stimulate a pair of immune system cells.

The extracellular domain of a Type I transmembrane protein, including FLT3L, is located at the protein's amino terminus (see, by way of non-limiting example, FIG. 1A, left protein), whereas the extracellular domain of a Type II transmembrane protein is located at the protein's carboxy terminus (see, by way of non-limiting example, FIG. 1A, right protein). The extracellular domain of Type I transmembrane protein, including FLT3L, contains the functional domains that are responsible for interacting with other binding partners (either ligands or receptors) in the extracellular environment (see, FIG. 1B, left protein) and the extracellular domain of Type II transmembrane protein contains the functional domains that are responsible for interacting with other binding partners (either ligands or receptors) in the extracellular environment (see, FIG. 1B, right protein).

Aspects of the present invention provide a chimeric protein comprising a general structure of: N terminus-(a)-(b)-(c)-C terminus, where (a) is a first domain comprising an extracellular domain of FMS like tyrosine kinase 3 ligand (FLT3L), (b) is a linker adjoining the first domain and the second domain, e.g., the linker comprising at least one cysteine residue capable of forming a disulfide bond and/or comprising a hinge-CH2-CH3 Fc domain, and (c) is a second domain comprising an extracellular domain of a Type II transmembrane protein; wherein the linker connects the first domain and the second domain. See, by way of non-limiting examples, FIG. 1C and FIG. 1D.

Aspects of the present invention provide a chimeric protein comprising a general structure of: N terminus-(a)-(b)-(c)-C terminus, where (a) is a first domain comprising an extracellular domain of FMS like tyrosine kinase 3 ligand (FLT3L), (b) is a linker adjoining the first domain and the second domain, e.g., the linker comprising at least one cysteine residue capable of forming a disulfide bond and/or comprising a hinge-CH2-CH3 Fc domain, and (c) is a second domain comprising an extracellular domain of one of CD40L, OX40L, 4-1BBL, LIGHT, CD30L, TRAIL, FasL, APRIL, BAFF, TWEAK, TL1A, CD70, and GITRL. A chimeric protein of these aspects may have the structure of shown in FIG. 1C or FIG. 1D.

Other aspects of the present invention provide an expression vector comprising a nucleic acid which encodes a chimeric protein as disclosed herein.

Yet other aspects of the present invention provide a host cell comprising the expression vector disclosed herein.

In aspects, the present invention provides a pharmaceutical composition comprising a therapeutically effective amount of the chimeric protein as disclosed herein.

In other aspects, the present invention provides a method of treating cancer or treating an inflammatory disorder due to viral infection. The method comprising a step of administering to a subject in need thereof an effective amount of a pharmaceutical composition as disclosed herein.

In yet other aspects, the present invention provides a method of modulating a patient's immune response. The method comprising a step of administering to a subject in need thereof an effective amount of a pharmaceutical composition as disclosed herein.

Any aspect or embodiment disclosed herein can be combined with any other aspect or embodiment as disclosed herein.

BRIEF DESCRIPTION OF THE DRAWINGS

As shown in FIG. 1C and FIG. 1D, the extracellular domain of a Type I transmembrane protein, e.g., FLT3L, and the extracellular domain of a Type II transmembrane protein are combined into a single chimeric protein. FIG. 1C depicts the linkage of the Type I transmembrane protein and the Type II transmembrane protein by omission of the transmembrane and intracellular domains of each protein, and where the liberated extracellular domains from each protein have been adjoined by a linker sequence. The extracellular domains in this depiction may include the entire amino acid sequence of the Type I protein (e.g., FLT3L) and/or Type II protein which is typically localized outside the cell membrane, or any portion thereof which retains binding to the intended receptor or ligand. Moreover, the chimeric protein comprises sufficient overall flexibility and/or physical distance between domains such that a first extracellular domain (shown at the left end of the chimeric protein in FIG. 1C and FIG. 1D) is sterically capable of binding its receptor/ligand and/or a second extracellular domain (shown at the right end of the chimeric protein in FIG. 1C and FIG. 1D) is sterically capable of binding its receptor/ligand. FIG. 1D depicts adjoined extracellular domains in a linear chimeric protein wherein each extracellular domain of the chimeric protein is facing "outward".

FIG. 9A shows results from the Octet system for measuring affinity with mCD40-his capture (top curve is mFLT3L-Fc-CD40L, middle curve is mCD40L-Fc, and bottom curve is blank). FIG. 9B shows results from the Octet system for measuring affinity with mFLT3-his capture (top curve is mFLT3L-Fc-CD40L, middle curve is mCD40L-Fc, and bottom curve is blank). FIG. 9C shows a summary of the data of FIG. 9A and FIG. 9B. FIG. 9D shows results of an NFkB-mCD40 luciferase reporter assay. FIG. 9E shows a PathHunter U2OS cell-based assay for CD40L signaling (NFkB activity, non-canonical, top curve is mFLT3L-Fc-CD40L, middle curve is mCD40L-Fc, and bottom curve is negative control).

DETAILED DESCRIPTION

Figure 1A:
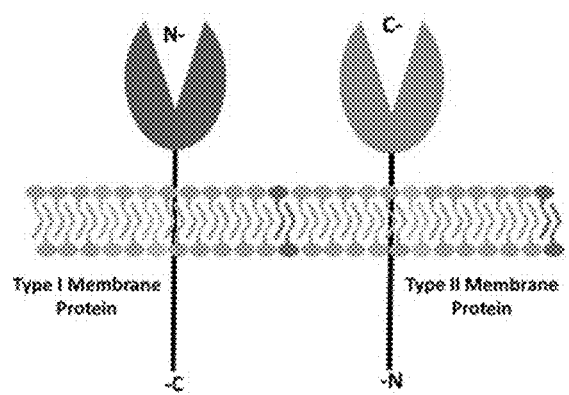
FIG. 1A to FIG. 1D show schematic illustrations of Type I transmembrane proteins (FIG. 1A and FIG. 1B, left proteins) and Type II transmembrane proteins (FIG. 1A and FIG. 1B, right proteins). A Type I transmembrane protein and a Type II transmembrane protein may be engineered such that their transmembrane and intracellular domains are omitted and the transmembrane proteins' extracellular domains are adjoined using a linker sequence to generate a single chimeric protein.

The present invention is based, in part, on the discovery that chimeric proteins can be engineered from the extracellular, or effector, region of FMS like tyrosine kinase 3 ligand (FLT3L) and the extracellular, or effector, region of a Type II transmembrane protein. These, FLT3L-based chimeric proteins provide immune activating or co-stimulatory signals, at least in the treatment of cancer.

In embodiments, the present chimeric proteins increase a number of antigen presenting cells, e.g., dendritic cells. In embodiments, the present chimeric proteins enhance antigen presentation, e.g., tumor antigen presentation.

In embodiments, the present chimeric proteins provide a dual co-stimulatory effect on immune cells, e.g., dendritic cells.

In embodiments, the present chimeric proteins enhance cytokine expression and/or secretion.

In embodiments, the present chimeric proteins provide a contemporaneous effect of activation of antigen presenting cells, e.g., dendritic cells, and expansion of antigen presenting cells, e.g., dendritic cells. For instance, in embodiments, an FLT3-based signal, from the present chimeric proteins, may increase a number of dendritic cells, and this population may be activated via a stimulatory signal (e.g., CD40L, OX40L, GITRL, LIGHT, CD30L, TRAIL, FasL, APRIL, BAFF, TWEAK, and 4-1BBL, from the present chimeric proteins).

Interestingly, the present inventors have demonstrated this dual action of the present chimeric proteins without loss of activity of either side of the present chimeric proteins or, indeed, an increase in signaling activity by the individual sides of the present chimeric proteins. Stated another way, the present chimeric proteins provide contemporaneous modulation of dendritic cells with a single construct in a manner that does not sacrifice activity and even increases it.

The present chimeric proteins provide advantages including, without limitation, ease of use and ease of production. This is because two distinct immunotherapy agents are combined into a single product which may allow for a single manufacturing process instead of two independent manufacturing processes. In addition, administration of a single agent instead of two separate agents allows for easier administration and greater patient compliance.

Additionally, since a chimeric protein may have two immune-modulating domains, it can activate or co-stimulate two distinct immune stimulatory pathways; thus, this dual-action is more likely to provide any anti-tumor effect in a patient and/or to provide an enhanced anti-tumor effect in a patient. Moreover, since the methods operate by multiple distinct pathways, they can be efficacious, at least, in patients who do not respond, respond poorly, or become resistant to treatments that target one of the pathways. Thus, a patient who is a poor responder to treatments acting via one of the two pathways, can receive a therapeutic benefit by targeting multiple pathways.

Chimeric Proteins

The chimeric proteins of the present invention comprise an extracellular domain of FLT3L and an extracellular domain of a Type II transmembrane protein, each of which has immune stimulatory properties upon anti-cancer immune cells. Thus, the chimeric proteins are designed to enhance, increase, and/or stimulate the transmission of an immune stimulatory signal to the anti-cancer immune cell.

FLT3L is a Type I transmembrane protein that functions as a cytokine and as a growth factor which activates and induces proliferation of immune system cells. FLT3L is biologically active in both in its transmembrane form and in its soluble form, which is generated following proteolytic cleavage of the protein's extracellular domain from its transmembrane domain. It has been shown that FLT3L's extracellular domain (residues 1-134) comprises its receptor binding site and is sufficient for bioactivity. See, e.g., Savvides et al., "Flt3 ligand structure and unexpected commonalities of helical bundles and cystine knots" *Nat Struct Biol.* 7(6):486-91 (2000).

Without wishing to be bound by theory, unlike most Type I proteins, FLT3L is immune stimulatory and, when paired with a Type II protein, also typically immune stimulatory, provides a dual co-stimulation immune effect.

Aspects of the present invention provide a chimeric protein comprising a general structure of: N terminus-(a)-(b)-(c)-C terminus, where (a) is a first domain comprising an extracellular domain of FMS like tyrosine kinase 3 ligand (FLT3L), (b) is a linker adjoining the first domain and the second domain, e.g., the linker comprising at least one cysteine residue capable of forming a disulfide bond and/or comprising a hinge-CH2-CH3 Fc domain, and (c) is a second domain comprising an extracellular domain of a Type II transmembrane protein; wherein the linker connects the first domain and the second domain.

In a chimeric protein of the present invention, the first domain may comprise substantially the entire extracellular domain of FLT3L and/or the second domain may comprise substantially the entire extracellular domain of the Type II transmembrane protein.

In a chimeric protein of the present invention, the first domain and/or the second domain may be capable of activating an immune stimulatory signal.

In a chimeric protein of the present invention, the chimeric protein is a recombinant fusion protein, e.g., a single polypeptide having the extracellular domains disclosed herein. For example, in embodiments, the chimeric protein is translated as a single unit in a prokaryotic cell, a eukaryotic cell, or a cell-free expression system.

In embodiments, the present chimeric protein is producible in a mammalian host cell as a secretable and fully functional single polypeptide chain.

In embodiments, chimeric protein refers to a recombinant protein of multiple polypeptides, e.g., multiple extracellular domains disclosed herein, that are combined (via covalent or no-covalent bonding) to yield a single unit, e.g., in vitro (e.g., with one or more synthetic linkers disclosed herein).

In embodiments, the chimeric protein is chemically synthesized as one polypeptide or each domain may be chemically synthesized separately and then combined. In embodiments, a portion of the chimeric protein is translated and a portion is chemically synthesized.

In embodiments, an extracellular domain refers to a portion of a transmembrane protein which is capable of interacting with the extracellular environment. In embodiments, an extracellular domain refers to a portion of a transmembrane protein which is sufficient for binding to a ligand or receptor and is effective in transmitting a signal to a cell. In embodiments, an extracellular domain is the entire amino acid sequence of a transmembrane protein which is normally present at the exterior of a cell or of the cell membrane. In embodiments, an extracellular domain is that portion of an amino acid sequence of a transmembrane protein which is external of a cell or of the cell membrane and is needed for signal transduction and/or ligand binding as may be assayed using methods know in the art (e.g., in vitro ligand binding and/or cellular activation assays).

Transmembrane proteins typically consist of an extracellular domain, one or a series of transmembrane domains, and an intracellular domain. Without wishing to be bound by theory, the extracellular domain of a transmembrane protein is responsible for interacting with a soluble receptor or ligand or membrane-bound receptor or ligand (i.e., a membrane of an adjacent cell). Without wishing to be bound by theory, the trans-membrane domain(s) is responsible for localizing the transmembrane protein to the plasma membrane. Without wishing to be bound by theory, the intracellular domain of a transmembrane protein is responsible for coordinating interactions with cellular signaling molecules to coordinate intracellular responses with the extracellular environment (or visa-versa).

Figure 1B:
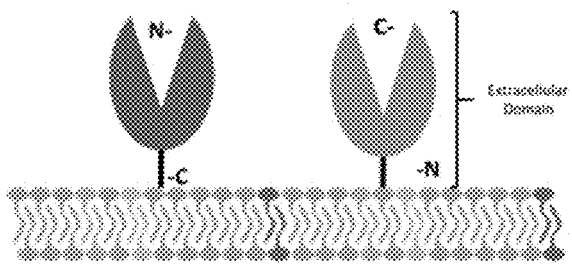

There are generally two types of single-pass transmembrane proteins: Type I transmembrane proteins which have an extracellular amino terminus and an intracellular carboxy terminus (see, FIG. 1A, left protein) and Type II transmembrane proteins which have an extracellular carboxy terminus and an intracellular amino terminus (see, FIG. 1A, right protein). Type I and Type II transmembrane proteins can be either receptors or ligands. For Type I transmembrane proteins, the amino terminus of the protein faces outside the cell, and therefore contains the functional domains that are responsible for interacting with other binding partners (either ligands or receptors) in the extracellular environment (see, FIG. 1B, left protein). For Type II transmembrane proteins, the carboxy terminus of the protein faces outside the cell, and therefore contains the functional domains that are responsible for interacting with other binding partners (either ligands or receptors) in the extracellular environment (see, FIG. 1B, right protein). Thus, these two types of transmembrane proteins have opposite orientations to each other relative to the cell membrane.

Figure 1C:
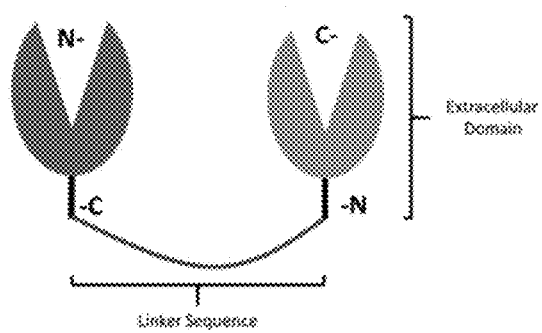
Figure 1D:
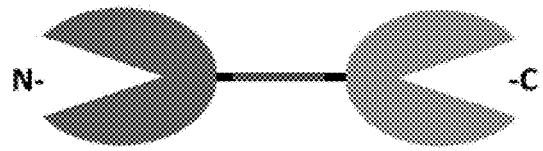
Figure 2:
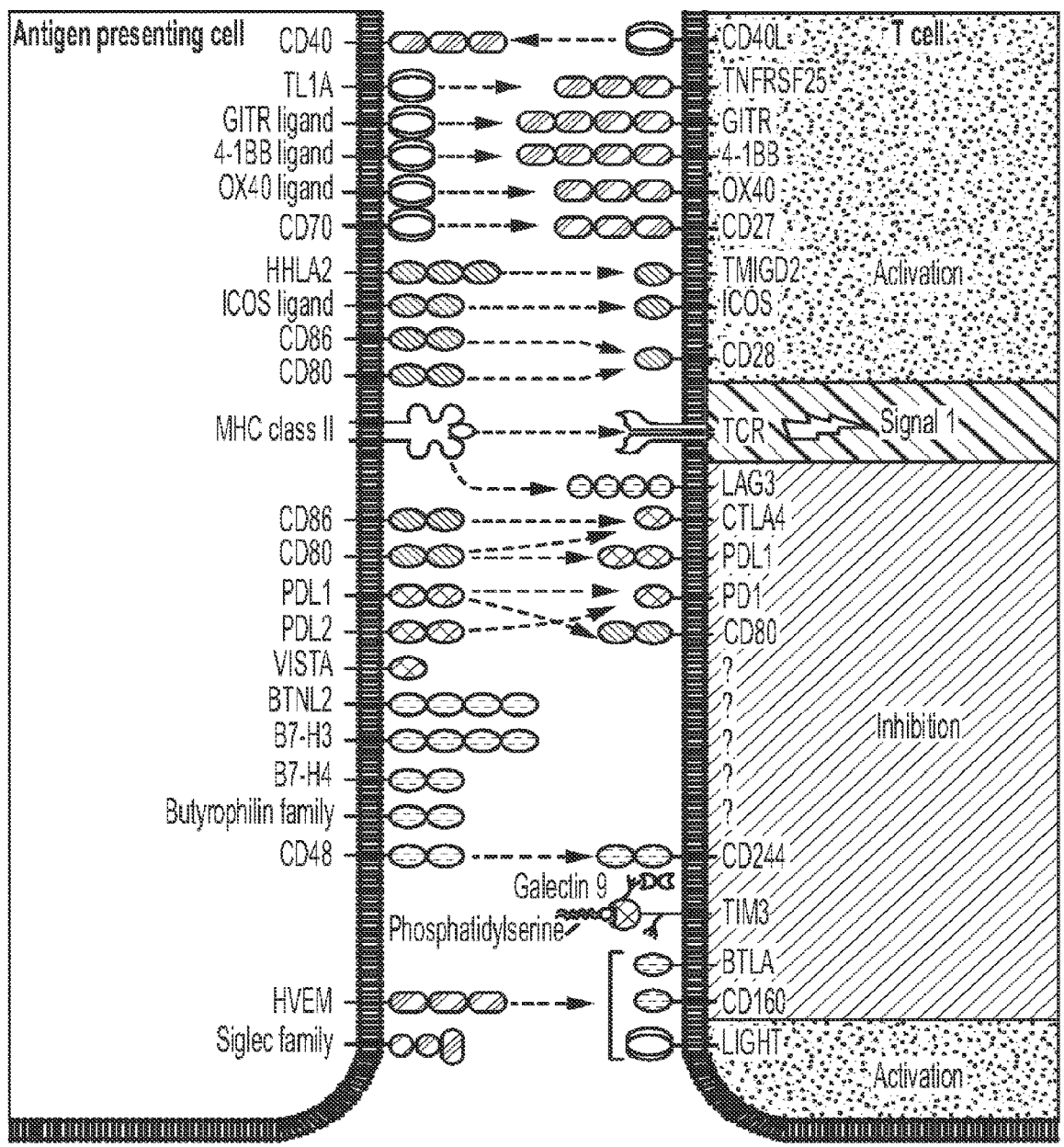
FIG. 2 shows immune inhibitory and immune stimulatory signaling proteins and interactions that are relevant to the present invention (from Mahoney, *Nature Reviews Drug Discovery* 2015:14; 561-585).

Chimeric proteins of the present invention comprise an extracellular domain of FLT3L and an extracellular domain of a Type II transmembrane protein. Thus, a chimeric protein of the present invention comprises, at least, a first domain comprising the extracellular domain of FLT3L, which is connected—directly or via a linker—to a second domain comprising the extracellular domain of a Type II transmembrane protein. As illustrated in FIG. 1C and FIG. 1D, when the domains are linked in an amino-terminal to carboxy-terminal orientation, the first domain is located on the "left" side of the chimeric protein and is "outward facing" and the second domain is located on "right" side of the chimeric protein and is "outward facing".

Other configurations of first and second domains are envisioned, e.g., the first domain is outward facing and the second domain is inward facing, the first domain is inward facing and the second domain is outward facing, and the first and second domains are both inward facing. When both domains are "inward facing", the chimeric protein would have an amino-terminal to carboxy-terminal configuration comprising an extracellular domain of a Type II transmembrane protein, a linker, and an extracellular domain of FLT3L. In such configurations, it may be necessary for the chimeric protein to include extra "slack", as described elsewhere herein, to permit binding of the chimeric protein to one or both of its receptors/ligands.

Constructs could be produced by cloning the nucleic acids encoding the three fragments (the extracellular domain of FLT3L, followed by a linker sequence, followed by the extracellular domain of a Type II transmembrane protein) into a vector (plasmid, viral or other) wherein the amino terminus of the complete sequence corresponded to the 'left' side of the molecule containing the extracellular domain of FLT3L and the carboxy terminus of the complete sequence corresponded to the 'right' side of the molecule containing the Type II transmembrane protein. In embodiments of chimeric proteins having one of the other configurations, as described above, a construct would comprise three nucleic acids such that the translated chimeric protein produced would have the desired configuration, e.g., a dual inward-facing chimeric protein. Accordingly, in embodiments, the present chimeric proteins are engineered as such.

Chimeric proteins of the present invention have a first domain which is sterically capable of binding its ligand/receptor and/or a second domain which is sterically capable of binding its ligand/receptor. This means that there is sufficient overall flexibility in the chimeric protein and/or physical distance between an extracellular domain (or portion thereof) and the rest of the chimeric protein such that the ligand/receptor binding domain of the extracellular domain is not sterically hindered from binding its ligand/receptor. This flexibility and/or physical distance (which is herein referred to as "slack") may be normally present in the extracellular domain(s), normally present in the linker, and/or normally present in the chimeric protein (as a whole). Alternately, or additionally, the chimeric protein may be modified by including one or more additional amino acid sequences (e.g., the joining linkers described below) or synthetic linkers (e.g., a polyethylene glycol (PEG) linker) which provide additional slack needed to avoid steric hindrance.

In embodiments, the chimeric protein of the present invention comprises an extracellular domain of one or more of the immune-modulating agents described in Mahoney, *Nature Reviews Drug Discovery* 2015:14; 561-585, the entire contents of which are hereby incorporated by reference.

In embodiments, the chimeric proteins of the present invention comprise variants of the extracellular domain of FLT3L. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known amino acid sequence of FLT3L, e.g., human FLT3L.

One of ordinary skill may select variants of the known amino acid sequence of FLT3L by consulting the literature, e.g., Zorn, et al. (2015) "Crystal Structure of the FLT3 Kinase Domain Bound to the Inhibitor Quizartinib (AC220)." PLoS ONE 10(4): e0121177, and Graddis, et al. "Structure-Function Analysis of FLT3 Ligand-FLT3 Receptor Interactions Using a Rapid Functional Screen" The Journal of Biological Chemistry 273, 17626-17633, each of which is incorporated by reference in its entirety.

In embodiments, the extracellular domain of human FLT3L comprises the following amino acid sequence:

(SEQ ID NO: 57)
TQDCSFQHSPISSDFAVKIRELSDYLLQDYPVTVASNLQDEELCGGLWR

LVLAQRWMERLKTVAGSKMQGLLERVNTEIHFVTKCAFQPPPSCLRFVQ

TNISRLLQETSEQLVALKPWITRQNFSRCLELQCQPDSSTLPPPWSPRP

LEATAPTAPQP;

In embodiments, the chimeric proteins of the present invention comprise variants of the extracellular domain of FLT3L. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known amino acid sequence of SEQ ID NO: 57.

In embodiments, a variant of the extracellular domain of FLT3L comprises an amino acid sequence that is at least 95% identical to the amino acid sequence of SEQ ID NO: 57.

In embodiments, the present chimeric proteins increase a number of antigen presenting cells, e.g., dendritic cells. In embodiments, the present chimeric proteins increase a number of activated dendritic cells, e.g., CD11c+ and/or CD103+ dendritic cells.

In embodiments, the present chimeric proteins enhance antigen presentation, e.g., tumor antigen presentation, e.g., by dendritic cells, e.g., by activated dendritic cells, e.g., CD11c+ and/or CD103+ dendritic cells.

In embodiments, the present chimeric proteins provide a dual co-stimulatory effect on immune cells, e.g., antigen presenting cells, e.g., dendritic cells.

In embodiments, the present chimeric proteins enhance cytokine expression and/or secretion.

In embodiments, the present chimeric proteins provide a contemporaneous effect of activation of antigen presenting cells, e.g., dendritic cells, and expansion of antigen presenting cells, e.g., dendritic cells. For instance, in embodiments, an FLT3-based signal, from the present chimeric proteins, may increase a number of dendritic cells, and this population may be activated via a stimulatory signal (e.g., CD40L, OX40L, GITRL, LIGHT, CD30L, TRAIL, FasL, APRIL, BAFF, TWEAK, and 4-1BBL, among others from the present chimeric proteins).

In a chimeric protein of the present invention, the Type II transmembrane protein may be selected from the group consisting of: CD40L, 4-1BBL, APRIL, BAFF, BTNL2, CD28, CD30L, CD70, C-type lectin domain (CLEC) family members, FasL, GITRL, LIGHT, LTa, LTa1b2, NKG2A, NKG2C, NKG2D, OX40L, RANKL, TL1A, TNFa, and TRAIL. In embodiments, the Type II transmembrane protein is 4-1BBL. In embodiments, the Type II transmembrane protein is CD40L. In embodiments, the Type II transmembrane protein is CD70. In embodiments, the Type II transmembrane protein is GITRL. In embodiments, the Type II transmembrane protein is OX40L. In embodiments, the Type II transmembrane protein is TL1A.

In embodiments, the chimeric proteins of the present invention comprise variants of the extracellular domain of a Type II transmembrane protein disclosed herein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known amino acid sequence of any of the disclosed extracellular domains of a Type II transmembrane protein as disclosed herein, e.g., a human Type II transmembrane protein.

In embodiments, the chimeric proteins of the present invention comprise variants of the extracellular domain of one of the Type II transmembrane proteins: 4-1BBL, CD40L, CD70, GITRL, OX40L, or TL1A. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known amino acid sequence of any of the extracellular domains of 4-1BBL, CD40L, CD70, GITRL, OX40L, or TL1A, e.g., a human extracellular domain of 4-1BBL, CD40L, CD70, GITRL, OX40L, or TL1A.

In embodiments, a chimeric protein of the present invention comprises the extracellular domain of FLT3L and the extracellular domain of 4-1BBL. In embodiments, a chimeric protein of the present invention comprises a variant of the extracellular domain of FLT3L and a variant of the extracellular domain of 4-1BBL.

In embodiments, a chimeric protein used in methods of the present invention comprises a variant of the extracellular domain of 4-1BBL. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with 4-1BBL, e.g., human 4-1BBL.

One of ordinary skill may select variants of the known amino acid sequence of 4-1BBL by consulting the literature, e.g., Goodwin et al., "Molecular cloning of a ligand for the inducible T cell gene 4-1BB: a member of an emerging family of cytokines with homology to tumor necrosis factor." Eur. J. Immunol. 23 (10), 2631-2641 (1993); Alderson et al., "Molecular and biological characterization of human 4-1BB and its ligand." Eur. J. Immunol. 24 (9), 2219-2227 (1994); and Arch and Thompson "4-1BB and Ox40 are members of a tumor necrosis factor (TNF)-nerve growth factor receptor subfamily that bind TNF receptor-associated factors and activate nuclear factor kappaB." Mol. Cell. Biol. 18 (1), 558-565 (1998), and Gilbreth et al. Crystal structure of the human 4-1BB/4-1BBL complex J Biol Chem. 2018 Jun. 22; 293(25):9880-9891, each of which is incorporated by reference in its entirety, which is incorporated by reference in its entirety.

In embodiments, the extracellular domain of human 4-1BBL comprises the following amino acid sequence:

(SEQ ID NO: 58)
ACPWAVSGARASPGSAASPRLREGPELSPDDPAGLLDLRQGMFAQLVAQ

NVLLIDGPLSWYSDPGLAGVSLIGGLSYKEDTKELWAKAGVYYVFFQLE

LRRVVAGEGSGSVSLALHLQPLRSAAGAAALALTVDLPPASSEARNSAF

GFQGRLLHLSAGQRLGVHLHTEARARHAWQLTQGATVLGLFRVTPEIPA

GLPSPRSE:

In embodiments, a chimeric protein used in methods of the present invention comprises a variant of the extracellular domain of 4-1BBL. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 58.

In embodiments, a variant of the extracellular domain of 4-1BBL comprises an amino acid sequence that is at least 95% identical to the amino acid sequence of SEQ ID NO: 58.

In embodiments, a chimeric protein of the present invention comprises the extracellular domain of FLT3L and the extracellular domain of CD40L. In embodiments, a chimeric protein of the present invention comprises a variant of the extracellular domain of FLT3L and a variant of the extracellular domain of CD40L.

In embodiments, a chimeric protein used in methods of the present invention comprises a variant of the extracellular domain of CD40L. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with CD40L, e.g., human CD40L.

One of ordinary skill may select variants of the known amino acid sequence of CD40L by consulting the literature, e.g., An, et al. Crystallographic and Mutational Analysis of the CD40-CD154 Complex and Its Implications for Receptor Activation, The Journal of Biological Chemistry 286, 11226-11235, which is incorporated by reference in its entirety.

In embodiments, the extracellular domain of human CD40L comprises the following amino acid sequence:

(SEQ ID NO: 59)
HRRLDKIEDERNLHEDFVFMKTIQRCNTGERSLSLLNCEEIKSQFEGFV

KDIMLNKEETKKENSFEMQKGDQNPQIAAHVISEASSKTTSVLQWAEKG

YYTMSNNLVTLENGKQLTVKRQGLYYIYAQVIFCSNREASSQAPFIASL

CLKSPGRFERILLRAANTHSSAKPCGQQS1HLGGVFELQPGASVFVNVI

DPSQVSHGTGFTSFGLLKL:

In embodiments, a chimeric protein used in methods of the present invention comprises a variant of the extracellular domain of CD40L. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 59.

In embodiments, a variant of the extracellular domain of CD40L comprises an amino acid sequence that is at least 95% identical to the amino acid sequence of SEQ ID NO: 59.

In embodiments, a chimeric protein of the present invention comprises the extracellular domain of FLT3L and the extracellular domain of CD70. In embodiments, a chimeric protein of the present invention comprises a variant of the extracellular domain of FLT3L and a variant of the extracellular domain of 70.

In embodiments, a chimeric protein used in methods of the present invention comprises a variant of the extracellular domain of CD70. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with CD70, e.g., human CD70.

One of ordinary skill may select variants of the known amino acid sequence of CD70 by consulting the literature, e.g., Goodwin et al., "Molecular and biological characterization of a ligand for CD27 defines a new family of cytokines with homology to tumor necrosis factor." Cell 73 (3), 447-456 (1993), Bowman et al., "The cloning of CD70 and its identification as the ligand for CD27" J. Immunol. 152 (4), 1756-1761 (1994), Hintzen et al., "CD70 represents the human ligand for CD27" Int. Immunol. 6 (3), 477-480 (1994), and Hintzen et al., "Characterization of the human CD27 ligand, a novel member of the TNF gene family" J. Immunol. 152 (4), 1762-1773 (1994), each of which is incorporated by reference in its entirety.

In embodiments, the extracellular domain of human CD70 comprises the following amino acid sequence:

```
                                        (SEQ ID NO: 60)
QRFAQAQQQLPLESLGWDVAELQLNHTGPQQDPRLYWQGGPALGRSFLH

GPELDKGQLRIHRDGIYMVHIQVTLAICSSTTASRHHPTTLAVGICSPA

SRSISLLRLSFHQGCTIASQRLTPLARGDTLCTNLTGTLLPSRNTDETF

FGVQWVRP.
```

In embodiments, a chimeric protein used in methods of the present invention comprises a variant of the extracellular domain of CD70. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 60.

In embodiments, a chimeric protein of the present invention comprises the extracellular domain of FLT3L and the extracellular domain of OX40L. In embodiments, a chimeric protein of the present invention comprises a variant of the extracellular domain of FLT3L and a variant of the extracellular domain of OX40L.

In embodiments, a chimeric protein used in methods of the present invention comprises a variant of the extracellular domain of OX40L. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with OX40L, e.g., human OX40L.

One of ordinary skill may select variants of the known amino acid sequence of OX40L by consulting the literature, e.g., CROFT, et al., "The Significance of OX40 and OX40L to T cell Biology and Immune Disease," Immunol Rev., 229(1), PP. 173-191, 2009 and BAUM, et al., "Molecular characterization of murine and human OX40/OX40 ligand systems: identification of a human OX40 ligand as the HTLV-1-regulated protein gp34," The EMBO Journal, Vol. 13, No. 77, PP. 3992-4001, 1994, each of which is incorporated by reference in its entirety.

In embodiments, the extracellular domain of human OX40L comprises the following amino acid sequence:

```
                                        (SEQ ID NO: 61)
QVSHRYPRIQSIKVQFTEYKKEKGFILTSQKEDEIMKVQNNSVIINCDG

FYLISLKGYFSQEVNISLHYQKDEEPLFQLKKVRSVNSLMVASLTYKDK

VYLNVTTDNTSLDDFHVNGGELILIHQNPGEFCVL.
```

In embodiments, a chimeric protein used in methods of the present invention comprises a variant of the extracellular domain of OX40L. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 61.

In embodiments, a variant of the extracellular domain of OX40L comprises an amino acid sequence that is at least 95% identical to the amino acid sequence of SEQ ID NO: 61.

In embodiments, a chimeric protein of the present invention comprises the extracellular domain of FLT3L and the extracellular domain of GITRL. In embodiments, a chimeric protein of the present invention comprises a variant of the extracellular domain of FLT3L and a variant of the extracellular domain of GITRL.

In embodiments, a chimeric protein used in methods of the present invention comprises a variant of the extracellular domain of GITRL. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with GITRL, e.g., human GITRL.

One of ordinary skill may select variants of the known amino acid sequence of GITRL by consulting the literature, e.g., Chattopadhyay et al. "Evolution of GITRL immune function: Murine GITRL exhibits unique structural and biochemical properties within the TNF superfamily." PNAS, Volume 105, Issue 2, 2008, pp. 635-640 and Zjou, et al. "Structural basis for ligand-mediated mouse GITR activation Structural basis for ligand-mediated mouse GITR activation." PNAS Jan. 15, 2008. 105 (2) 641-645 each of which is incorporated by reference in its entirety.

In embodiments, the extracellular domain of human GITRL comprises the following amino acid sequence:

```
                                      (SEQ ID NO: 62)
ETAKEPCMAKFGPLPSKWQMASSEPPCVNKVSDWKLEILQNGLYLIYGQ
VAPNANYNDVAPFEVRLYKNKDMIQTLTNKSKIQNVGGTYELHVGDTID
LIFNSEHQVLKNNTYWGIILLANPQFIS:
```

In embodiments, a chimeric protein used in methods of the present invention comprises a variant of the extracellular domain of GITRL. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 62.

In embodiments, a variant of the extracellular domain of GITRL comprises an amino acid sequence that is at least 95% identical to the amino acid sequence of SEQ ID NO: 62.

In embodiments, a chimeric protein of the present invention comprises the extracellular domain of FLT3L and the extracellular domain of TL1A. In embodiments, a chimeric protein of the present invention comprises a variant of the extracellular domain of FLT3L and a variant of the extracellular domain of TL1A.

In embodiments, a chimeric protein used in methods of the present invention comprises a variant of the extracellular domain of T1LA. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with TL1A, e.g., human TL1A.

One of ordinary skill may select variants of the known amino acid sequence of TL1A by consulting the literature, e.g., Tan et al., "Characterization of a novel TNF-like ligand and recently described TNF ligand and TNF receptor superfamily genes and their constitutive and inducible expression in hematopoietic and non-hematopoietic cells" Gene 204 (1-2), 35-46 (1997), and Zhai et al., "VEGI, a novel cytokine of the tumor necrosis factor family, is an angiogenesis inhibitor that suppresses the growth of colon carcinomas in vivo." FASEB J. 13 (1), 181-189 (1999), each of which is incorporated by reference in its entirety.

In embodiments, the extracellular domain of human TL1A comprises the following amino acid sequence:

```
                                      (SEQ ID NO: 63)
RAQGEACVQFQALKGQEFAPSHQQVYAPLRADGDKPRAHLTWRQTPTQH

FKNQFPALHWEHELGLAFTKNRMNYTNKFLLIPESGDYFIYSQVTFRGM

TSECSEIRQAGRPNKPDSITWITKVTDSYPEPTQLLMGTKSVCEVGSNW

FQPIYLGAMFSLQEGDKLMVNVSDISLVDYTKEDKTFFGAFLL:
```

In embodiments, a chimeric protein used in methods of the present invention comprises a variant of the extracellular domain of TL1A. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 63.

In any herein-disclosed aspect and embodiment, the chimeric protein may comprise an amino acid sequence having one or more amino acid mutations relative to any of the protein sequences disclosed herein. In embodiments, the one or more amino acid mutations may be independently selected from substitutions, insertions, deletions, and truncations.

In embodiments, the amino acid mutations are amino acid substitutions, and may include conservative and/or non-conservative substitutions. "Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe. As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. As used herein, "non-conservative substitutions" are defined as exchanges of an amino acid by another amino acid listed in a different group of the six standard amino acid groups (1) to (6) shown above.

In embodiments, the substitutions may also include non-classical amino acids (e.g., selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Mutations may also be made to the nucleotide sequences of the chimeric proteins by reference to the genetic code, including taking into account codon degeneracy.

In embodiments, a chimeric protein is capable of binding murine ligand(s)/receptor(s).

In embodiments, a chimeric protein is capable of binding human ligand(s)/receptor(s).

In embodiments, each extracellular domain (or variant thereof) of the chimeric protein binds to its cognate receptor or ligand with a $K_D$ of about 1 nM to about 5 nM, for example, about 1 nM, about 1.5 nM, about 2 nM, about 2.5 nM, about 3 nM, about 3.5 nM, about 4 nM, about 4.5 nM, or about 5 nM. In embodiments, the chimeric protein binds to a cognate receptor or ligand with a $K_D$ of about 5 nM to about 15 nM, for example, about 5 nM, about 5.5 nM, about 6 nM, about 6.5 nM, about 7 nM, about 7.5 nM, about 8 nM, about 8.5 nM, about 9 nM, about 9.5 nM, about 10 nM, about 10.5 nM, about 11 nM, about 11.5 nM, about 12 nM, about 12.5 nM, about 13 nM, about 13.5 nM, about 14 nM, about 14.5 nM, or about 15 nM.

In embodiments, each extracellular domain (or variant thereof) of the chimeric protein binds to its cognate receptor or ligand with a $K_D$ of less than about 1 μM, about 900 nM, about 800 nM, about 700 nM, about 600 nM, about 500 nM, about 400 nM, about 300 nM, about 200 nM, about 150 nM, about 130 nM, about 100 nM, about 90 nM, about 80 nM, about 70 nM, about 60 nM, about 55 nM, about 50 nM, about 45 nM, about 40 nM, about 35 nM, about 30 nM, about 25 nM, about 20 nM, about 15 nM, about 10 nM, or about 5 nM, or about 1 nM (as measured, for example, by surface plasmon resonance or biolayer interferometry). In embodiments, the chimeric protein binds to human CSF1 with a $K_D$ of less than about 1 nM, about 900 pM, about 800 pM, about 700 pM, about 600 pM, about 500 pM, about 400 pM, about 300 pM, about 200 pM, about 100 pM, about 90 pM, about 80 pM, about 70 pM, about 60 pM about 55 pM about 50 pM about 45 pM, about 40 pM, about 35 pM, about 30 pM, about 25 pM, about 20 pM, about 15 pM, or about 10 pM, or about 1 pM (as measured, for example, by surface plasmon resonance or biolayer interferometry).

As used herein, a variant of an extracellular domain is capable of binding the receptor/ligand of a native extracellular domain. For example, a variant may include one or more mutations in an extracellular domain which do not affect its binding affinity to its receptor/ligand; alternately, the one or more mutations in an extracellular domain may improve binding affinity for the receptor/ligand; or the one or more mutations in an extracellular domain may reduce binding affinity for the receptor/ligand, yet not eliminate binding altogether. In embodiments, the one or more mutations are located outside the binding pocket where the extracellular domain interacts with its receptor/ligand. In embodiments, the one or more mutations are located inside the binding pocket where the extracellular domain interacts with its receptor/ligand, as long as the mutations do not eliminate binding altogether. Based on the skilled artisan's knowledge and the knowledge in the art regarding receptor-ligand binding, s/he would know which mutations would permit binding and which would eliminate binding.

In embodiments, the chimeric protein exhibits enhanced stability, high-avidity binding characteristics, prolonged off-rate for target binding and protein half-life relative to single-domain fusion protein or antibody controls.

A chimeric protein of the present invention may comprise more than two extracellular domains. For example, the chimeric protein may comprise three, four, five, six, seven, eight, nine, ten, or more extracellular domains. A second extracellular domain may be separated from a third extracellular domain via a linker, as disclosed herein. Alternately, a second extracellular domain may be directly linked (e.g., via a peptide bond) to a third extracellular domain. In embodiments, a chimeric protein includes extracellular domains that are directly linked and extracellular domains that are indirectly linked via a linker, as disclosed herein.

Linkers

In embodiments, the chimeric protein comprises a linker.

In embodiments, the linker comprising at least one cysteine residue capable of forming a disulfide bond. The at least one cysteine residue is capable of forming a disulfide bond between a pair (or more) of chimeric proteins. Without wishing to be bound by theory, such disulfide bond forming is responsible for maintaining a useful multimeric state of chimeric proteins. This allows for efficient production of the chimeric proteins; it allows for desired activity in vitro and in vivo.

In a chimeric protein of the present invention, the linker is a polypeptide selected from a flexible amino acid sequence, an IgG hinge region, or an antibody sequence.

In embodiments, the linker is derived from naturally-occurring multi-domain proteins or is an empirical linker as described, for example, in Chichili et al, (2013), Protein Sci. 22(2):153-167, Chen et al, (2013), Adv Drug Deliv Rev. 65(10):1357-1369, the entire contents of which are hereby incorporated by reference. In embodiments, the linker may be designed using linker designing databases and computer programs such as those described in Chen et al, (2013), Adv Drug Deliv Rev. 65(10):1357-1369 and Crasto et. al., (2000), Protein Eng. 13(5):309-312, the entire contents of which are hereby incorporated by reference.

In embodiments, the linker comprises a polypeptide. In embodiments, the polypeptide is less than about 500 amino acids long, about 450 amino acids long, about 400 amino acids long, about 350 amino acids long, about 300 amino acids long, about 250 amino acids long, about 200 amino acids long, about 150 amino acids long, or about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long.

In embodiments, the linker is flexible.

In embodiments, the linker is rigid.

In embodiments, the linker is substantially comprised of glycine and serine residues (e.g., about 30%, or about 40%, or about 50%, or about 60%, or about 70%, or about 80%, or about 90%, or about 95%, or about 97%, or about 98%, or about 99%, or about 100% glycines and serines).

In embodiments, the linker comprises a hinge region of an antibody (e.g., of IgG, IgA, IgD, and IgE, inclusive of subclasses (e.g., IgG1, IgG2, IgG3, and IgG4, and IgA1, and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2. In embodiments, the linker may be derived from human IgG4 and contain one or more mutations to enhance dimerization (including S228P) or FcRn binding.

According to crystallographic studies, the immunoglobulin hinge region can be further subdivided functionally into three regions: the upper hinge region, the core region, and the lower hinge region. See Shin et al., 1992 Immunological Reviews 130:87. The upper hinge region includes amino acids from the carboxyl end of CH1 to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of wild-type human IgG1 contains the sequence CPPC (SEQ ID NO: 24) which, when dimerized by disulfide bond formation, results in a cyclic octapeptide believed to act as a pivot, thus conferring flexibility. In embodiments, the present linker comprises, one, or two, or three of the upper hinge region, the core region, and the lower hinge region of any antibody (e.g., of IgG, IgA, IgD, and IgE, inclusive of subclasses (e.g., IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In embodiments, the linker of the present invention comprises one or more glycosylation sites.

In embodiments, the linker comprises an Fc domain of an antibody (e.g., of IgG, IgA, IgD, and IgE, inclusive of subclasses (e.g., IgG1, IgG2, IgG3, and IgG4, and IgA1 and IgA2)).

In a chimeric protein of the present invention, the linker comprises a hinge-CH2-CH3 Fc domain derived from IgG4. In embodiments, the linker comprises a hinge-CH2-CH3 Fc domain derived from a human IgG4. In embodiments, the linker comprises an amino acid sequence that is at least 95% identical to the amino acid sequence of any one of SEQ ID NO: 1 to SEQ ID NO: 3, e.g., at least 95% identical to the amino acid sequence of SEQ ID NO: 2. In embodiments, the linker comprises one or more joining linkers, such joining linkers independently selected from SEQ ID NOs: 4-50 (or a variant thereof). In embodiments, the linker comprises two or more joining linkers each joining linker independently selected from SEQ ID NOs: 4-50 (or a variant thereof); wherein one joining linker is N terminal to the hinge-CH2-CH3 Fc domain and another joining linker is C terminal to the hinge-CH2-CH3 Fc domain.

In embodiments, the linker comprises a hinge-CH2-CH3 Fc domain derived from a human IgG1 antibody. In embodiments, the Fc domain exhibits increased affinity for and enhanced binding to the neonatal Fc receptor (FcRn). In embodiments, the Fc domain includes one or more mutations that increases the affinity and enhances binding to FcRn. Without wishing to be bound by theory, it is believed that increased affinity and enhanced binding to FcRn increases the in vivo half-life of the present chimeric proteins.

In embodiments, the Fc domain in a linker contains one or more amino acid substitutions at amino acid residue 250, 252, 254, 256, 308, 309, 311, 416, 428, 433 or 434 (in accordance with Kabat numbering, as in as in Kabat, et al., Sequences of Proteins of Immunological Interest, 5th Ed. Public Health Service, National Institutes of Health, Bethesda, Md. (1991) expressly incorporated herein by reference), or equivalents thereof. In embodiments, the amino acid substitution at amino acid residue 250 is a substitution with glutamine. In embodiments, the amino acid substitution at amino acid residue 252 is a substitution with tyrosine, phenylalanine, tryptophan or threonine. In embodiments, the amino acid substitution at amino acid residue 254 is a substitution with threonine. In embodiments, the amino acid substitution at amino acid residue 256 is a substitution with serine, arginine, glutamine, glutamic acid, aspartic acid, or threonine. In embodiments, the amino acid substitution at amino acid residue 308 is a substitution with threonine. In embodiments, the amino acid substitution at amino acid residue 309 is a substitution with proline. In embodiments, the amino acid substitution at amino acid residue 311 is a substitution with serine. In embodiments, the amino acid substitution at amino acid residue 385 is a substitution with arginine, aspartic acid, serine, threonine, histidine, lysine, alanine or glycine. In embodiments, the amino acid substitution at amino acid residue 386 is a substitution with threonine, proline, aspartic acid, serine, lysine, arginine, isoleucine, or methionine. In embodiments, the amino acid substitution at amino acid residue 387 is a substitution with arginine, proline, histidine, serine, threonine, or alanine. In embodiments, the amino acid substitution at amino acid residue 389 is a substitution with proline, serine or asparagine. In embodiments, the amino acid substitution at amino acid residue 416 is a substitution with serine. In embodiments, the amino acid substitution at amino acid residue 428 is a substitution with leucine. In embodiments, the amino acid substitution at amino acid residue 433 is a substitution with arginine, serine, isoleucine, proline, or glutamine. In embodiments, the amino acid substitution at amino acid residue 434 is a substitution with histidine, phenylalanine, or tyrosine.

In embodiments, the Fc domain linker (e.g., comprising an IgG constant region) comprises one or more mutations such as substitutions at amino acid residue 252, 254, 256, 433, 434, or 436 (in accordance with Kabat numbering, as in as in Kabat, et al., Sequences of Proteins of Immunological Interest, 5th Ed. Public Health Service, National Institutes of Health, Bethesda, Md. (1991) expressly incorporated herein by reference). In embodiments, the IgG constant region includes a triple M252Y/S254T/T256E mutation or YTE mutation. In embodiments, the IgG constant region includes a triple H433K/N434F/Y436H mutation or KFH mutation. In embodiments, the IgG constant region includes an YTE and KFH mutation in combination.

In embodiments, the linker comprises an IgG constant region that contains one or more mutations at amino acid residues 250, 253, 307, 310, 380, 428, 433, 434, and 435 (in accordance with Kabat numbering, as in as in Kabat, et al., Sequences of Proteins of Immunological Interest, 5th Ed. Public Health Service, National Institutes of Health, Bethesda, Md. (1991) expressly incorporated herein by reference). Illustrative mutations include T250Q, M428L, T307A, E380A, I253A, H310A, M428L, H433K, N434A, N434F, N434S, and H435A. In embodiments, the IgG constant region comprises a M428L/N434S mutation or LS mutation. In embodiments, the IgG constant region comprises a T250Q/M428L mutation or QL mutation. In embodiments, the IgG constant region comprises an N434A mutation. In embodiments, the IgG constant region comprises a T307A/E380A/N434A mutation or AAA mutation. In embodiments, the IgG constant region comprises an I253A/H310A/H435A mutation or IHH mutation. In embodiments, the IgG constant region comprises a H433K/N434F mutation. In embodiments, the IgG constant region comprises a M252Y/S254T/T256E and a H433K/N434F mutation in combination.

Additional exemplary mutations in the IgG constant region are described, for example, in Robbie, et al, Antimicrobial Agents and Chemotherapy (2013), 57(12):6147-6153, Dall'Acqua et al, JBC (2006), 281(33):23514-24, Dall'Acqua et al., Journal of Immunology (2002), 169:5171-80, Ko et al. Nature (2014) 514:642-645, Grevys et al. Journal of Immunology. (2015), 194(11):5497-508, and U.S. Pat. No. 7,083,784, the entire contents of which are hereby incorporated by reference.

An illustrative Fc stabilizing mutant is S228P. Illustrative Fc half-life extending mutants are T250Q, M428L, V308T, L309P, and Q311S and the present linkers may comprise 1, or 2, or 3, or 4, or 5 of these mutants.

In embodiments, the chimeric protein binds to FcRn with high affinity. In embodiments, the chimeric protein may bind to FcRn with a $K_D$ of about 1 nM to about 80 nM. For example, the chimeric protein may bind to FcRn with a $K_D$ of about 1 nM, about 2 nM, about 3 nM, about 4 nM, about 5 nM, about 6 nM, about 7 nM, about 8 nM, about 9 nM, about 10 nM, about 15 nM, about 20 nM, about 25 nM, about 30 nM, about 35 nM, about 40 nM, about 45 nM, about 50 nM, about 55 nM, about 60 nM, about 65 nM, about 70 nM, about 71 nM, about 72 nM, about 73 nM, about 74 nM, about 75 nM, about 76 nM, about 77 nM, about 78 nM, about 79 nM, or about 80 nM. In embodiments, the chimeric protein may bind to FcRn with a $K_D$ of about 9 nM. In embodiments, the chimeric protein does not substantially bind to other Fc receptors (i.e. other than FcRn) with effector function.

In embodiments, the Fc domain in a linker has the amino acid sequence of SEQ ID NO: 1 (see Table 1, below), or at least 90%, or 93%, or 95%, or 97%, or 98%, or 99% identity thereto. In embodiments, mutations are made to SEQ ID NO: 1 to increase stability and/or half-life. For instance, in embodiments, the Fc domain in a linker comprises the amino acid sequence of SEQ ID NO: 2 (see Table 1, below), or at least 90%, or 93%, or 95%, or 97%, or 98%, or 99% identity thereto. For instance, in embodiments, the Fc domain in a linker comprises the amino acid sequence of SEQ ID NO: 3 (see Table 1, below), or at least 90%, or 93%, or 95%, or 97%, or 98%, or 99% identity thereto.

Further, one or more joining linkers may be employed to connect an Fc domain in a linker (e.g., one of SEQ ID NO: 1, SEQ ID NO: 2, SEQ ID NO: 3 or at least 90%, or 93%, or 95%, or 97%, or 98%, or 99% identity thereto) and the extracellular domains. For example, any one of SEQ ID NO: 4, SEQ ID NO: 5, SEQ ID NO: 6, SEQ ID NO: 7, SEQ ID NO: 8, SEQ ID NO: 9, or variants thereof may connect an extracellular domain as disclosed herein and an Fc domain in a linker as disclosed herein. Optionally, any one of SEQ ID NOs: 4 to 50, or variants thereof are located between an extracellular domain as disclosed herein and an Fc domain as disclosed herein.

In embodiments, the present chimeric proteins may comprise variants of the joining linkers disclosed in Table 1, below. For instance, a linker may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the amino acid sequence of any one of SEQ ID NOs: 4 to 50.

In embodiments, the first and second joining linkers may be different or they may be the same.

Without wishing to be bound by theory, including a linker comprising at least a part of an Fc domain in a chimeric protein, helps avoid formation of insoluble and, likely, non-functional protein concatenated oligomers and/or aggregates. This is in part due to the presence of cysteines in the Fc domain which are capable of forming disulfide bonds between chimeric proteins.

In embodiments, a chimeric protein may comprise one or more joining linkers, as disclosed herein, and lack a Fc domain linker, as disclosed herein.

In embodiments, the first and/or second joining linkers are independently selected from the amino acid sequences of SEQ ID NOs: 4 to 50 and are provided in Table 1 below:

TABLE 1

Illustrative linkers (Fc domain linkers and joining linkers)

| SEQ ID NO. | Sequence |
|---|---|
| 1 | APEFLGGPSVFLFPPKPKDILMISRTPEVTCVVVDVSQEDPEVQFNWYVDGVEVHNAKTKPREEQFNSTYRVVSVLTVLHQMAISGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVMHEALHNHYTQKSLSLSLGK |
| 2 | APEFLGGPSVFLFPPKPKDQLMISRTPEVTCVVVDVSQEDPEVQFNWYVDGVEVHNAKTKPREEQFNSTYRVVSVLTTPHSDIAISGKEYKCKVSSKGLPSSEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVLHEALHNHYTQKSLSLSLGK |
| 3 | APEFLGGPSVFLFPPKPKDQLMISRTPEVTCVVVDVSQEDPEVQFNWYVDGVEVHNAKTKPREEQFNSTYRVVSVLTVLHQMAISGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGK |
| 4 | SKYGPPCPSCP |
| 5 | SKYGPPCPPCP |
| 6 | SKYGPP |
| 7 | IEGRMD |
| 8 | GGGVPRDCG |
| 9 | IEGRMDGGGAGGGG |
| 10 | GGGSGGGS |
| 11 | GGGSGGGSGGG |
| 12 | EGKSSGSGSESKST |
| 13 | GGSG |
| 14 | GGSGGGSGGGSG |
| 15 | EAAAKEAAAKEAAAK |
| 16 | EAAAREAAAREAAAREAAAR |
| 17 | GGGGSGGGGSGGGGSAS |
| 18 | GGGGAGGGG |
| 19 | GS or GGS or LE |
| 20 | GSGSGS |
| 21 | GSGSGSGSGS |
| 22 | GGGGSAS |
| 23 | APAPAPAPAPAPAPAPAP |
| 24 | CPPC |

TABLE 1-continued

Illustrative linkers (Fc domain linkers and joining linkers)

| SEQ ID NO. | Sequence |
|---|---|
| 25 | GGGGS |
| 26 | GGGGSGGGGS |
| 27 | GGGGSGGGGSGGGGS |
| 28 | GGGGSGGGGSGGGGSGGGGS |
| 29 | GGGGSGGGGSGGGGSGGGGSGGGGS |
| 30 | GGGGSGGGGSGGGGSGGGGSGGGGSGGGGS |
| 31 | GGGGSGGGGSGGGGSGGGGSGGGGSGGGGSGGGGS |
| 32 | GGGGSGGGGSGGGGSGGGGSGGGGSGGGGSGGGGSGGGGS |
| 33 | GGSGGSGGGGSGGGGS |
| 34 | GGGGGGGG |
| 35 | GGGGGG |
| 36 | EAAAK |
| 37 | EAAAKEAAAK |
| 38 | EAAAKEAAAKEAAAK |
| 39 | AEAAAKEAAAKA |
| 40 | AEAAAKEAAAKEAAAKA |
| 41 | AEAAAKEAAAKEAAAKEAAAKA |
| 42 | AEAAAKEAAAKEAAAKEAAAKEAAAKA |
| 43 | AEAAAKEAAAKEAAAKEAAAKALEAEAAAKEAAAKEAAAKEAAAKA |
| 44 | PAPAP |
| 45 | KESGSVSSEQLAQFRSLD |
| 46 | GSAGSAAGSGEF |
| 47 | GGGSE |
| 48 | GSESG |
| 49 | GSEGS |
| 50 | GEGGSGEGSSGEGSSSEGGGSEGGGSEGGGSEGGS |

In embodiments, the joining linker substantially comprises glycine and serine residues (e.g., about 30%, or about 40%, or about 50%, or about 60%, or about 70%, or about 80%, or about 90%, or about 95%, or about 97%, or about 98%, or about 99%, or about 100% glycines and serines). For example, in embodiments, the joining linker is $(Gly_4Ser)_n$, where n is from about 1 to about 8, e.g., 1, 2, 3, 4, 5, 6, 7, or 8 (SEQ ID NO: 25 to SEQ ID NO: 32, respectively). In embodiments, the joining linker sequence is GGSGGSGGGGSGGGGS (SEQ ID NO: 33). Additional illustrative joining linkers include, but are not limited to, linkers having the sequence LE, $(EAAAK)_n$ (n=1-3) (SEQ ID NO: 36 to SEQ ID NO: 38), $A(EAAAK)_nA$ (n=2-5) (SEQ ID NO: 39 to SEQ ID NO: 42), $A(EAAAK)_4ALEA(EAAAK)_4A$ (SEQ ID NO: 43), PAPAP (SEQ ID NO: 44), KESGSVSSEQLAQFRSLD (SEQ ID NO: 45), GSAGSAAGSGEF (SEQ ID NO: 46), and $(XP)_n$, with X designating any amino acid, e.g., Ala, Lys, or Glu. In embodiments, the joining linker is GGS. In embodiments, a joining linker has the sequence $(Gly)_n$ where n is any number from 1 to 100, for example: $(Gly)_8$ (SEQ ID NO: 34) and $(Gly)_6$ (SEQ ID NO: 35).

In embodiments, the joining linker is one or more of GGGSE (SEQ ID NO: 47), GSESG (SEQ ID NO: 48), GSEGS (SEQ ID NO: 49), GEGGSGEGSSGEGSSSEGGGSEGGGSEGGGSEGGS (SEQ ID NO: 50), and a joining linker of randomly placed G, S, and E every 4 amino acid intervals.

In embodiments, where a chimeric protein comprises an extracellular domain (ECD) of FLT3L, one joining linker preceding an Fc domain, a second joining linker following the Fc domain, and an ECD of a Type II transmembrane protein, the chimeric protein may comprise the following structure:

ECD of FLT3L-Joining Linker 1-Fc Domain-Joining Linker 2-ECD of Type II protein

The combination of a first joining linker, an Fc Domain linker, and a second joining linker is referred to herein as a "modular linker". In embodiments, a chimeric protein comprises a modular linker as shown in Table 2:

TABLE 2

Illustrative modular linkers

| Joining Linker 1 | Fc | Joining Linker 2 | Modular Linker = Joining Linker 1 + Fc + Joining Linker 2 |
|---|---|---|---|
| SKYGPPCPSCP (SEQ ID NO: 4) | APEFLGGPSVFLFPPKPKDTLMISRTPEVTCVVVDVSQEDPEVQFNWYVDGVEVHNAKTKPREEQFNSTYRWSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVMHEALHNHYTQKSLSLSLGK (SEQ ID NO: 1) | IEGRMD (SEQ ID NO: 7) | SKYGPPCPSCPAPEFLGGPSVFLFPPKPKDTLMISRTPEVTCVVVDVSQEDPEVQFNWYVDGVEVHNAKTKPREEQFNSTYRWSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVMHEALHNHYTQKSLSLSLGKIEGRMD (SEQ ID NO: 51) |
| SKYGPPCPSCP (SEQ ID NO: 4) | APEFLGGPSVFLFPPKPKDQLMISRTPEVTCVVVDVSQEDPEVQFNWYVDGVEVHNAKTKPREEQFNSTYRWSVLTTPHSDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVLHEALHNHYTQKSLSLSLGK (SEQ ID NO: 2) | IEGRMD (SEQ ID NO: 7) | SKYGPPCPSCPAPEFLGGPSVFLFPPKPKDQLMISRTPEVTCVVVDVSQEDPEVQFNWYVDGVEVHNAKTKPREEQFNSTYRWSVLTTPHSDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVLHEALHNHYTQKSLSLSLGKIEGRMD (SEQ ID NO: 52) |
| SKYGPPCPSCP (SEQ ID NO: 4) | APEFLGGPSVFLFPPKPKDQLMISRTPEVTCVVVDVSQEDPEVQFNWYVDGVEVHNAKTKPREEQFNSTYRWSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGK (SEQ ID NO: 3) | IEGRMD (SEQ ID NO: 7) | SKYGPPCPSCPAPEFLGGPSVFLFPPKPKDQLMISRTPEVTCVVVDVSQEDPEVQFNWYVDGVEVHNAKTKPREEQFNSTYRWSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGKIEGRMD (SEQ ID NO: 53) |
| SKYGPPCPPCP (SEQ ID NO: 5) | APEFLGGPSVFLFPPKPKDTLMISRTPEVTCVVVDVSQEDPEVQFNWYVDGVEVHNAKTKPREEQFNSTYRWSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVMHEALHNHYTQKSLSLSLGK (SEQ ID NO: 1) | IEGRMD (SEQ ID NO: 7) | SKYGPPCPPCPAPEFLGGPSVFLFPPKPKDTLMISRTPEVTCVVVDVSQEDPEVQFNWYVDGVEVHNAKTKPREEQFNSTYRWSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVMHEALHNHYTQKSLSLSLGKIEGRMD (SEQ ID NO: 54) |
| SKYGPPCPPCP (SEQ ID NO: 5) | APEFLGGPSVFLFPPKPKDQLMISRTPEVTCVVVDVSQEDPEVQFNWYVDGVEVHNAKTKPREEQFNSTYRWSVLTTPHSDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVLHEALHNHYTQKSLSLSLGK (SEQ ID NO: 2) | IEGRMD (SEQ ID NO: 7) | SKYGPPCPPCPAPEFLGGPSVFLFPPKPKDQLMISRTPEVTCVVVDVSQEDPEVQFNWYVDGVEVHNAKTKPREEQFNSTYRWSVLTTPHSDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVLHEALHNHYTQKSLSLSLGKIEGRMD (SEQ ID NO: 55) |
| SKYGPPCPPCP (SEQ ID NO: 5) | APEFLGGPSVFLFPPKPKDQLMISRTPEVTCVVVDVSQEDPEVQFNWYVDGVEVHNAKTKPREEQFNSTYRWSVLTVLHQDWLSGKEYKCKVSSKGLPSSIEKTISNATGQPREPQVYTLPPSQEEMTKNQVSLTCLVKGFYPSDIAVEWESNGQPENNY | IEGRMD (SEQ ID NO: 7) | SKYGPPCPPCPAPEFLGGPSVFLFPPKPKDQLMISRTPEVTCVVVDVSQEDPEVQFNWYVDGVEVHNAKTKPREEQFNSTYRWSVLTVLHQDWLSGKEYKCKVSSKGLPSSIEKTISNATGQPREPQVYTLPPSQEEMTKNQVSLTCLVKGFYPSDIAV |

TABLE 2-continued

Illustrative modular linkers

| Joining Linker 1 | Fc | Joining Linker 2 | Modular Linker = Joining Linker 1 + Fc + Joining Linker 2 |
|---|---|---|---|
| | KTTPPVLDSDGSFFLYSRLTVDKS RWQEGNVFSCSVLHEALHNHYT QKSLSLSLGK (SEQ ID NO: 3) | | EWESNGQPENNYKTTPPVLDSD GSFFLYSRLTVDKSRWQEGNVFS CSVLHEALHNHYTQKSLSLSLGKI EGRMD (SEQ ID NO: 56) |

In embodiments, the present chimeric proteins may comprise variants of the modular linkers disclosed in Table 2, above. For instance, a linker may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the amino acid sequence of any one of SEQ ID NOs: 51 to 56.

In embodiments, the linker may be flexible, including without limitation highly flexible. In embodiments, the linker may be rigid, including without limitation a rigid alpha helix. Characteristics of illustrative joining linkers is shown below in Table 3:

TABLE 3

Characteristics of illustrative joining linkers

| Joining Linker Sequence | Characteristics |
|---|---|
| SKYGPPCPPCP (SEQ ID NO: 5) | IgG4 Hinge Region |
| IEGRMD (SEQ ID NO: 7) | Linker |
| GGGVPRDCG (SEQ ID NO: 8) | Flexible |
| GGGSGGGS (SEQ ID NO: 10) | Flexible |
| GGGSGGGSGGG (SEQ ID NO: 11) | Flexible |
| EGKSSGSGSESKST (SEQ ID NO: 12) | Flexible + soluble |
| GGSG (SEQ ID NO: 13) | Flexible |
| GGSGGGSGGGSG (SEQ ID NO: 14) | Flexible |
| EAAAKEAAAKEAAAK (SEQ ID NO: 15) | Rigid Alpha Helix |
| EAAAREAAAREAAAREAAAR (SEQ ID NO: 16) | Rigid Alpha Helix |
| GGGGSGGGGSGGGGSAS (SEQ ID NO: 17) | Flexible |
| GGGGAGGGG (SEQ ID NO: 18) | Flexible |
| GS (SEQ ID NO: 19) | Highly flexible |
| GSGSGS (SEQ ID NO: 20) | Highly flexible |
| GSGSGSGSGS (SEQ ID NO: 21) | Highly flexible |
| GGGGSAS (SEQ ID NO: 22) | Flexible |
| APAPAPAPAPAPAPAPAP (SEQ ID NO: 23) | Rigid |

In embodiments, the linker may be functional. For example, without limitation, the linker may function to improve the folding and/or stability, improve the expression, improve the pharmacokinetics, and/or improve the bioactivity of the present chimeric protein. In another example, the linker may function to target the chimeric protein to a particular cell type or location.

In embodiments, a chimeric protein comprises only one joining linkers.

In embodiments, a chimeric protein lacks joining linkers.

In embodiments, the linker is a synthetic linker such as polyethylene glycol (PEG).

In embodiments, a chimeric protein has a first domain which is sterically capable of binding its ligand/receptor and/or the second domain which is sterically capable of binding its ligand/receptor. Thus, there is enough overall flexibility in the chimeric protein and/or physical distance between an extracellular domain (or portion thereof) and the rest of the chimeric protein such that the ligand/receptor binding domain of the extracellular domain is not sterically hindered from binding its ligand/receptor. This flexibility and/or physical distance (which is referred to as "slack") may be normally present in the extracellular domain(s), normally present in the linker, and/or normally present in the chimeric protein (as a whole). Alternately, or additionally, an amino acid sequence (for example) may be added to one or more extracellular domains and/or to the linker to provide the slack needed to avoid steric hindrance. Any amino acid sequence that provides slack may be added. In embodiments, the added amino acid sequence comprises the sequence $(Gly)_n$ where n is any number from 1 to 100. Additional examples of addable amino acid sequence include the joining linkers described in Table 1 and Table 3. In embodiments, a polyethylene glycol (PEG) linker may be added between an extracellular domain and a linker to provide the slack needed to avoid steric hindrance. Such PEG linkers are well known in the art.

In embodiments, a chimeric protein of the present invention comprises the extracellular domain of FLT3L (or a variant thereof), a linker, and the extracellular domain of 4-1BBL (or a variant thereof). In embodiments, the linker comprises a hinge-CH2-CH3 Fc domain (or a variant thereof), e.g., from an IgG1 or from IgG4, including human IgG1 or IgG4. Thus, in embodiments, a chimeric protein of the present invention comprises the extracellular domain of FLT3L (or a variant thereof), linker comprising a hinge-CH2-CH3 Fc domain (or a variant thereof), and the extracellular domain of 4-1BBL (or a variant thereof). Such a chimeric protein may be referred to herein as "FLT3L-Fc-4-1BBL".

In embodiments, a chimeric protein of the present invention comprises the extracellular domain of FLT3L (or a variant thereof), a linker, and the extracellular domain of CD40L (or a variant thereof). In embodiments, the linker comprises a hinge-CH2-CH3 Fc domain (or a variant thereof), e.g., from an IgG1 or from IgG4, including human IgG1 or IgG4. Thus, in embodiments, a chimeric protein of the present invention comprises the extracellular domain of FLT3L (or a variant thereof), linker comprising a hinge-CH2-CH3 Fc domain (or a variant thereof), and the extracellular domain of CD40L (or a variant thereof). Such a chimeric protein may be referred to herein as "FLT3L-Fc-CD40L".

In embodiments, a chimeric protein of the present invention comprises the extracellular domain of FLT3L (or a variant thereof), a linker, and the extracellular domain of CD70 (or a variant thereof). In embodiments, the linker comprises a hinge-CH2-CH3 Fc domain (or a variant thereof), e.g., from an IgG1 or from IgG4, including human IgG1 or IgG4. Thus, in embodiments, a chimeric protein of the present invention comprises the extracellular domain of FLT3L (or a variant thereof), linker comprising a hinge-CH2-CH3 Fc domain (or a variant thereof), and the extracellular domain of CD40L (or a variant thereof). Such a chimeric protein may be referred to herein as "FLT3L-Fc-CD70L".

In embodiments, a chimeric protein of the present invention comprises the extracellular domain of FLT3L (or a variant thereof), a linker, and the extracellular domain of GITRL (or a variant thereof). In embodiments, the linker comprises a hinge-CH2-CH3 Fc domain (or a variant thereof), e.g., from an IgG1 or from IgG4, including human IgG1 or IgG4. Thus, in embodiments, a chimeric protein of the present invention comprises the extracellular domain of FLT3L (or a variant thereof), linker comprising a hinge-CH2-CH3 Fc domain (or a variant thereof), and the extracellular domain of GITRL (or a variant thereof). Such a chimeric protein may be referred to herein as "FLT3L-Fc-GITRL".

In embodiments, a chimeric protein of the present invention comprises the extracellular domain of FLT3L (or a variant thereof), a linker, and the extracellular domain of OX40L (or a variant thereof). In embodiments, the linker comprises a hinge-CH2-CH3 Fc domain (or a variant thereof), e.g., from an IgG1 or from IgG4, including human IgG1 or IgG4. Thus, in embodiments, a chimeric protein of the present invention comprises the extracellular domain of FLT3L (or a variant thereof), linker comprising a hinge-CH2-CH3 Fc domain (or a variant thereof), and the extracellular domain of OX40L (or a variant thereof). Such a chimeric protein may be referred to herein as "FLT3L-Fc-OX40L".

In embodiments, a chimeric protein of the present invention comprises the extracellular domain of FLT3L (or a variant thereof), a linker, and the extracellular domain of TL1A (or a variant thereof). In embodiments, the linker comprises a hinge-CH2-CH3 Fc domain (or a variant thereof), e.g., from an IgG1 or from IgG4, including human IgG1 or IgG4. Thus, in embodiments, a chimeric protein of the present invention comprises the extracellular domain of FLT3L (or a variant thereof), linker comprising a hinge-CH2-CH3 Fc domain (or a variant thereof), and the extracellular domain of CD40L (or a variant thereof). Such a chimeric protein may be referred to herein as "FLT3L-Fc-TL1A".

Diseases; Methods of Treatment, and Mechanisms of Action

A chimeric protein disclosed herein may be used in the treatment of cancer and/or in the treatment of an inflammatory disease, e.g., due to viral infection.

Aspects of the present invention provide methods of treating cancer. The methods comprise a step of administering to a subject in need thereof an effective amount of a pharmaceutical composition which comprises a chimeric protein as disclosed herein.

It is often desirable to enhance immune stimulatory signal transmission to boost an immune response, for instance to enhance a patient's anti-tumor immune response.

In embodiments, the chimeric protein of the present invention and/or chimeric protein used in methods of the present invention comprises an extracellular domain of FLT3L and an extracellular domain of a Type II membrane protein, each of which have immune stimulatory properties. Thus, the binding of the extracellular domain of FLT3L with its ligand/receptor (e.g., FLT3) will enhance, increase, and/or stimulate the transmission of an immune stimulatory signal.

The chimeric protein of the present invention and/or chimeric protein used in methods of the present invention further comprises an extracellular domain of a Type II membrane protein which provides an immune stimulatory signal; the Type II membrane protein being, without limitation, is one or more of 4-1BBL, APRIL, BAFF, BTNL2, CD28, CD30L, CD40L, CD70, C-type lectin domain (CLEC) family members, FasL, GITRL, LIGHT, LTa, LTa1b2, NKG2A, NKG2C, NKG2D, OX40L, RANKL, TL1A, TNFa, and TRAIL. Thus, the chimeric protein is engineered to enhances, increases, and/or stimulates the transmission of an immune stimulatory signal, by way of non-limiting example, the binding of one of 4-1BBL, APRIL, BAFF, BTNL2, CD28, CD30L, CD40L, CD70, C-type lectin domain (CLEC) family members, FasL, GITRL, LIGHT, LTa, LTa1b2, NKG2A, NKG2C, NKG2D, OX40L, RANKL, TL1A, TNFa, and TRAIL with its ligand/receptor. Accordingly, in embodiments, a chimeric protein has "dual costimulatory" capabilities from each of its first domain and its second domain.

In embodiments, the chimeric protein comprises an immune stimulatory signal which is an extracellular domain of a ligand of an immune stimulatory signal and this acts on a T cell that bears a cognate receptor of the immune stimulatory signal.

In embodiments, the extracellular domain may be used to provide artificial signaling.

In embodiments, the extracellular domain of a Type II transmembrane protein is an immune stimulatory signal.

In embodiments, the present invention pertains to cancers and/or tumors; for example, the treatment or prevention of cancers and/or tumors. As disclosed elsewhere herein, the treatment of cancer involves, in embodiments, modulating the immune system with the present chimeric proteins to favor of increasing or activating immune stimulatory signals.

In embodiments, the method reduces the amount or activity of regulatory T cells (Tregs) as compared to untreated subjects or subjects treated with antibodies directed to FLT3L, the Type II protein, and/or their respective ligands or receptors. In embodiments, the method increases priming of effector T cells in draining lymph nodes of the subject as compared to untreated subjects or subjects treated with antibodies directed to FLT3L, the Type II protein, and/or their respective ligands or receptors. In embodiments, the method causes an overall decrease in immunosuppressive cells and a shift toward a more inflammatory tumor environment as compared to untreated subjects or subjects treated with antibodies directed to the FLT3L, the Type II protein, and/or their respective ligands or receptors.

In embodiments, the present chimeric proteins are capable of, or can be used in methods comprising, modulating the amplitude of an immune response, e.g., modulating the level of effector output. In embodiments, e.g., when used for the treatment of cancer, the present chimeric proteins alter the extent of immune stimulation as compared to immune inhibition to increase the amplitude of a T cell response, including, without limitation, stimulating increased levels of cytokine production, proliferation or target killing potential. In embodiments, the patient's T cells are activated and/or stimulated by the chimeric protein, with the activated T cells being capable of dividing and/or secreting cytokines.

Cancers or tumors refer to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also, included are cells having abnormal proliferation that is not impeded by the immune system (e.g., virus infected cells). The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

The cancer may have an origin from any tissue. The cancer may originate from melanoma, colon, breast, or prostate, and thus may be made up of cells that were originally skin, colon, breast, or prostate, respectively. The cancer may also be a hematological malignancy, which may be leukemia or lymphoma. The cancer may invade a tissue such as liver, lung, bladder, or intestinal.

Representative cancers and/or tumors of the present invention include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL;

high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In embodiments, the chimeric protein is used to treat a subject that has a treatment-refractory cancer. In embodiments, the chimeric protein is used to treat a subject that is refractory to one or more immune-modulating agents. For example, in embodiments, the chimeric protein is used to treat a subject that presents no response to treatment, or even progress, after 12 weeks or so of treatment. For instance, in embodiments, the subject is refractory to a PD-1 and/or PD-L1 and/or PD-L2 agent, including, for example, nivolumab (ONO-4538/BMS-936558, MDX1106, OPDIVO, BRISTOL MYERS SQUIBB), pembrolizumab (KEYTRUDA, MERCK), MK-3475 (MERCK), BMS 936559 (BRISTOL MYERS SQUIBB), Ibrutinib (PHARMACYCLICS/ABBVIE), atezolizumab (TECENTRIQ, GENENTECH), and/or MPDL328OA (ROCHE)-refractory patients. For instance, in embodiments, the subject is refractory to an anti-CTLA-4 agent, e.g., ipilimumab (YERVOY)-refractory patients (e.g., melanoma patients). Accordingly, in embodiments the present invention provides methods of cancer treatment that rescue patients that are non-responsive to various therapies, including monotherapy of one or more immune-modulating agents.

In embodiments, the present invention provides chimeric proteins which target a cell or tissue within the tumor microenviroment. In embodiments, the cell or tissue within the tumor microenvironment expresses one or more targets or binding partners of the chimeric protein. The tumor microenvironment refers to the cellular milieu, including cells, secreted proteins, physiological small molecules, and blood vessels in which the tumor exists. In embodiments, the cells or tissue within the tumor microenvironment are one or more of: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T cells; macrophages; neutrophils; and other immune cells located proximal to a tumor. In embodiments, the present chimeric protein targets a cancer cell. In embodiments, the cancer cell expresses one or more of targets or binding partners of the chimeric protein.

In embodiments, the present methods provide treatment with the chimeric protein in a patient who is refractory to an additional agent, such "additional agents" being disclosed elsewhere herein, inclusive, without limitation, of the various chemotherapeutic agents disclosed herein.

The activation of regulatory T cells is critically influenced by costimulatory and co-inhibitory signals. Two major families of costimulatory molecules include the B7 and the tumor necrosis factor (TNF) families. These molecules bind to receptors on T cells belonging to the CD28 or TNF receptor families, respectively. Many well-defined co-inhibitors and their receptors belong to the B7 and CD28 families.

In embodiments, an immune stimulatory signal refers to a signal that enhances an immune response. For example, in the context of oncology, such signals may enhance antitumor immunity. For instance, without limitation, immune stimulatory signal may be identified by directly stimulating proliferation, cytokine production, killing activity, or phagocytic activity of leukocytes. Specific examples include direct stimulation of TNF superfamily receptors such as OX40, LTbR, CD27, CD30, 4-1BB or TNFRSF25 using either receptor agonist antibodies or using a chimeric protein comprising the ligands for such receptors (OX40L, LIGHT, CD70, CD30L, 4-1BBL, TL1A, respectively). Stimulation from any one of these receptors may directly stimulate the proliferation and cytokine production of individual T cell subsets. Another example includes direct stimulation of an immune inhibitory cell with through a receptor that inhibits the activity of such an immune suppressor cell. This would include, for example, stimulation of CD4+FoxP3+ regulatory T cells with a GITR agonist antibody or GITRL containing chimeric protein, which would reduce the ability of those regulatory T cells to suppress the proliferation of conventional CD4+ or CD8+ T cells. In another example, this would include stimulation of CD40 on the surface of an antigen presenting cell using a CD40 agonist antibody or a chimeric protein containing CD40L, causing activation of antigen presenting cells including enhanced ability of those cells to present antigen in the context of appropriate native costimulatory molecules, including those in the B7 or TNF superfamily. In another example, this would include stimulation of LTBR on the surface of a lymphoid or stromal cell using a LIGHT containing chimeric protein, causing activation of the lymphoid cell and/or production of pro-inflammatory cytokines or chemokines to further stimulate an immune response, optionally within a tumor.

In embodiments, the present chimeric proteins are capable of, or find use in methods involving, enhancing, restoring, promoting and/or stimulating immune modulation. In embodiments, the present chimeric proteins described herein, restore, promote and/or stimulate the activity or activation of one or more immune cells against tumor cells including, but not limited to: T cells, cytotoxic T lymphocytes, T helper cells, natural killer (NK) cells, natural killer T (NKT) cells, anti-tumor macrophages (e.g., M1 macrophages), B cells, and dendritic cells. In embodiments, the present chimeric proteins enhance, restore, promote and/or stimulate the activity and/or activation of T cells, including, by way of a non-limiting example, activating and/or stimulating one or more T– cell intrinsic signals, including a pro-survival signal; an autocrine or paracrine growth signal; a p38 MAPK-, ERK-, STAT-, JAK-, AKT- or PI3K-mediated signal; an anti-apoptotic signal; and/or a signal promoting and/or necessary for one or more of: pro-inflammatory cytokine production or T cell migration or T cell tumor infiltration.

In embodiments, the present chimeric proteins are capable of, or find use in methods involving, causing an increase of one or more of T cells (including without limitation cytotoxic T lymphocytes, T helper cells, natural killer T (NKT) cells), B cells, natural killer (NK) cells, natural killer T (NKT) cells, dendritic cells, monocytes, and macrophages (e.g., one or more of M1 and M2) into a tumor or the tumor microenvironment. In embodiments, the chimeric protein enhances recognition of tumor antigens by CD8+ T cells, particularly those T cells that have infiltrated into the tumor microenvironment. In embodiments, the present chimeric protein induces CD19 expression and/or increases the number of CD19 positive cells (e.g., CD19 positive B cells). In embodiments, the present chimeric protein induces IL-15Rα expression and/or increases the number of IL-15Rα positive cells (e.g., IL-15Rα positive dendritic cells).

In embodiments, the present chimeric proteins are capable of, or find use in methods involving, inhibiting and/or causing a decrease in immunosuppressive cells (e.g., myeloid-derived suppressor cells (MDSCs), regulatory T cells (Tregs), tumor associated neutrophils (TANs), M2 macrophages, and tumor associated macrophages (TAMs)), and particularly within the tumor and/or tumor microenvironment (TME). In embodiments, the present therapies may alter the ratio of M1 versus M2 macrophages in the tumor site and/or TME to favor M1 macrophages.

In embodiments, the present chimeric proteins are able to increase the serum levels of various cytokines or chemokines including, but not limited to, one or more of IFNγ, TNFα, IL-2, IL-4, IL-5, IL-6, IL-7, IL-9, IL-10, IL-13, IL-15, IL-17A, IL-17F, IL-22, CCL2, CCL3, CCL4, CXCL8, CXCL9, CXCL10, CXCL11 and CXCL12. In embodiments, the present chimeric proteins are capable of enhancing IL-2, IL-4, IL-5, IL-10, IL-13, IL-17A, IL-22, TNFα or IFNγ in the serum of a treated subject. In embodiments, administration of the present chimeric protein is capable of enhancing TNFα secretion. In a specific embodiment, administration of the present chimeric protein is capable of enhancing superantigen mediated TNFα secretion by leukocytes. Detection of such a cytokine response may provide a method to determine the optimal dosing regimen for the indicated chimeric protein.

In a chimeric protein of the present invention and/or a chimeric protein used in methods of the present invention, the chimeric protein is capable of increasing or preventing a decrease in a sub-population of CD4+ and/or CD8+ T cells.

In a chimeric protein of the present invention and/or a chimeric protein used in methods of the present invention, the chimeric protein is capable of enhancing tumor killing activity by T cells.

In embodiments, the present chimeric proteins inhibit, block and/or reduce cell death of an anti-tumor CD8+ and/or CD4+ T cell; or stimulate, induce, and/or increase cell death of a pro-tumor T cell. T cell exhaustion is a state of T cell dysfunction characterized by progressive loss of proliferative and effector functions, culminating in clonal deletion. Accordingly, a pro-tumor T cell refers to a state of T cell dysfunction that arises during many chronic infections, inflammatory diseases, and cancer. This dysfunction is defined by poor proliferative and/or effector functions, sustained expression of inhibitory receptors and a transcriptional state distinct from that of functional effector or memory T cells. Exhaustion prevents optimal control of infection and tumors. Illustrative pro-tumor T cells include, but are not limited to, Tregs, CD4+ and/or CD8+ T cells expressing one or more checkpoint inhibitory receptors, Th2 cells and Th17 cells. Checkpoint inhibitory receptors refer to receptors expressed on immune cells that prevent or inhibit uncontrolled immune responses. In contrast, an anti-tumor CD8+ and/or CD4+ T cell refers to T cells that can mount an immune response to a tumor.

In embodiments, the present chimeric proteins are capable of, and can be used in methods comprising, increasing a ratio of effector T cells to regulatory T cells. Illustrative effector T cells include ICOS+ effector T cells; cytotoxic T cells (e.g., αβ TCR, CD3+, CD8+, CD45RO+); CD4+ effector T cells (e.g., αβ TCR, CD3+, CD4+, CCR7+, CD62Lhi, IL-7R/CD127+; CD8+ effector T cells (e.g., αβ TCR, CD3+, CD8+, CCR7+, CD62Lhi, IL-7R/CD127+); effector memory T cells (e.g., CD62Llow, CD44+, TCR, CD3+, IL-7R/CD127+, CCR7low); central memory T cells (e.g., CCR7+, CD62L+, CD27+; or CCR7hi, CD44+, CD62Lhi, TCR, CD3+, IL-7R/CD127+, IL-15R+); CD62L+ effector T cells; CD8+ effector memory T cells (TEM) including early effector memory T cells (CD27+ CD62L−) and late effector memory T cells (CD27− CD62L−) (TemE and TemL, respectively); CD127 (+)CD25(low/−) effector T cells; CD127(−)CD25(−) effector T cells; CD8+ stem cell memory effector cells (TSCM) (e.g., CD44(low)CD62L(high)CD122(high)sca(+); TH1 effector T-cells (e.g., CXCR3+, CXCR6+ and CCR5+; or αβ TCR, CD3+, CD4+, IL-12R+, IFNγR+, CXCR3+), TH2 effector T cells (e.g., CCR3+, CCR4+ and CCR8+; or αβ TCR, CD3+, CD4+, IL-4R+, CCR4+, IL-17RB+, CRTH2+); TH9 effector T cells (e.g., αβ TCR, CD3+, CD4+); TH17 effector T cells (e.g., αβ TCR, CD3+, CD4+, IL-23R+, CCR6', IL-1R+); CD4+CD45RO+CCR7+ effector T cells, CD4+CD45RO+CCR7(−) effector T cells; and effector T cells secreting IL-2, IL-4 and/or IFN-γ. Illustrative regulatory T cells include ICOS' regulatory T cells, CD4+CD25+ FOXP3+ regulatory T cells, CD4+CD25+ regulatory T cells, CD4+CD25− regulatory T cells, CD4+CD25high regulatory T cells, TIM-3+PD-1+ regulatory T cells, lymphocyte activation gene-3 (LAG-3)+ regulatory T cells, CTLA-4/CD152+ regulatory T cells, neuropilin-1 (Nrp-1)+ regulatory T cells, CCR4+CCR8+ regulatory T cells, CD62L (L-selectin)+ regulatory T cells, CD45RBlow regulatory T cells, CD127low regulatory T cells, LRRC32/GARP+ regulatory T cells, CD39+ regulatory T cells, GITR+ regulatory T cells, LAP+ regulatory T cells, 1B11+ regulatory T cells, BTLA+ regulatory T cells, type 1 regulatory T cells (Tr1 cells), T helper type 3 (Th3) cells, regulatory cell of natural killer T cell phenotype (NKTregs), CD8+ regulatory T cells, CD8+ CD28− regulatory T cells and/or regulatory T-cells secreting IL-10, IL-35, TGF-6, TNF-α, Galectin-1, IFN-γ and/or MCP1.

In embodiments, the chimeric protein of the invention causes an increase in effector T cells (e.g., CD4+CD25− T cells).

In embodiments, the chimeric protein causes a decrease in regulatory T cells (e.g., CD4+CD25+ T cells).

In embodiments, the chimeric protein causes an increase in CD103+ antigen presenting cells (e.g., CD11c+CD103+ cells).

In embodiments, the chimeric protein generates a memory response which may, e.g., be capable of preventing relapse or protecting the animal from a recurrence and/or preventing, or reducing the likelihood of, metastasis. Thus, an animal treated with the chimeric protein is later able to attack tumor cells and/or prevent development of tumors when rechallenged after an initial treatment with the chimeric protein. Accordingly, a chimeric protein of the present invention and/or a chimeric protein used in methods of the present invention stimulates both active tumor destruction and also immune recognition of tumor antigens, which are essential in programming a memory response capable of preventing relapse.

In embodiments, the chimeric protein is capable of causing activation of antigen presenting cells. In embodiments, the chimeric protein is capable enhancing the ability of antigen presenting cells to present antigen.

In embodiments, the chimeric protein causes an increase in the frequency and/or absolute numbers of CD103+ antigen presenting cells (e.g., CD11c+CD103+ cells).

In embodiments, the chimeric protein simultaneously causes an increase in the frequency and/or absolute numbers of CD103+ antigen presenting cells (e.g., CD11c+CD103+ cells) and the activation status of those same cells (e.g., by increasing expression of CD80, and/or CD86, and/or CD40, and/or IL-12 and/or IFNg, and/or CD8).

In embodiments, the present chimeric proteins are capable of, and can be used in methods comprising, transiently stimulating effector T cells for longer than about 12 hours, about 24 hours, about 48 hours, about 72 hours or about 96 hours or about 1 week or about 2 weeks. In embodiments, the transient stimulation of effector T cells occurs substantially in a patient's bloodstream or in a particular tissue/location including lymphoid tissues such as for example, the bone marrow, lymph-node, spleen, thymus, mucosa-associated lymphoid tissue (MALT), non-lymphoid tissues, or in the tumor microenvironment.

In a chimeric protein of the present invention and/or a chimeric protein used in methods of the present invention, the present chimeric protein unexpectedly provides binding of the extracellular domain components to their respective binding partners with slow off rates (Kd or $K_{off}$). In embodiments, this provides an unexpectedly long interaction of the receptor to ligand and vice versa. Such an effect allows for a longer positive signal effect, e.g., increase in or activation of immune stimulatory signals. For example, the present chimeric protein, e.g., via the long off rate binding allows sufficient signal transmission to provide immune cell proliferation, allow for anti-tumor attack, allows sufficient signal transmission to provide release of stimulatory signals, e.g., cytokines.

In a chimeric protein of the present invention and/or a chimeric protein used in methods of the present invention, the chimeric protein is capable of forming a stable synapse between cells. The stable synapse of cells promoted by the chimeric proteins provides spatial orientation to favor tumor reduction—such as positioning the T cells to attack tumor cells. In embodiments, this provides longer on-target (e.g., intra-tumoral) half-life ($t_{1/2}$) as compared to serum $t_{1/2}$ of the chimeric proteins. Such properties could have the combined advantage of reducing off-target toxicities associated with systemic distribution of the chimeric proteins.

Additionally, the chimeric protein may independently bind to and activate two receptors/ligands (e.g., FLT3 and a Type II transmembrane protein's receptor/ligand) on a single immune system cell's surface.

In embodiments, the chimeric protein is capable of providing a sustained immunomodulatory effect.

The present chimeric proteins provide synergistic therapeutic effects (e.g., anti-tumor effects) as it allows for improved site-specific interplay of two immunotherapy agents. In embodiments, the present chimeric proteins provide the potential for reducing off-site and/or systemic toxicity.

In embodiments, the present chimeric protein exhibit enhanced safety profiles. In embodiment, the present chimeric protein exhibit reduced toxicity profiles. For example, administration of the present chimeric proteins may result in reduced side effects such as one or more of diarrhea, inflammation (e.g., of the gut), or weight loss, which occur following administration of antibodies directed to the ligand(s)/receptor(s) targeted by the extracellular domains of the present chimeric proteins. In embodiments, the present chimeric protein provides improved safety, as compared to antibodies directed to the ligand(s)/receptor(s) targeted by the extracellular domains of the present chimeric proteins, yet, without sacrificing efficacy.

In embodiments, the present chimeric proteins provide reduced side-effects, e.g., GI complications, relative to current immunotherapies, e.g., antibodies directed to ligand(s)/receptor(s) targeted by the extracellular domains of the present chimeric proteins. Illustrative GI complications include abdominal pain, appetite loss, autoimmune effects, constipation, cramping, dehydration, diarrhea, eating problems, fatigue, flatulence, fluid in the abdomen or ascites, gastrointestinal (GI) dysbiosis, GI mucositis, inflammatory bowel disease, irritable bowel syndrome (IBS-D and IBS-C), nausea, pain, stool or urine changes, ulcerative colitis, vomiting, weight gain from retaining fluid, and/or weakness.

In some aspects, the present chimeric agents are used to treat one or more infections. In embodiments, the present chimeric proteins are used in methods of treating viral infections (including, for example, HIV and HCV). In embodiments, the infections induce immunosuppression. For example, HIV infections often result in immunosuppression in the infected subjects. Accordingly, as disclosed elsewhere herein, the treatment of such infections may involve, in embodiments, modulating the immune system with the present chimeric proteins to favor immune stimulation over blocking or preventing immune inhibition.

In embodiments, the present invention provides methods of treating viral infections including, without limitation, acute or chronic viral infections, for example, of the respiratory tract, of papilloma virus infections, of herpes simplex virus (HSV) infection, of human immunodeficiency virus (HIV) infection, and of viral infection of internal organs such as infection with hepatitis viruses. In embodiments, the viral infection is caused by a virus of family Flaviviridae. In embodiments, the virus of family Flaviviridae is selected from Yellow Fever Virus, West Nile virus, Dengue virus, Japanese Encephalitis Virus, St. Louis Encephalitis Virus, and Hepatitis C Virus. In embodiments, the viral infection is caused by a virus of family Picornaviridae, e.g., poliovirus, rhinovirus, coxsackievirus. In embodiments, the viral infection is caused by a member of Orthomyxoviridae, e.g., an influenza virus. In embodiments, the viral infection is caused by a member of Retroviridae, e.g., a lentivirus. In embodiments, the viral infection is caused by a member of Paramyxoviridae, e.g., respiratory syncytial virus, a human parainfluenza virus, rubulavirus (e.g., mumps virus), measles virus, and human metapneumovirus. In embodiments, the viral infection is caused by a member of Bunyaviridae, e.g., hantavirus. In embodiments, the viral infection is caused by a member of Reoviridae, e.g., a rotavirus.

Combination Therapies and Conjugation

In embodiments, the invention provides for chimeric proteins and methods that further comprise administering an additional agent to a subject. In embodiments, the invention pertains to co-administration and/or co-formulation. Any of the compositions disclosed herein may be co-formulated and/or co-administered.

In embodiments, any chimeric protein disclosed herein acts synergistically when co-administered with another agent and is administered at doses that are lower than the doses commonly employed when such agents are used as monotherapy. In embodiments, any agent referenced herein may be used in combination with any of the chimeric proteins disclosed herein.

In embodiments, inclusive of, without limitation, cancer applications, the present invention pertains to chemotherapeutic agents as additional agents. Examples of chemotherapeutic agents include, but are not limited to, alkylating agents such as thiotepa and CYTOMN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan);

bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE, vinorelbine; novantrone; teniposide; edatrexate;

daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In embodiments, inclusive of, without limitation, cancer applications, the present additional agent is one or more immune-modulating agents selected from an agent that blocks, reduces and/or inhibits PD-1 and PD-L1 or PD-L2 and/or the binding of PD-1 with PD-L1 or PD-L2 (by way of non-limiting example, one or more of nivolumab (ONO-4538/BMS-936558, MDX1106, OPDIVO, BRISTOL MYERS SQUIBB), pembrolizumab (KEYTRUDA, Merck), MK-3475 (MERCK), BMS 936559 (BRISTOL MYERS SQUIBB), atezolizumab (TECENTRIQ, GENENTECH), MPDL328OA (ROCHE)), an agent that increases and/or stimulates CD137 (4-1BB) and/or the binding of CD137 (4-1 BB) with one or more of 4-1BB ligand (by way of non-limiting example, urelumab (BMS-663513 and anti-4-1BB antibody), and an agent that blocks, reduces and/or inhibits the activity of CTLA-4 and/or the binding of CTLA-4 with one or more of AP2M1, CD80, CD86, SHP-2, and PPP2R5A and/or the binding of OX40 with OX40L (by way of non-limiting example GBR 830 (GLENMARK), MEDI6469 (MEDIMMUNE).

In embodiments, inclusive of, without limitation, infectious disease applications, the present invention pertains to anti-infectives as additional agents. In embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In embodiments, the chimeric proteins (and/or additional agents) disclosed herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc. Additionally, the derivative can contain one or more non-classical amino acids. In still other embodiments, the chimeric proteins (and/or additional agents) disclosed herein further comprise a cytotoxic agent, comprising, in illustrative embodiments, a toxin, a chemotherapeutic agent, a radioisotope, and an agent that causes apoptosis or cell death. Such agents may be conjugated to a composition disclosed herein.

The chimeric proteins (and/or additional agents) disclosed herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Pharmaceutical Composition

Aspects of the present invention include a pharmaceutical composition comprising a therapeutically effective amount of a chimeric protein as disclosed herein.

The chimeric proteins (and/or additional agents) disclosed herein can possess a sufficiently basic functional group, which can react with an inorganic or organic acid, or a carboxyl group, which can react with an inorganic or organic base, to form a pharmaceutically acceptable salt. A pharmaceutically-acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

In embodiments, the compositions disclosed herein are in the form of a pharmaceutically acceptable salt.

Further, any chimeric protein (and/or additional agents) disclosed herein can be administered to a subject as a component of a composition, e.g., pharmaceutical composition, that comprises a pharmaceutically acceptable carrier or vehicle. Such pharmaceutical compositions can optionally comprise a suitable amount of a pharmaceutically acceptable excipient so as to provide the form for proper administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In embodiments, the pharmaceutically acceptable excipients are sterile when administered to a subject. Water is a useful excipient when any agent disclosed herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent disclosed herein, if desired, can also comprise minor amounts of wetting or emulsifying agents, or pH buffering agents.

In embodiments, the compositions, e.g., pharmaceutical compositions, disclosed herein are resuspended in a saline buffer (including, without limitation TBS, PBS, and the like).

In embodiments, the chimeric proteins may by conjugated and/or fused with another agent to extend half-life or otherwise improve pharmacodynamic and pharmacokinetic properties. In embodiments, the chimeric proteins may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In embodiments, each of the individual chimeric proteins is fused to one or more of the agents described in BioDrugs (2015) 29:215-239, the entire contents of which are hereby incorporated by reference.

The present invention includes the disclosed chimeric protein (and/or additional agents) in various formulations of pharmaceutical composition. Any chimeric protein (and/or additional agents) disclosed herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. DNA or RNA constructs encoding the protein sequences may also be used. In embodiments, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the pharmaceutical compositions comprising the chimeric protein (and/or additional agents) can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

The pharmaceutical compositions comprising the chimeric protein (and/or additional agents) of the present invention may conveniently be presented in unit dosage forms and may be prepared by any of the methods well known in the art of pharmacy. Such methods generally include the step of bringing therapeutic agents into association with a carrier, which constitutes one or more accessory ingredients. Typically, the pharmaceutical compositions are prepared by uniformly and intimately bringing therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art)

In embodiments, any chimeric protein (and/or additional agents) disclosed herein is formulated in accordance with routine procedures as a pharmaceutical composition adapted for a mode of administration disclosed herein.

Administration, Dosing, and Treatment Regimens

Routes of administration include, for example: intradermal, intratumoral, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

As examples, administration results in the release of chimeric protein (and/or additional agents) disclosed herein into the bloodstream (via enteral or parenteral administration), or alternatively, the chimeric protein (and/or additional agents) is administered directly to the site of active disease.

Any chimeric protein (and/or additional agents) disclosed herein can be administered orally. Such chimeric proteins (and/or additional agents) can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

In specific embodiments, it may be desirable to administer locally to the area in need of treatment. In embodiments, for instance in the treatment of cancer, the chimeric protein (and/or additional agents) are administered in the tumor microenvironment (e.g., cells, molecules, extracellular matrix and/or blood vessels that surround and/or feed a tumor cell, inclusive of, for example, tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T cells; macrophages; neutrophils; and other immune cells located proximal to a tumor) or lymph node and/or targeted to the tumor microenvironment or lymph node. In embodiments, for instance in the treatment of cancer, the chimeric protein (and/or additional agents) are administered intratumorally.

In embodiments, the present chimeric protein allows for a dual effect that provides less side effects than are seen in conventional immunotherapy (e.g., treatments with one or more of OPDIVO, KEYTRUDA, YERVOY, and TECENTRIQ). For example, the present chimeric proteins reduce or prevent commonly observed immune-related adverse events that affect various tissues and organs including the skin, the gastrointestinal tract, the kidneys, peripheral and central nervous system, liver, lymph nodes, eyes, pancreas, and the endocrine system; such as hypophysitis, colitis, hepatitis, pneumonitis, rash, and rheumatic disease. Further, the present local administration, e.g., intratumorally, obviate adverse event seen with standard systemic administration, e.g., IV infusions, as are used with conventional immunotherapy (e.g., treatments with one or more of OPDIVO, KEYTRUDA, YERVOY, and TECENTRIQ).

Dosage forms suitable for parenteral administration (e.g., intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g., lyophilized composition), which can be dissolved or suspended in sterile injectable medium immediately before use. They may contain, for example, suspending or dispersing agents known in the art.

The dosage of any chimeric protein (and/or additional agents) disclosed herein as well as the dosing schedule can depend on various parameters, including, but not limited to, the disease being treated, the subject's general health, and the administering physician's discretion. Any chimeric protein disclosed herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional agent, to a subject in need thereof.

In embodiments, a chimeric protein and an additional agent(s) are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days apart, 4 days apart, 5 days apart, 6 days apart, 1 week apart, 2 weeks apart, 3 weeks apart, or 4 weeks apart.

In embodiments, the present invention relates to the co-administration of a chimeric protein which induces an innate immune response and another chimeric protein which induces an adaptive immune response. In such embodiments, the chimeric protein which induces an innate immune response may be administered before, concurrently with, or subsequent to administration of the chimeric protein which induces an adaptive immune response. For example, the chimeric proteins may be administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days apart, 4 days apart, 5 days apart, 6 days apart, 1 week apart, 2 weeks apart, 3 weeks apart, or 4 weeks apart. In an illustrative embodiment, the chimeric protein which induces an innate immune response and the chimeric protein which induces an adaptive response are administered 1 week apart, or administered on alternate weeks (i.e., administration of the chimeric protein inducing an innate immune response is followed 1 week later with administration of the chimeric protein which induces an adaptive immune response and so forth).

The dosage of any chimeric protein (and/or additional agents) disclosed herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

For administration of any chimeric protein (and/or additional agents) disclosed herein by parenteral injection, the dosage may be about 0.1 mg to about 250 mg per day, about 1 mg to about 20 mg per day, or about 3 mg to about 5 mg per day. Generally, when orally or parenterally administered, the dosage of any agent disclosed herein may be about 0.1 mg to about 1500 mg per day, or about 0.5 mg to about 10 mg per day, or about 0.5 mg to about 5 mg per day, or about 200 to about 1,200 mg per day (e.g., about 200 mg, about 300 mg, about 400 mg, about 500 mg, about 600 mg, about 700 mg, about 800 mg, about 900 mg, about 1,000 mg, about 1,100 mg, about 1,200 mg per day).

In embodiments, administration of the chimeric protein (and/or additional agents) disclosed herein is by parenteral injection at a dosage of about 0.1 mg to about 1500 mg per treatment, or about 0.5 mg to about 10 mg per treatment, or about 0.5 mg to about 5 mg per treatment, or about 200 to about 1,200 mg per treatment (e.g., about 200 mg, about 300 mg, about 400 mg, about 500 mg, about 600 mg, about 700 mg, about 800 mg, about 900 mg, about 1,000 mg, about 1,100 mg, about 1,200 mg per treatment).

In embodiments, a suitable dosage of the chimeric protein (and/or additional agents) is in a range of about 0.01 mg/kg to about 100 mg/kg of body weight, or about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, inclusive of all values and ranges therebetween.

In another embodiment, delivery can be in a vesicle, in particular a liposome (see Langer, 1990, *Science* 249:1527-1533; Treat et al, in *Liposomes in Therapy of Infectious Disease and Cancer*, Lopez-Berestein and Fidler (eds.), Liss, New York, pp. 353-365 (1989).

A chimeric protein (and/or additional agents) disclosed herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release*, Langer and Wise (eds.), CRC Pres., Boca Raton, Florida (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al, 1985, *Science* 228:190; During et al, 1989, *Ann. Neurol.* 25:351; Howard et al, 1989, *J. Neurosurg.* 71:105).

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Administration of any chimeric protein (and/or additional agents) disclosed herein can, independently, be one to four times daily or one to four times per month or one to six times per year or once every two, three, four or five years. Administration can be for the duration of one day or one month, two months, three months, six months, one year, two years, three years, and may even be for the life of the subject.

The dosage regimen utilizing any chimeric protein (and/or additional agents) disclosed herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. Any chimeric protein (and/or additional agents) disclosed herein can be administered in a single daily dose, or the total daily dosage can be administered in divided doses of two, three or four times daily. Furthermore, any chimeric protein (and/or additional agents) disclosed herein can be administered continuously rather than intermittently throughout the dosage regimen.

Cells and Nucleic Acids

Aspects of the present invention provide an expression vector comprising a nucleic acid which encodes a chimeric protein as disclosed herein. The expression vector comprises a nucleic acid encoding the chimeric protein disclosed herein. In embodiments, the expression vector comprises DNA or RNA. In embodiments, the expression vector is a mammalian expression vector.

Both prokaryotic and eukaryotic vectors can be used for expression of the chimeric protein. Prokaryotic vectors include constructs based on *E. coli* sequences (see, e.g., Makrides, *Microbiol Rev* 1996, 60:512-538). Non-limiting examples of regulatory regions that can be used for expression in *E. coli* include lac, trp, lpp, phoA, recA, tac, T3, T7 and $\lambda P_L$. Non-limiting examples of prokaryotic expression vectors may include the λgt vector series such as λgt11 (Huynh et al., in "DNA Cloning Techniques, Vol. I: A Practical Approach," 1984, (D. Glover, ed.), pp. 49-78, IRL Press, Oxford), and the pET vector series (Studier et al., *Methods Enzymol* 1990, 185:60-89). Prokaryotic host-vector systems cannot perform much of the post-translational processing of mammalian cells, however. Thus, eukaryotic host-vector systems may be particularly useful. A variety of regulatory regions can be used for expression of the chimeric proteins in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the β-interferon gene, and the hsp70 gene (see, Williams et al., *Cancer Res* 1989, 49:2735-42; and Taylor et al., *Mol Cell Biol* 1990, 10:165-75). Heat shock promoters or stress promoters also may be advantageous for driving expression of the chimeric proteins in recombinant host cells.

In embodiments, expression vectors of the invention comprise a nucleic acid encoding the chimeric proteins, or a complement thereof, operably linked to an expression control region, or complement thereof, that is functional in a mammalian cell. The expression control region is capable of driving expression of the operably linked blocking and/or stimulating agent encoding nucleic acid such that the blocking and/or stimulating agent is produced in a human cell transformed with the expression vector.

Expression control regions are regulatory polynucleotides (sometimes referred to herein as elements), such as promoters and enhancers, that influence expression of an operably linked nucleic acid. An expression control region of an expression vector of the invention is capable of expressing operably linked encoding nucleic acid in a human cell. In embodiments, the cell is a tumor cell. In another embodiment, the cell is a non-tumor cell. In embodiments, the expression control region confers regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

In embodiments, the present invention contemplates the use of inducible promoters capable of effecting high level of expression transiently in response to a cue. For example, when in the proximity of a tumor cell, a cell transformed with an expression vector for the chimeric protein (and/or additional agents) comprising such an expression control sequence is induced to transiently produce a high level of the agent by exposing the transformed cell to an appropriate cue. Illustrative inducible expression control regions include those comprising an inducible promoter that is stimulated with a cue such as a small molecule chemical compound. In other examples, the chimeric protein is expressed by a chimeric antigen receptor containing cell or an in vitro expanded tumor infiltrating lymphocyte, under the control of a promoter which is sensitive to antigen recognition by the cell, and leads to local secretion of the chimeric protein in response to tumor antigen recognition. Particular examples can be found, for example, in U.S. Pat. Nos. 5,989,910, 5,935,934, 6,015,709, and 6,004,941, each of which is incorporated herein by reference in its entirety.

Expression control regions and locus control regions include full-length promoter sequences, such as native promoter and enhancer elements, as well as subsequences or polynucleotide variants which retain all or part of full-length or non-variant function. As used herein, the term "functional" and grammatical variants thereof, when used in reference to a nucleic acid sequence, subsequence or fragment, means that the sequence has one or more functions of native nucleic acid sequence (e.g., non-variant or unmodified sequence).

As used herein, "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

Expression systems functional in human cells are well known in the art, and include viral systems. Generally, a promoter functional in a human cell is any DNA sequence capable of binding mammalian RNA polymerase and initiating the downstream (3') transcription of a coding sequence into mRNA. A promoter will have a transcription initiating region, which is usually placed proximal to the 5' end of the coding sequence, and typically a TATA box located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40. Introns may also be included in expression constructs.

There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also suitable for in vivo transduction. In some situations, it is desirable to provide a targeting agent, such as an antibody or ligand specific for a tumor cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al, J. Biol. Chem. 262, 4429-4432 (1987); and Wagner et al, Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al, TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003). In addition, direct and targeted genetic integration strategies may be used to insert nucleic acid sequences encoding the chimeric fusion proteins including CRISPR/CAS9, zinc finger, TALEN, and meganuclease gene-editing technologies.

In embodiments, the expression vectors for the expression of the chimeric proteins (and/or additional agents) are viral vectors. Many viral vectors useful for gene therapy are known (see, e.g., Lundstrom, Trends Biotechnol., 21: 1 17, 122, 2003. Illustrative viral vectors include those selected from Antiviruses (LV), retroviruses (RV), adenoviruses (AV), adeno-associated viruses (AAV), and a viruses, though other viral vectors may also be used. For in vivo uses, viral vectors that do not integrate into the host genome are suitable for use, such as a viruses and adenoviruses. Illustrative types of a viruses include Sindbis virus, Venezuelan equine encephalitis (VEE) virus, and Semliki Forest virus (SFV). For in vitro uses, viral vectors that integrate into the host genome are suitable, such as retroviruses, AAV, and Antiviruses. In embodiments, the invention provides methods of transducing a human cell in vivo, comprising contacting a solid tumor in vivo with a viral vector of the invention.

Aspects of the present invention include a host cell comprising the expression vector which comprises the chimeric protein disclosed herein.

Expression vectors can be introduced into host cells for producing the present chimeric proteins. Cells may be cultured in vitro or genetically engineered, for example. Useful mammalian host cells include, without limitation, cells derived from humans, monkeys, and rodents (see, for example, Kriegler in "Gene Transfer and Expression: A Laboratory Manual," 1990, New York, Freeman & Co.). These include monkey kidney cell lines transformed by SV40 (e.g., COS-7, ATCC CRL 1651); human embryonic kidney lines (e.g., 293, 293-EBNA, or 293 cells subcloned for growth in suspension culture, Graham et al, *J Gen Virol* 1977, 36:59); baby hamster kidney cells (e.g., BHK, ATCC CCL 10); Chinese hamster ovary-cells-DHFR (e.g., CHO, Urlaub and Chasin, *Proc Natl Acad Sci USA* 1980, 77:4216); DG44 CHO cells, CHO-K1 cells, mouse sertoli cells (Mather, *Biol Reprod* 1980, 23:243-251); mouse fibroblast cells (e.g., NIH-313), monkey kidney cells (e.g., CV1 ATCC CCL 70); African green monkey kidney cells. (e.g., VERO-76, ATCC CRL-1587); human cervical carcinoma cells (e.g., HELA, ATCC CCL 2); canine kidney cells (e.g., MDCK, ATCC CCL 34); buffalo rat liver cells (e.g., BRL 3A, ATCC CRL 1442); human lung cells (e.g., W138, ATCC CCL 75); human liver cells (e.g., Hep G2, HB 8065); and mouse mammary tumor cells (e.g., MMT 060562, ATCC CCL51). Illustrative cancer cell types for expressing the chimeric proteins disclosed herein include mouse fibroblast cell line, NI H3T3, mouse Lewis lung carcinoma cell line, LLC, mouse mastocytoma cell line, P815, mouse lymphoma cell line, EL4 and its ovalbumin transfectant, E.G7, mouse melanoma cell line, B16F10, mouse fibrosarcoma cell line, MC57, and human small cell lung carcinoma cell lines, SCLC #2 and SCLC #7.

Host cells can be obtained from normal or affected subjects, including healthy humans, cancer patients, and patients with an infectious disease, private laboratory deposits, public culture collections such as the American Type Culture Collection (ATCC), or from commercial suppliers.

Cells that can be used for production of the present chimeric proteins in vitro, ex vivo, and/or in vivo include, without limitation, epithelial cells, endothelial cells, keratinocytes, fibroblasts, muscle cells, hepatocytes; blood cells such as T lymphocytes, chimeric antigen receptor expressing T cells, tumor infiltrating lymphocytes, B lymphocytes, monocytes, macrophages, neutrophils, eosinophils, megakaryocytes, granulocytes; various stem or progenitor cells, in particular hematopoietic stem or progenitor cells (e.g., as obtained from bone marrow), umbilical cord blood, peripheral blood, and fetal liver. The choice of cell type depends on the type of tumor or infectious disease being treated or prevented, and can be determined by one of skill in the art.

Production and purification of Fc-containing macromolecules (such as monoclonal antibodies) has become a standardized process, with minor modifications between products. For example, many Fc containing macromolecules are produced by human embryonic kidney (HEK) cells (or variants thereof) or Chinese Hamster Ovary (CHO) cells (or variants thereof) or in some cases by bacterial or synthetic methods. Following production, the Fc containing macromolecules that are secreted by HEK or CHO cells are purified through binding to Protein A columns and subsequently 'polished' using various methods. Generally speaking, purified Fc containing macromolecules are stored in liquid form for some period of time, frozen for extended periods of time or in some cases lyophilized. In embodiments, production of the chimeric proteins contemplated herein may have unique characteristics as compared to traditional Fc containing macromolecules. In certain examples, the chimeric proteins may be purified using specific chromatography resins, or using chromatography methods that do not depend upon Protein A capture. In embodiments, the chimeric proteins may be purified in an oligomeric state, or in multiple oligomeric states, and enriched for a specific oligomeric state using specific methods. Without being bound by theory, these methods could include treatment with specific buffers including specified salt concentrations, pH and additive compositions. In other examples, such methods could include treatments that favor one oligomeric state over another. The chimeric proteins obtained herein may be additionally 'polished' using methods that are specified in the art. In embodiments, the chimeric proteins are highly stable and able to tolerate a wide range of pH exposure (between pH 3-12), are able to tolerate a large number of freeze/thaw stresses (greater than 3 freeze/thaw cycles) and are able to tolerate extended incubation at high temperatures (longer than 2 weeks at 40 degrees C.). In embodiments, the chimeric proteins are shown to remain intact, without evidence of degradation, deamidation, etc. under such stress conditions.

Subjects and/or Animals

In embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In embodiments, the subject and/or animal is a non-mammal, such, for example, a zebrafish. In embodiments, the subject and/or animal may comprise fluorescently-tagged cells (with e.g., GFP). In embodiments, the subject and/or animal is a transgenic animal comprising a fluorescent cell.

In embodiments, the subject and/or animal is a human. In embodiments, the human is a pediatric human. In embodiments, the human is an adult human. In embodiments, the human is a geriatric human. In embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In embodiments, the subject is a non-human animal, and therefore the invention pertains to veterinary use. In a specific embodiment, the non-human animal is a household pet. In another specific embodiment, the non-human animal is a livestock animal.

Kits and Medicaments

Aspects of the present invention provide kits that can simplify the administration of any agent disclosed herein.

An illustrative kit of the invention comprises any chimeric protein and/or pharmaceutical composition disclosed herein in unit dosage form. In embodiments, the unit dosage form is a container, such as a pre-filled syringe, which can be sterile, containing any agent disclosed herein and a pharmaceutically acceptable carrier, diluent, excipient, or vehicle. The kit can further comprise a label or printed instructions instructing the use of any agent disclosed herein. The kit may also include a lid speculum, topical anesthetic, and a cleaning agent for the administration location. The kit can also further comprise one or more additional agent disclosed herein. In embodiments, the kit comprises a container containing an effective amount of a composition of the invention and an effective amount of another composition, such those disclosed herein.

Aspects of the present invention include use of a chimeric protein as disclosed herein in the manufacture of a medicament, e.g., a medicament for treatment of cancer and/or treatment of an inflammatory disorder due to viral infection.

Any aspect or embodiment disclosed herein can be combined with any other aspect or embodiment as disclosed herein.

The invention will be further described in the following examples, which do not limit the scope of the invention described in the claims.

EXAMPLES

Example 1. Construction and Characterization of an Illustrative FLT3L- and 4-1BBL-Based Chimeric Protein A construct encoding a murine FLT3L- and 4-1BBL-based chimeric protein was generated. The "mFLT3L-Fc-4-1BBL" construct included a murine extracellular domain (ECD) of FLT3L fused to a murine ECD of 4-1BBL via a hinge-CH2-CH3 Fc domain derived from IgG1. See, FIG. 1D.

Figure 3A:
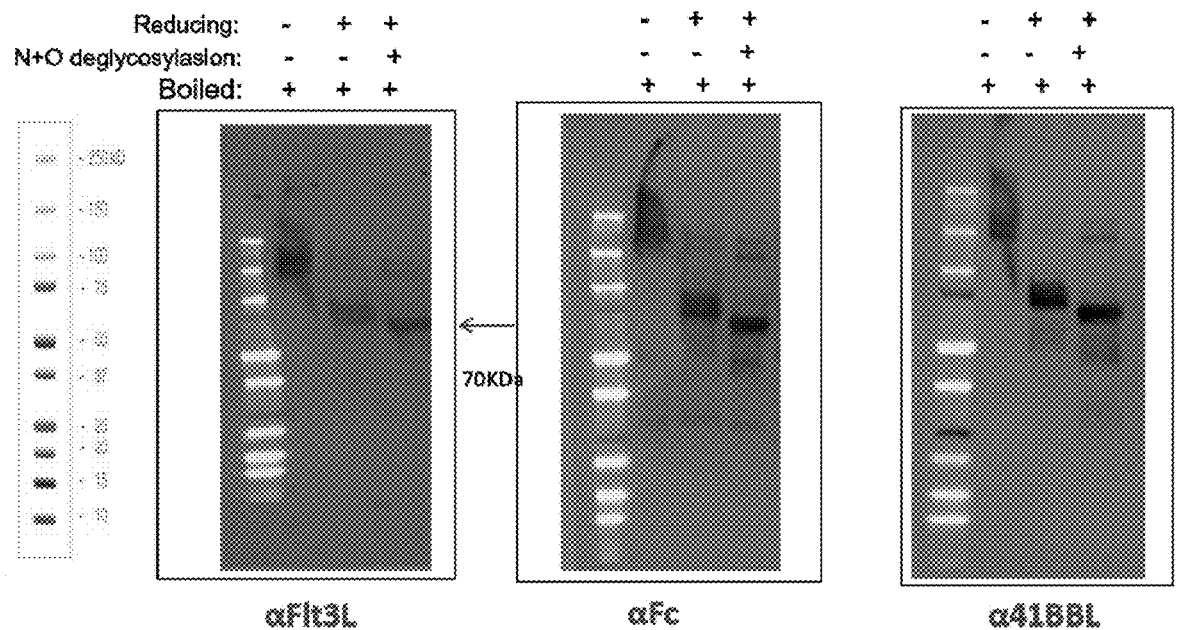
FIG. 3A shows characterization of a murine FLT3L-Fc-4-1BBL chimeric protein by Western blot demonstrating the chimeric proteins native state and tendency to form a multimer. Untreated samples (i.e., without reducing agent or deglycosylation agent) of the FLT3L-Fc-4-1BBL chimeric protein, e.g., control, were loaded into lane 2 in all the blots. Samples in lane 3 were treated with the reducing agent, β-mercaptoethanol. Samples in lane 4 were treated with a deglycosylation agent and the reducing agent. Each individual domain of the chimeric protein was probed using an anti-FLT3L, anti-Fc, or anti-4-1BBL antibody, respectively.

The mFLT3L-Fc-4-1BBL construct was transiently expressed in 293 cells and purified using protein-A affinity chromatography. Western blot analyses were performed to validate the detection and binding of all three components of mFLT3L-Fc-4-1BBL with their respective binding partners (FIG. 3A). The Western blots indicated the presence of a dominant multimeric band in the non-reduced lanes (FIG. 3A, lane 2 in each blot), which was reduced to a glycosylated monomeric band in the presence of the reducing agent, β-mercaptoethanol (FIG. 3A, lane 3 in each blot). As shown in FIG. 3A, lane 4 in each blot, the chimeric protein ran as a monomer at the predicted molecular weight of about 70 kDa in the presence of both a reducing agent (β-mercaptoethanol) and an deglycosylation agent.

Figure 3B:
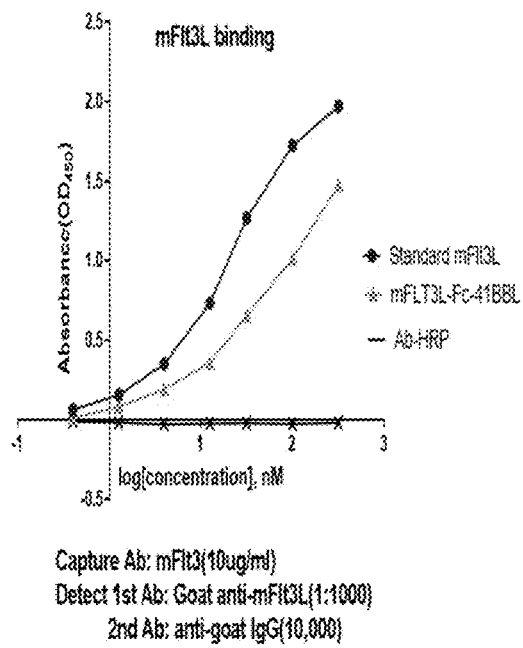
FIG. 3B to FIG. 3D show ELISA data demonstrating the binding affinity of mFLT3L domain of mFLT3L-Fc-4-1BBL (FIG. 3B), of the mFc domain (FIG. 3C), and of the 4-1BBL domain (FIG. 3D) for their respective binding partners.
Figure 3C:
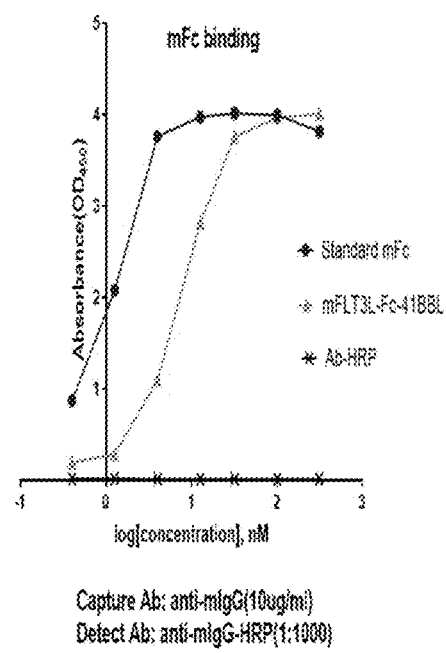
Figure 3D:
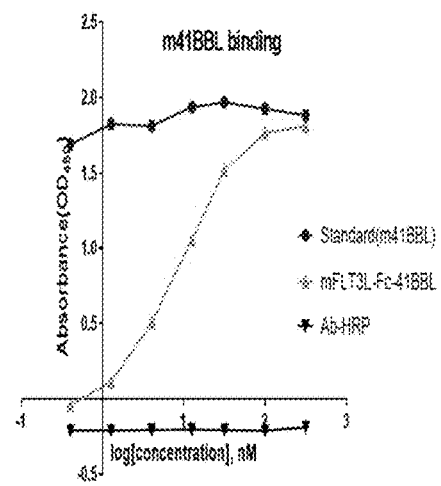

Functional ELISA (enzyme-linked immunosorbent assay) were performed to demonstrate the binding affinity of the different domains of the mFLT3L-Fc-4-1BBL chimeric protein to their respective binding partners. As shown in FIG. 3B, binding of the mFLT3L domain of the mFLT3L-Fc-4-1BBL chimeric protein was characterized by capturing to a plate-bound recombinant mouse mFLT3 protein and detecting via an anti-mFLT3L antibody and HRP staining. Recombinant mFLT3L protein was used to generate a standard curve. The data shown in FIG. 3B demonstrates that the mFLT3L domain of the mFLT3L-Fc-4-1BBL chimeric protein effectively interacted with its binding partner in a concentration-dependent manner and with high affinity. As shown in FIG. 3C, binding of the mFc portion of the mFLT3L-Fc-4-1BBL chimeric protein was characterized by capturing the chimeric protein to a plate-bound mouse IgG Fc gamma antibody and detecting via an HRP conjugated anti-mouse Fc antibody. A mouse whole IgG was used to generate a standard curve. As shown in FIG. 3D, binding of the m4-1BBL domain of the mFLT3L-Fc-4-1BBL chimeric protein was characterized by capturing to a plate-bound recombinant mouse m4-1BB protein and detecting via an anti-m4-1BBL antibody and HRP staining. Recombinant m4-1BBL protein was used to generate a standard curve. The data shown in FIG. 3D demonstrates that the m4-1BBL domain of the mFLT3L-Fc-4-1BBL chimeric protein effectively interacted with its binding partner in a concentration-dependent manner and with high affinity.

Example 2. Construction and Characterization of an Illustrative FLT3L- and CD40L-Based Chimeric Protein A construct encoding a murine FLT3L- and CD40L-based chimeric protein was generated. The "mFLT3L-Fc-CD40L" construct included a murine extracellular domain (ECD) of FLT3L fused to a murine ECD of CD40L via a hinge-CH2-CH3 Fc domain derived from IgG1. See, FIG. 1D.

Figure 4A:
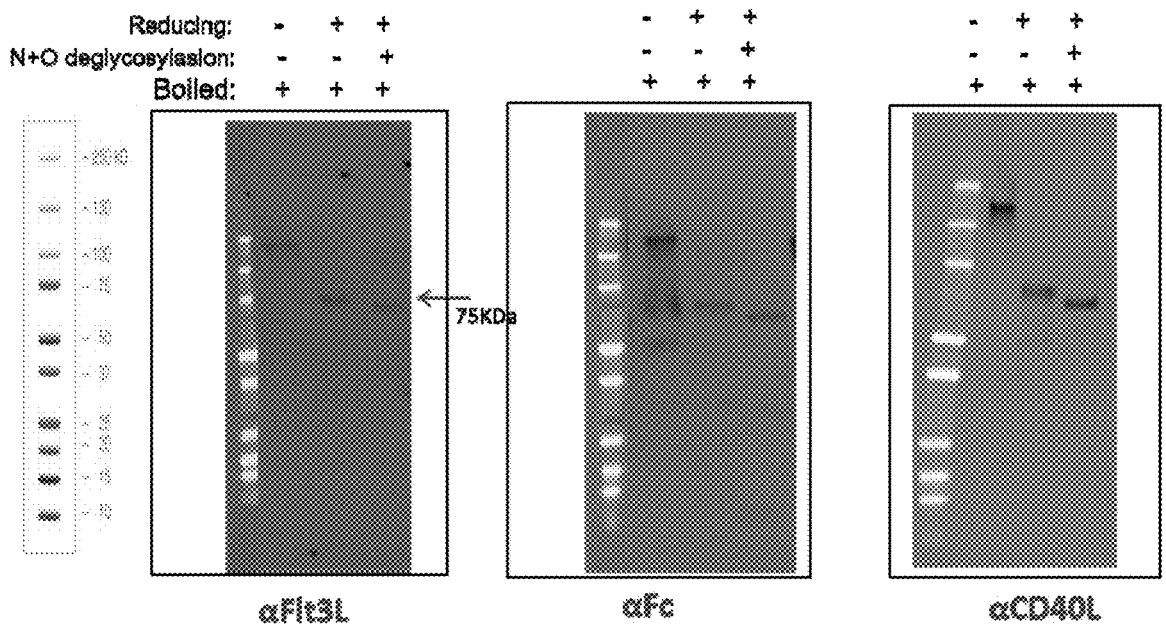
FIG. 4A shows characterization of a murine FLT3L-Fc-CD40L chimeric protein by Western blot demonstrating the chimeric proteins native state and tendency to form a multimer. Untreated samples (i.e., without reducing agent or deglycosylation agent) of the FLT3L-Fc-CD40L chimeric protein, e.g., control, were loaded into lane 2 in all the blots. Samples in lane 3 were treated with the reducing agent, β-mercaptoethanol. Samples in lane 4 were treated with a deglycosylation agent and the reducing agent. Each individual domain of the chimeric protein was probed using an anti-FLT3L, anti-Fc, or anti-CD40L antibody, respectively.

The mFLT3L-Fc-CD40L construct was transiently expressed in 293 cells and purified using protein-A affinity chromatography. Western blot analyses were performed to validate the detection and binding of all three components of mFLT3L-Fc-CD40L with their respective binding partners (FIG. 4A). The Western blots indicated the presence of a dominant multimeric band in the non-reduced lanes (FIG. 4A, lane 2 in each blot), which was reduced to a glycosylated monomeric band in the presence of the reducing agent, β-mercaptoethanol (FIG. 4A, lane 3 in each blot). As shown in FIG. 4A, lane 4 in each blot, the chimeric protein ran as a monomer at the predicted molecular weight of about 75 kDa in the presence of both a reducing agent (β-mercaptoethanol) and an deglycosylation agent.

Figure 4B:
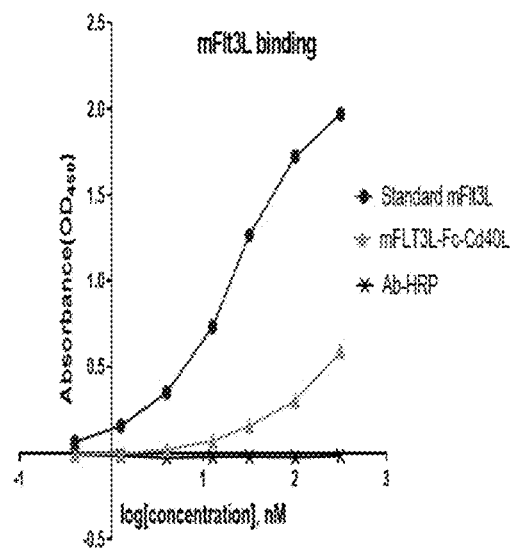
FIG. 4B to FIG. 4D show ELISA data demonstrating the binding affinity of mFLT3L domain of mFLT3L-Fc-CD40L (FIG. 4B), the of mFc domain (FIG. 4C), and of the mCD40L domain (FIG. 4D) for their respective binding partners.
Figure 4C:
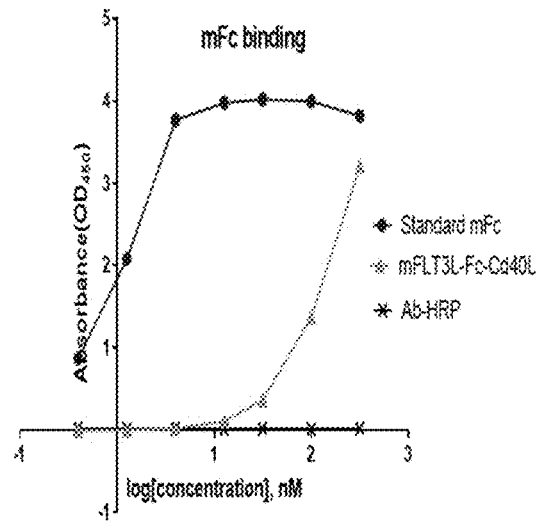
Figure 4D:
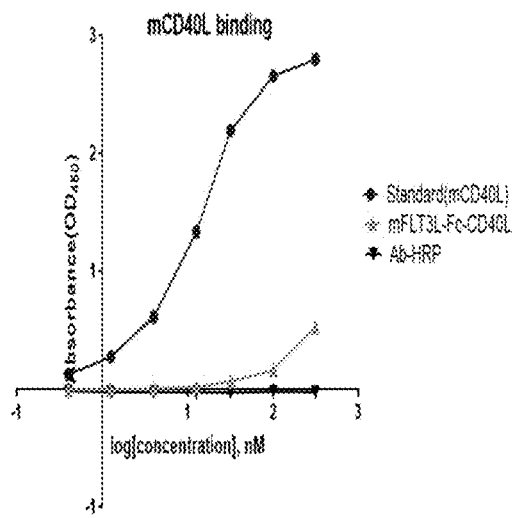

Functional ELISA were performed to demonstrate the binding affinity of the different domains of the mFLT3L-Fc-CD40L chimeric protein to their respective binding partners. As shown in FIG. 4B, binding of the mFLT3L domain of the mFLT3L-Fc-CD40L chimeric protein was characterized by capturing to a plate-bound recombinant mouse mFLT3 protein and detecting via an anti-mFLT3L antibody and HRP staining. Recombinant mFLT3L protein was used to generate a standard curve. The data shown in FIG. 4B demonstrates that the mFLT3L domain of the mFLT3L-Fc-CD40L chimeric protein effectively interacted with its binding partner in a concentration-dependent manner and with high affinity. As shown in FIG. 4C, binding of the mFc portion of the mFLT3L-Fc-CD40L chimeric protein was characterized by capturing the chimeric protein to a plate-bound mouse IgG Fc gamma antibody and detecting via an HRP conjugated anti-mouse Fc antibody. A mouse whole IgG was used to generate a standard curve. As shown in FIG. 4D, binding of the mCD40L domain of the mFLT3L-Fc-CD40L chimeric protein was characterized by capturing to a plate-bound recombinant mouse mCD40 protein and detecting via an anti-mCD40L antibody and HRP staining. Recombinant mCD40L protein was used to generate a standard curve. The data shown in FIG. 4D demonstrates that the mCD40L domain of the mFLT3L-Fc-CD40L chimeric protein effectively interacted with its binding partner in a concentration-dependent manner and with high affinity.

Example 3. Construction and Characterization of an Illustrative FLT3L- and OX40L-Based Chimeric Protein A construct encoding a murine FLT3L- and OX40L-based chimeric protein was generated. The "mFLT3L-Fc-OX40L" construct included a murine extracellular domain (ECD) of FLT3L fused to a murine ECD of OX40L via a hinge-CH2-CH3 Fc domain derived from IgG1. See, FIG. 1D.

Figure 5A:
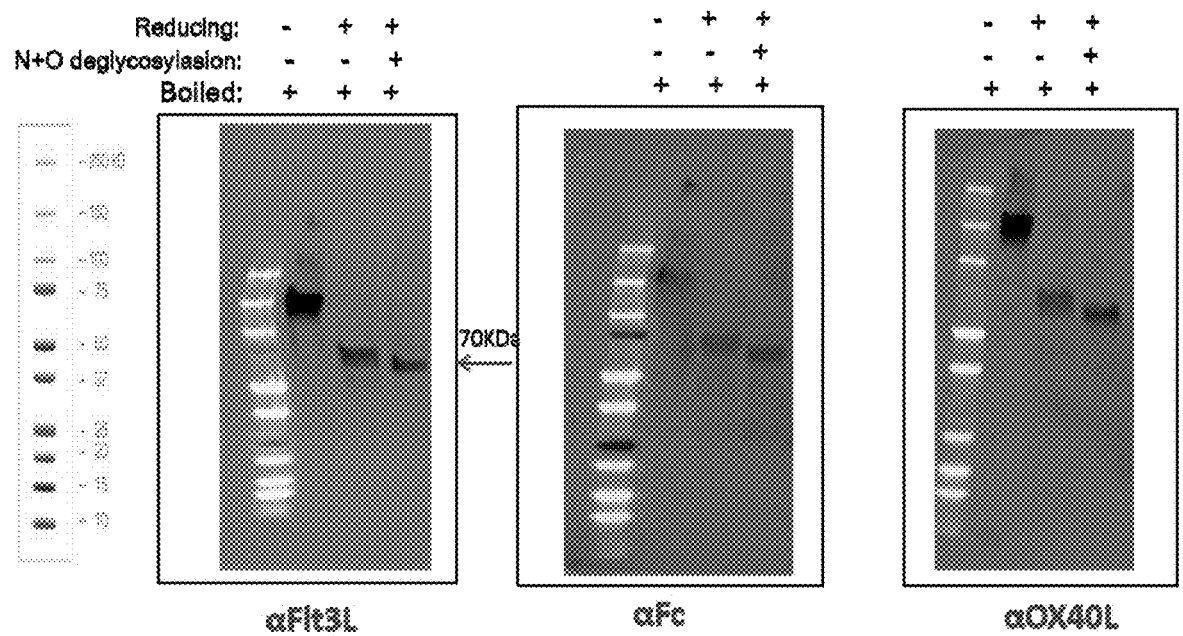
FIG. 5A shows characterization of a murine FLT3L-Fc-OX40L chimeric protein by Western blot demonstrating the chimeric proteins native state and tendency to form a multimer. Untreated samples (i.e., without reducing agent or deglycosylation agent) of the FLT3L-Fc-OX40L chimeric protein, e.g., control, were loaded into lane 2 in all the blots. Samples in lane 3 were treated with the reducing agent, β-mercaptoethanol. Samples in lane 4 were treated with a deglycosylation agent and the reducing agent. Each individual domain of the chimeric protein was probed using an anti-FLT3L, anti-Fc, or anti-OX40L antibody, respectively.

The mFLT3L-Fc-OX40L construct was transiently expressed in 293 cells and purified using protein-A affinity chromatography. Western blot analyses were performed to validate the detection and binding of all three components of mFLT3L-Fc-OX40L with their respective binding partners (FIG. 5A). The Western blots indicated the presence of a dominant multimeric band in the non-reduced lanes (FIG. 5A, lane 2 in each blot), which was reduced to a glycosylated monomeric band in the presence of the reducing agent, β-mercaptoethanol (FIG. 5A, lane 3 in each blot). As shown in FIG. 5A, lane 4 in each blot, the chimeric protein ran as a monomer at the predicted molecular weight of about 70 kDa in the presence of both a reducing agent (β-mercaptoethanol) and an deglycosylation agent.

Figure 5B:
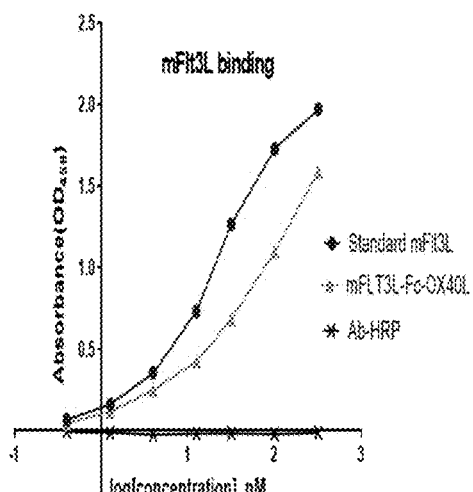
FIG. 5B to FIG. 5D show ELISA data demonstrating the binding affinity of mFLT3L domain of mFLT3L-Fc-OX40L (FIG. 5B), the of mFc domain (FIG. 5C), and of the mOX40L domain (FIG. 5D) for their respective binding partners.
Figure 5C:
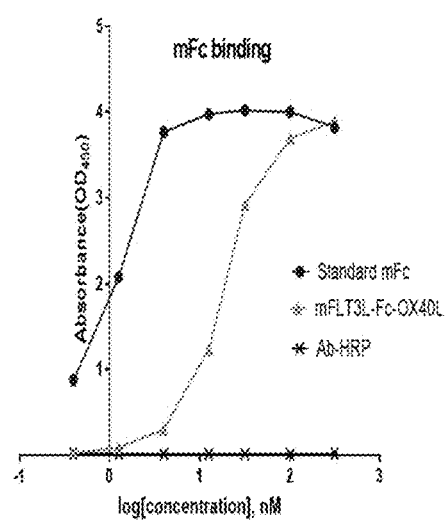
Figure 5D:
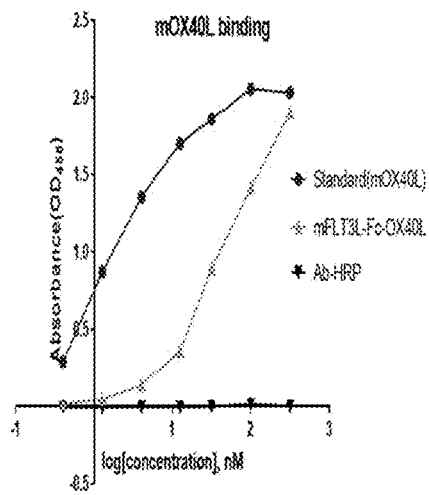

Functional ELISA were performed to demonstrate the binding affinity of the different domains of the mFLT3L-Fc-OX40L chimeric protein to their respective binding partners. As shown in FIG. 5B, binding of the mFLT3L domain of the mFLT3L-Fc-OX40L chimeric protein was characterized by capturing to a plate-bound recombinant mouse mFLT3 protein and detecting via an anti-mFLT3L antibody and HRP staining. Recombinant mFLT3L protein was used to generate a standard curve. The data shown in FIG. 5B demonstrates that the mFLT3L domain of the mFLT3L-Fc-OX40L chimeric protein effectively interacted with its binding partner in a concentration-dependent manner and with high affinity. As shown in FIG. 5C, binding of the mFc portion of the mFLT3L-Fc-OX40L chimeric protein was characterized by capturing the chimeric protein to a plate-bound mouse IgG Fc gamma antibody and detecting via an HRP conjugated anti-mouse Fc antibody. A mouse whole IgG was used to generate a standard curve. As shown in FIG. 5D, binding of the mOX40L domain of the mFLT3L-Fc-OX40L chimeric protein was characterized by capturing to a plate-bound recombinant mouse mOX40 protein and detecting via an anti-mOX40L antibody and HRP staining. Recombinant mOX40L protein was used to generate a standard curve. The data shown in FIG. 5D demonstrates that the mOX40L domain of the mFLT3L-Fc-OX40L chimeric protein effectively interacted with its binding partner in a concentration-dependent manner and with high affinity.

Example 4. Construction and Characterization of an Illustrative FLT3L- and GITRL-Based Chimeric Protein A construct encoding a murine FLT3L- and GITRL-based chimeric protein was generated. The "mFLT3L-Fc-GITRL" construct included a murine extracellular domain (ECD) of FLT3L fused to a murine ECD of GITRL via a hinge-CH2-CH3 Fc domain derived from IgG1. See, FIG. 1D.

Figure 6A:
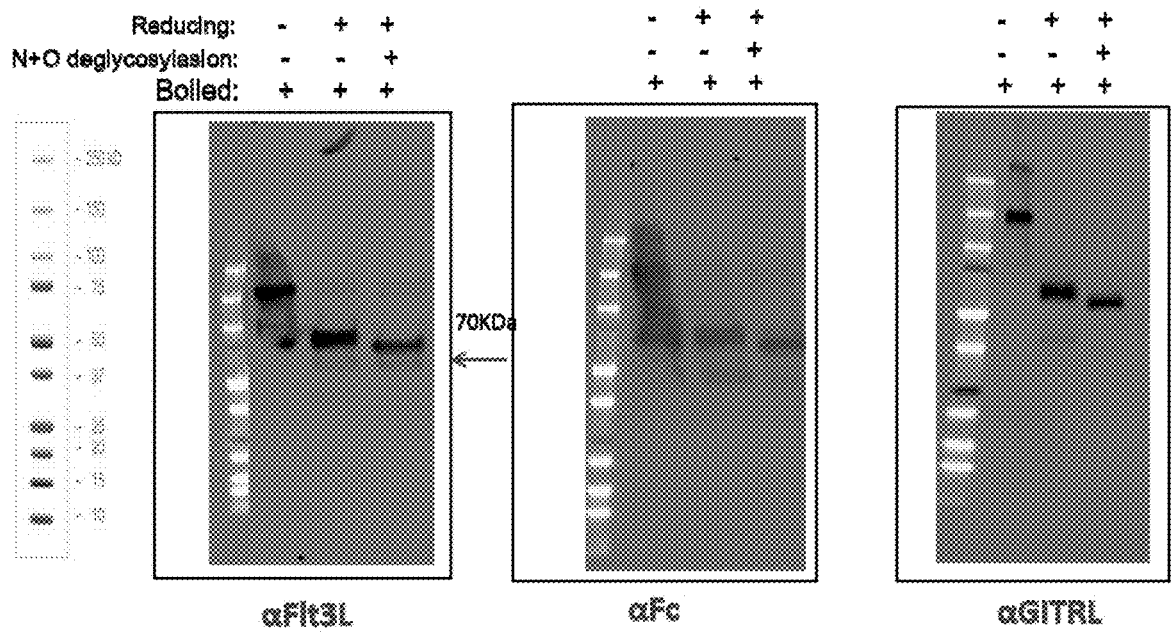
FIG. 6A shows characterization of a murine FLT3L-Fc-GITRL chimeric protein by Western blot demonstrating the chimeric proteins native state and tendency to form a multimer. Untreated samples (i.e., without reducing agent or deglycosylation agent) of the FLT3L-Fc-GITRL chimeric protein, e.g., control, were loaded into lane 2 in all the blots. Samples in lane 3 were treated with the reducing agent, β-mercaptoethanol. Samples in lane 4 were treated with a deglycosylation agent and the reducing agent. Each individual domain of the chimeric protein was probed using an anti-FLT3L, anti-Fc, or anti-GITRL antibody, respectively.

The mFLT3L-Fc-GITRL construct was transiently expressed in 293 cells and purified using protein-A affinity chromatography. Western blot analyses were performed to validate the detection and binding of all three components of mFLT3L-Fc-GITRL with their respective binding partners (FIG. 6A). The Western blots indicated the presence of a dominant multimeric band in the non-reduced lanes (FIG. 6A, lane 2 in each blot), which was reduced to a glycosylated monomeric band in the presence of the reducing agent, β-mercaptoethanol (FIG. 6A, lane 3 in each blot). As shown in FIG. 6A, lane 4 in each blot, the chimeric protein ran as a monomer at the predicted molecular weight of about 70 kDa in the presence of both a reducing agent (β-mercaptoethanol) and an deglycosylation agent.

Figure 6B:
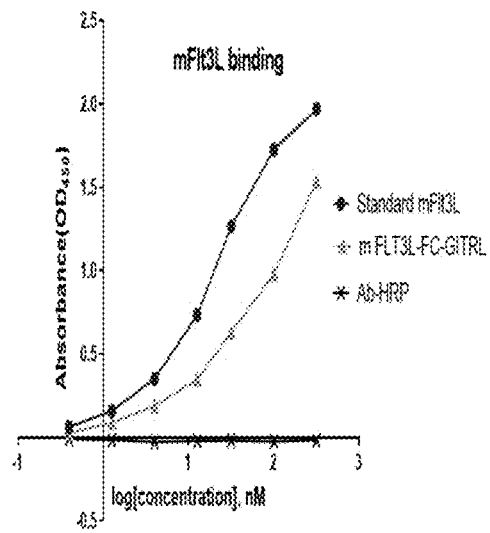
FIG. 6B to FIG. 6D show ELISA data demonstrating the binding affinity of mFLT3L domain of mFLT3L-Fc-GITRL (FIG. 6B), the of mFc domain (FIG. 6C), and of the mGITRL domain (FIG. 6D) for their respective binding partners.
Figure 6C:
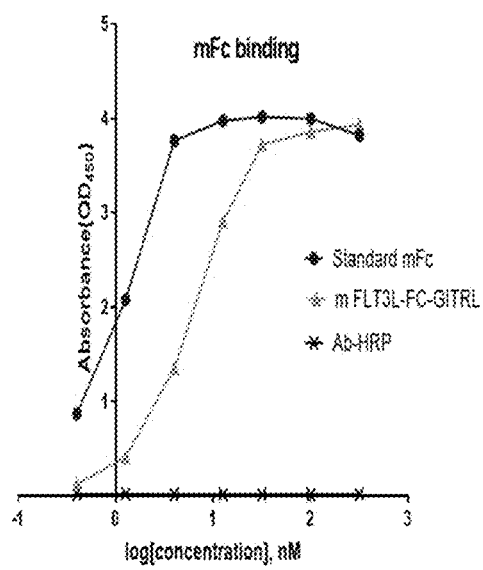
Figure 6D:
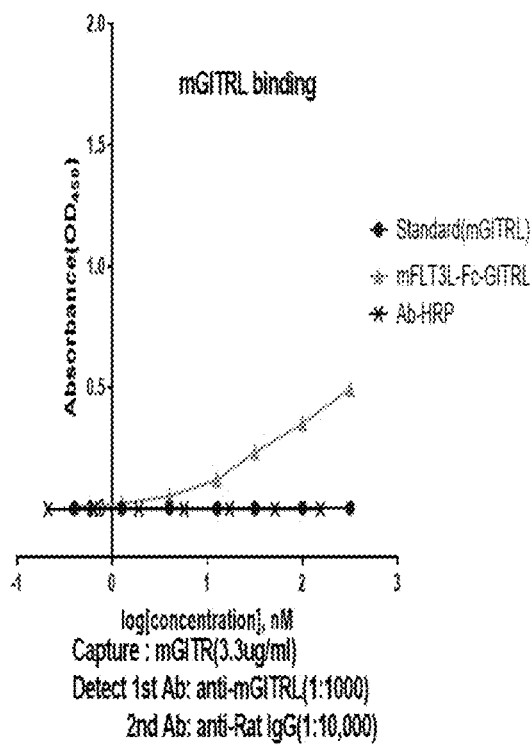
Figure 7A:
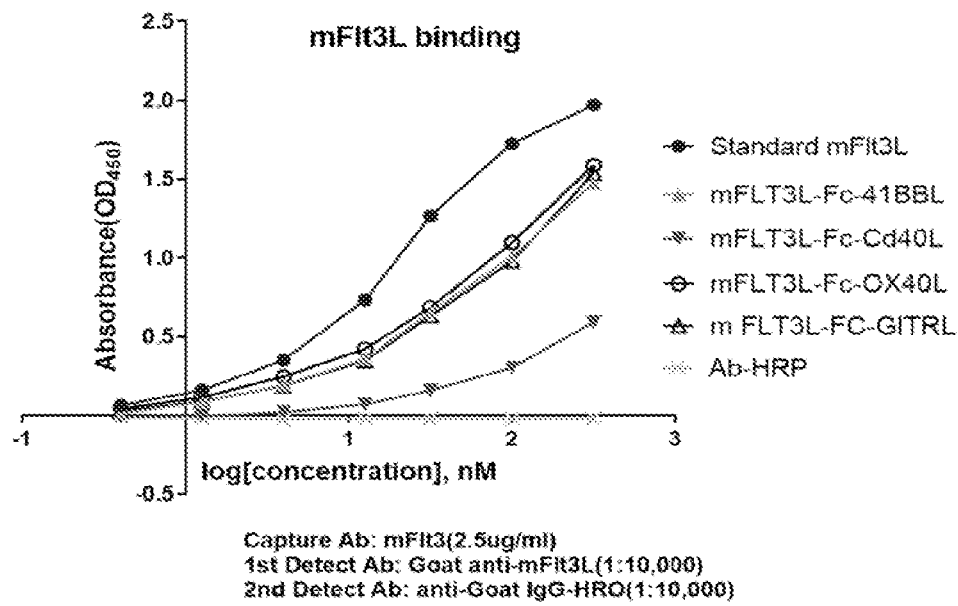
FIG. 7A compiles the mFLT3L domain ELISA assay data from FIG. 3B, FIG. 4B, FIG. 5B, and FIG. 6B.
Figure 7B:
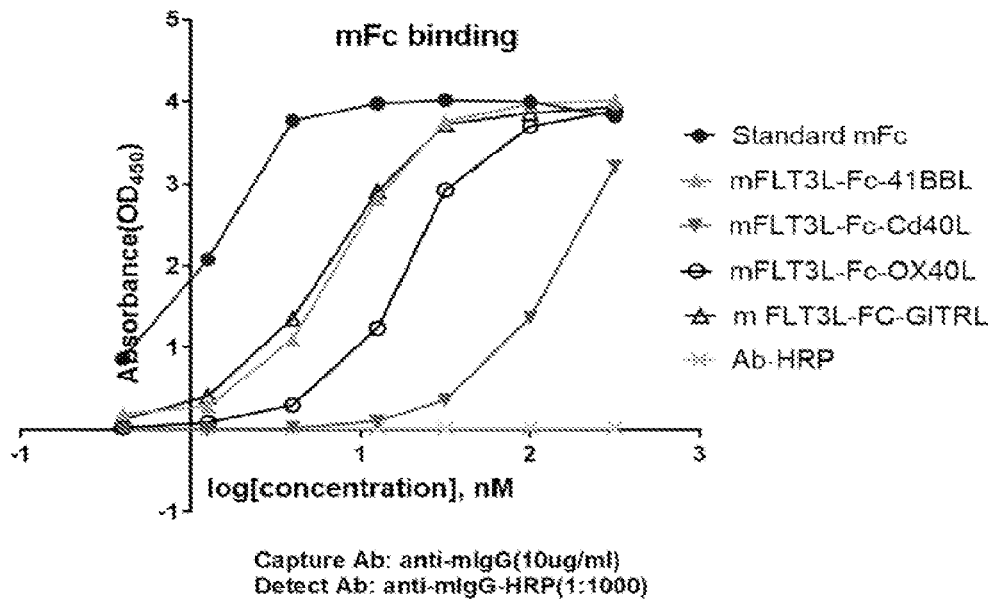
FIG. 7B compiles the mFc domain ELISA data from FIG. 3C, FIG. 4C, FIG. 5C, and FIG. 6C.

Functional ELISA were performed to demonstrate the binding affinity of the different domains of the mFLT3L-Fc-GITRL chimeric protein to their respective binding partners. As shown in FIG. 6B, binding of the mFLT3L domain of the mFLT3L-Fc-GITRL chimeric protein was characterized by capturing to a plate-bound recombinant mouse mFLT3 protein and detecting via an anti-mFLT3L antibody and HRP staining. Recombinant mFLT3L protein was used to generate a standard curve. The data shown in FIG. 6B demonstrates that the mFLT3L domain of the mFLT3L-Fc-GITRL chimeric protein effectively interacted with its binding partner in a concentration-dependent manner and with high affinity. As shown in FIG. 6C, binding of the mFc portion of the mFLT3L-Fc-GITRL chimeric protein was characterized by capturing the chimeric protein to a plate-bound mouse IgG Fc gamma antibody and detecting via an HRP conjugated anti-mouse Fc antibody. A mouse whole IgG was used to generate a standard curve. As shown in FIG. 6D, binding of the mGITRL domain of the mFLT3L-Fc-GITRL chimeric protein was characterized by capturing to a plate-bound recombinant mouse mGITR protein and detecting via an anti-mGITRL antibody and HRP staining. Recombinant mGITRL protein was used to generate a standard curve. The data shown in FIG. 6D demonstrates that the mGITRL domain of the mFLT3L-Fc-GITRL chimeric protein effectively interacted with its binding partner in a concentration-dependent manner and with high affinity.

Example 5: Dual ELISA Characterization

Figure 8:
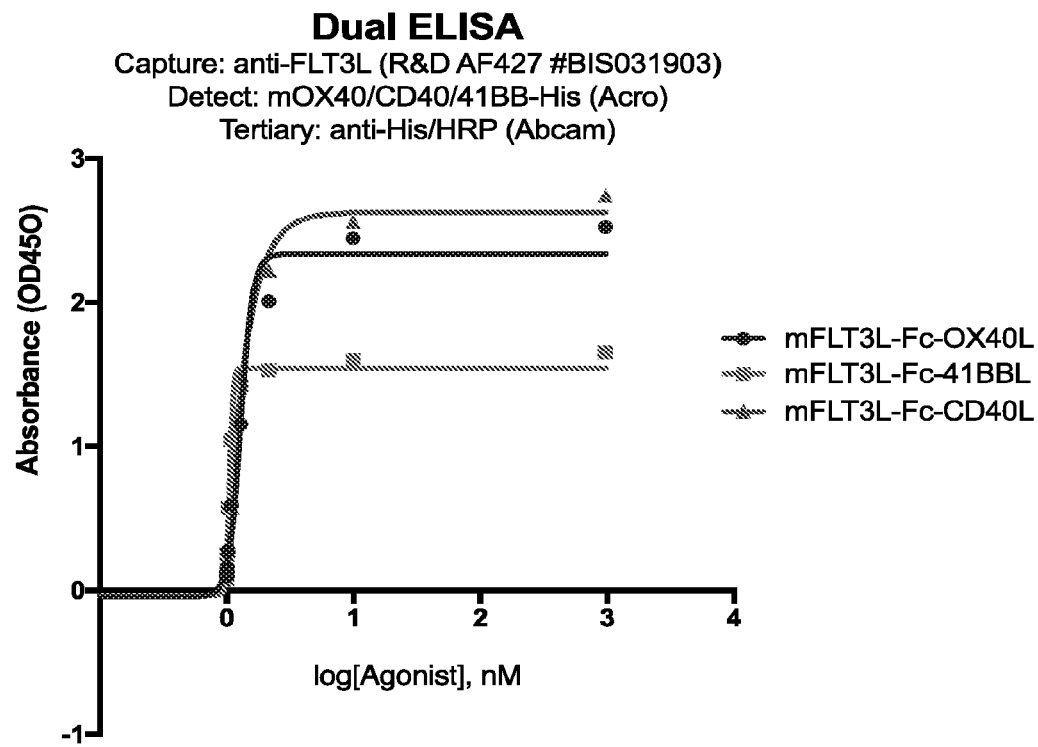
FIG. 8 shows dual ELISA data of mFLT3L-Fc-OX40L, mFLT3L-Fc-4-1BBL, and FLT3L-Fc-CD40L.

FIG. 8 shows dual ELISA assays of mFLT3L-Fc-OX40L, mFLT3L-Fc-4-1BBL, and FLT3L-Fc-CD40L chimeric proteins. Capture was performed with an anti-FLT3L antibody, followed by detection of the co-stimulatory domain with a his-tagged recombinant protein, and visualized using an anti-his/HRP antibody.

Example 6: Characterization of the FLT3L-Fc-CD40L Chimeric Protein

The FLT3L-Fc-CD40L chimeric protein was further characterized.

Figure 9A:
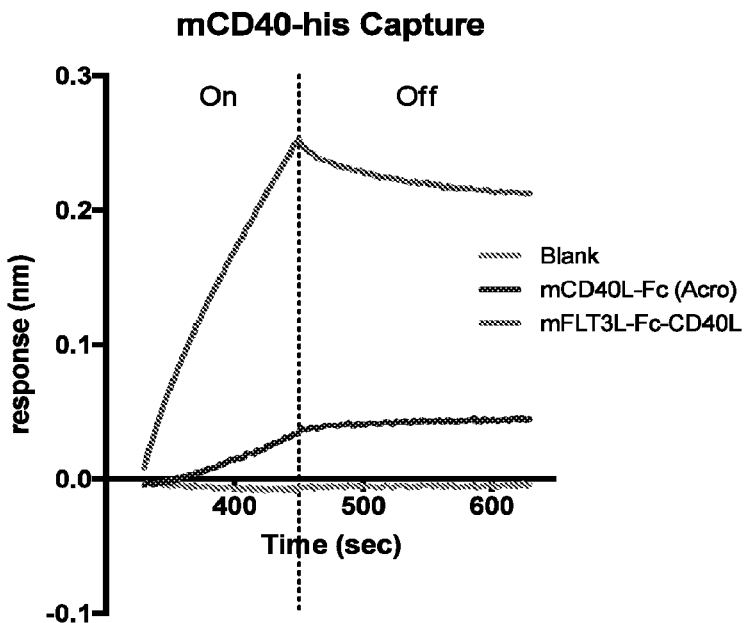
FIG. 9A to FIG. 9E shows characterization of the mFLT3L-Fc-CD40L chimeric protein.
Figures 9B, 9C:
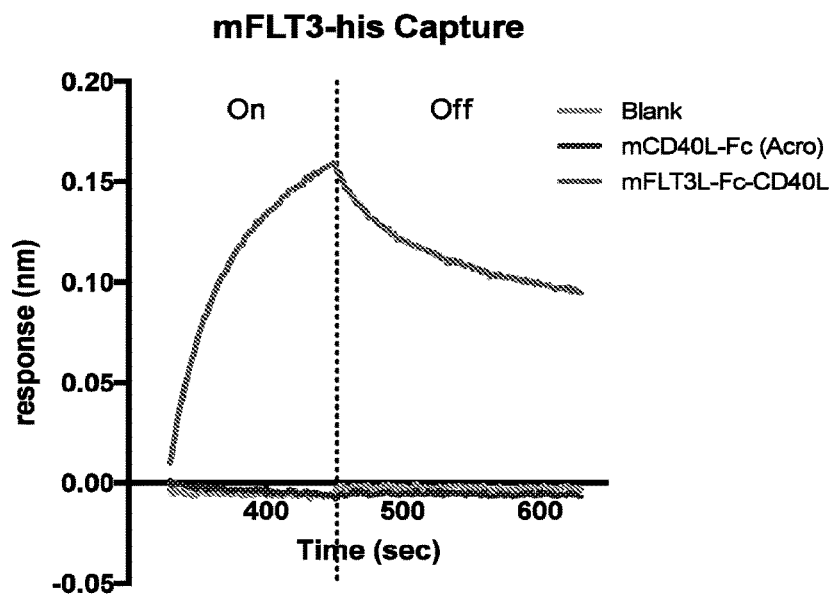

FIG. 9A shows results from the Octet system for measuring affinity of the FLT3L-Fc-CD40L chimeric protein with mCD40-his capture. FIG. 9B shows results from the Octet system for measuring affinity of the FLT3L-Fc-CD40L chimeric protein with mFLT3-his capture. Octet was used to determine on-/off-rates and binding affinities to the target receptors. FIG. 9C shows a summary of the data of FIG. 9A and FIG. 9B.

Figure 9D:
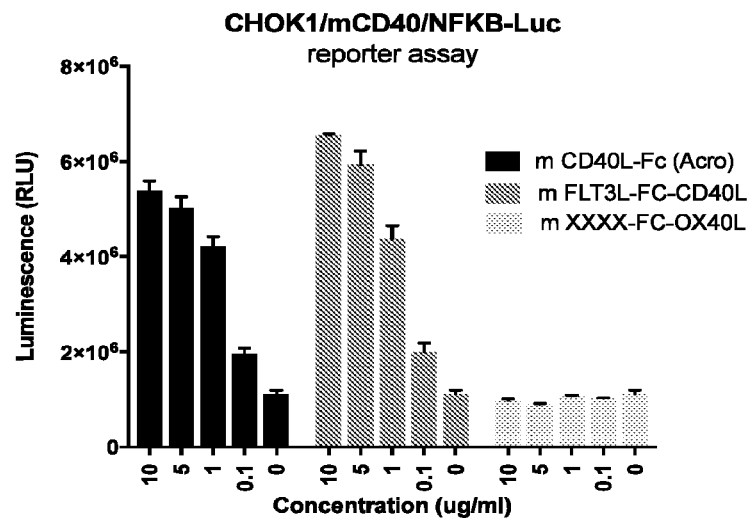

FIG. 9D shows results of an NFkB-mCD40 luciferase reporter assay. NFkB-mCD40 reporter cell lines were generated by stably transfecting CHO-K1 cells with both a mouse CD40-expressing vector and an NFkB-luciferase reporter vector (Promega). Cells were incubated with a dose titration of commercially available mCD40L-Fc (Acro Biosystems), the mFLT3-Fc-CD40L chimeric protein, or a non-CD40L containing chimeric protein ("mXXXX-Fc-OX40L") as a negative control. After 6 hours, luminescence was quantitated on a luminometer.

Figure 9E:
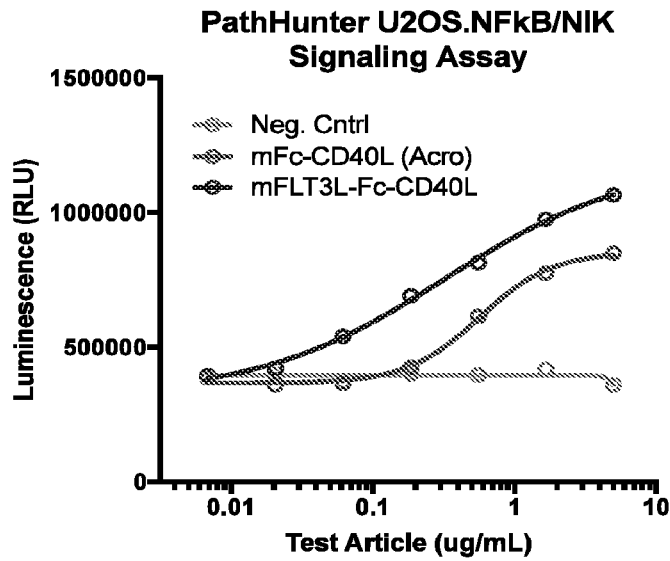

FIG. 9E shows a PathHunter U2OS cell-based assay for CD40L signaling (NFkB activity, non-canonical). PathHunter U2OS cells (DiscoverX) are responsive to both mouse and human signaling through CD40; and are another means to inform on NFkB activity (non-canonical). Cells were incubated with either commercial mCD40L-Fc (Acro Biosystems) or the mFLT3L-Fc-CD40L chimeric protein. After 6 hours, luciferase activity was measured on a luminometer.

FIG. 9D and FIG. 9E surprisingly demonstrate that the creation of the chimeric protein is accomplished without loss of activity on the CD40L side and, indeed, with a slight increase in activity relative to a single-sided CD40L molecule.

Figure 9F:
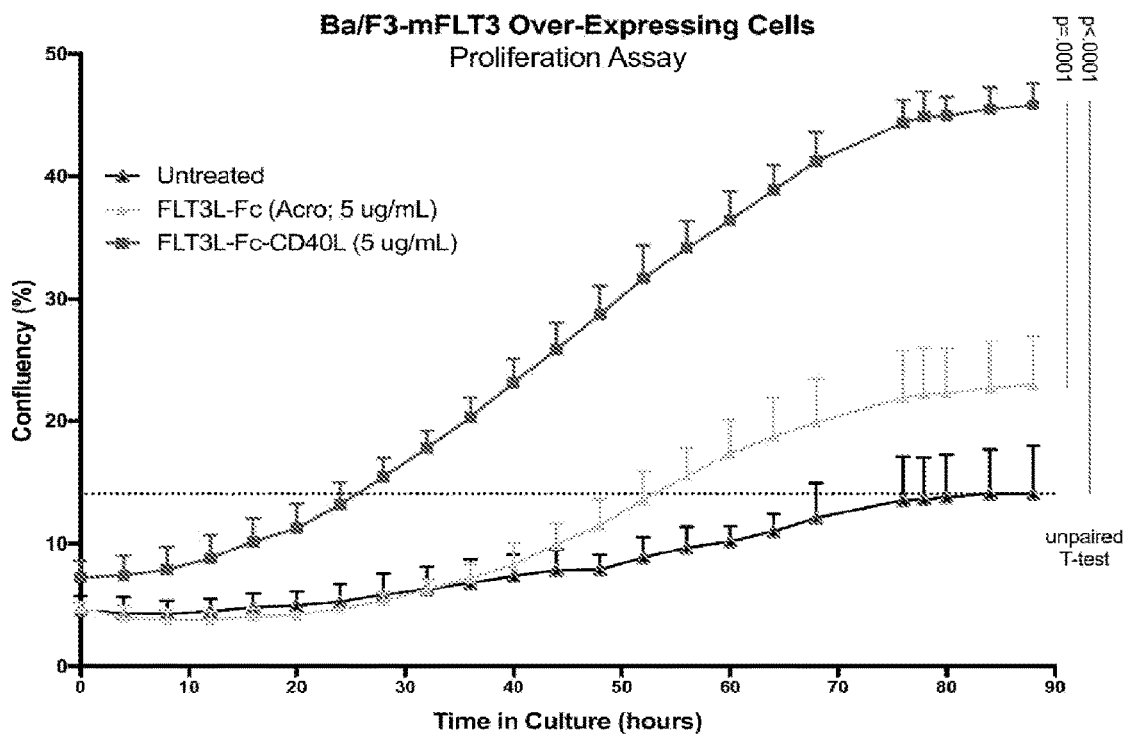
FIG. 9F shows proliferation of a model cells system (mFLT3 over-expressing Ba/F3 cells) in response to Flt3 signaling. The dotted line indicates the maximum proliferation of the untreated cells. Significance was determined using one-way unpaired T-test.

FIG. 9F shows proliferation of a model cell system (mFLT3 over-expressing Ba/F3 cells) in response to Flt3 signaling. The dotted line indicates the maximum proliferation of the untreated cells. Significance was determined using unpaired T-test. The IL-3 dependent proB cell line, Ba/F3, is responsive to FLT3L signaling when it over-expresses the FLT3 receptor. mFLT3 over-expressing Ba/F3 cells were incubated with a dose titration of commercially available FLT3L-Fc (Acro Biosystems) or 4 different FLT3L-based chimeric proteins. Proliferation was assessed using the Incucyte live-cell imaging platform; measuring confluency over time.

FIG. 9F surprisingly demonstrates that the creation of the chimeric protein is accomplished without loss of activity on the FLT3 side and, indeed, with a significant increase in activity relative to a single-sided FLT3 molecule.

Figure 10A:
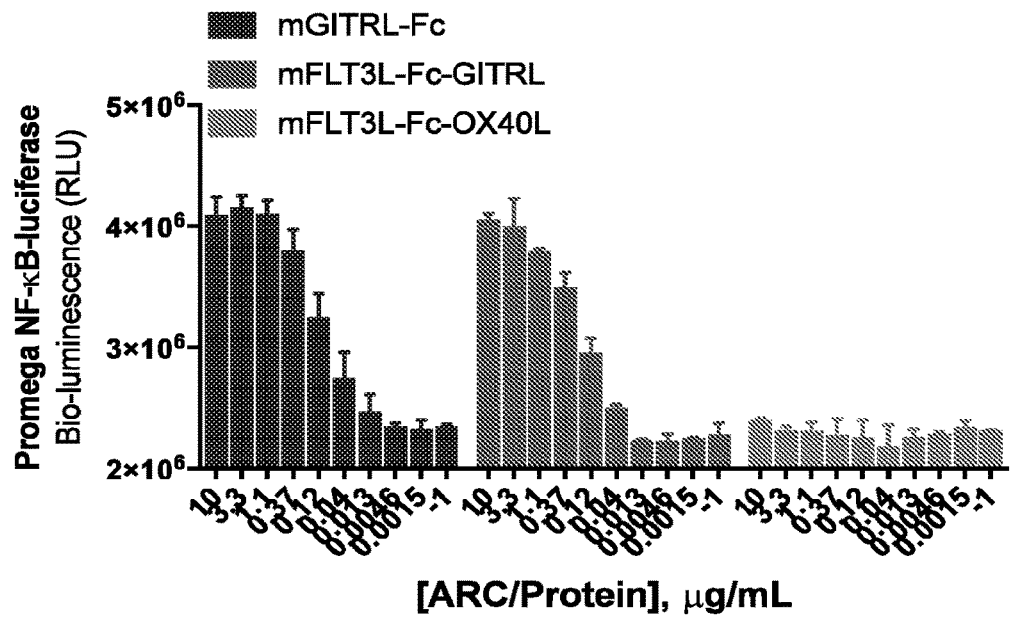
FIG. 10A shows characterization of FLT3L-Fc-GITRL activity with an NFkB-mGITR reporter cell line generated by stably transfecting CHO-K1 cells with both a mouse GITR expressing vector and NFkB-luciferase reporter vector (the left bars are mGITRL-Fc, the center bars are mFLT3-Fc-GITRL, and the right bars are mFLT3-Fc-OX40L).

Example 7: Characterization of the FLT3L-Fc-GITRL, FLT3L-Fc-OX40L, and FLT3L-Fc-4-1 BBL Chimeric Proteins FIG. 10A shows characterization of FLT3L-Fc-GITRL activity with an NFkB-mGITR reporter cell line generated by stably transfecting CHO-K1 cells with both a mouse GITR-expressing vector and NFkB-luciferase reporter vector. NFkB-mGITR reporter cell lines were generated by stably transfecting CHO-K1 cells with both a mouse GITR-expressing vector and Promega's NFkB-luciferase reporter vector. Cells were incubated with a dose titration of commercially available mGITRL-Fc (Acro Biosystems), the mFLT3-Fc-GITRL chimeric protein, or a non-GITRL containing chimeric protein (mFLT3L-Fc-OX40L) as a negative control. After 6 hours, luminescence was quantitated on a luminometer.

FIG. 10A surprisingly demonstrates that the creation of the chimeric protein is accomplished without loss of activity on the GITRL side.

Figure 10B:
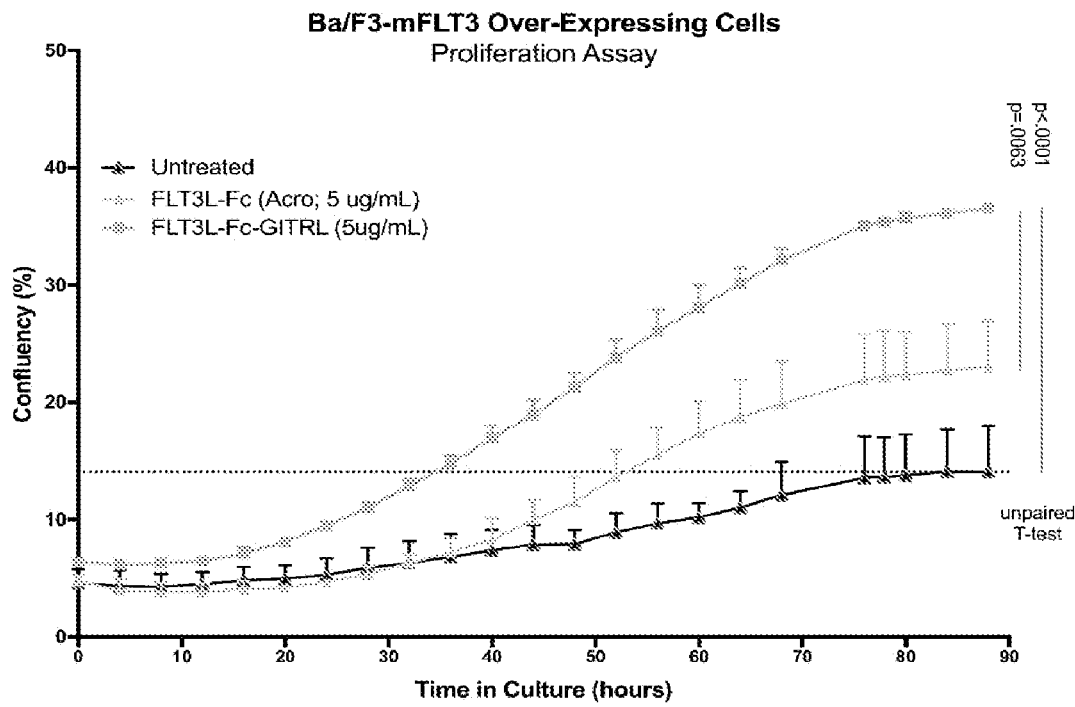
FIG. 10B shows proliferation of a model cells system (mFLT3 over-expressing Ba/F3 cells) in response to Flt3 signaling via FLT3L-Fc-GITRL. The dotted line indicates the maximum proliferation of the untreated cells and significance was determined using one-way unpaired T-test.
Figure 10C:
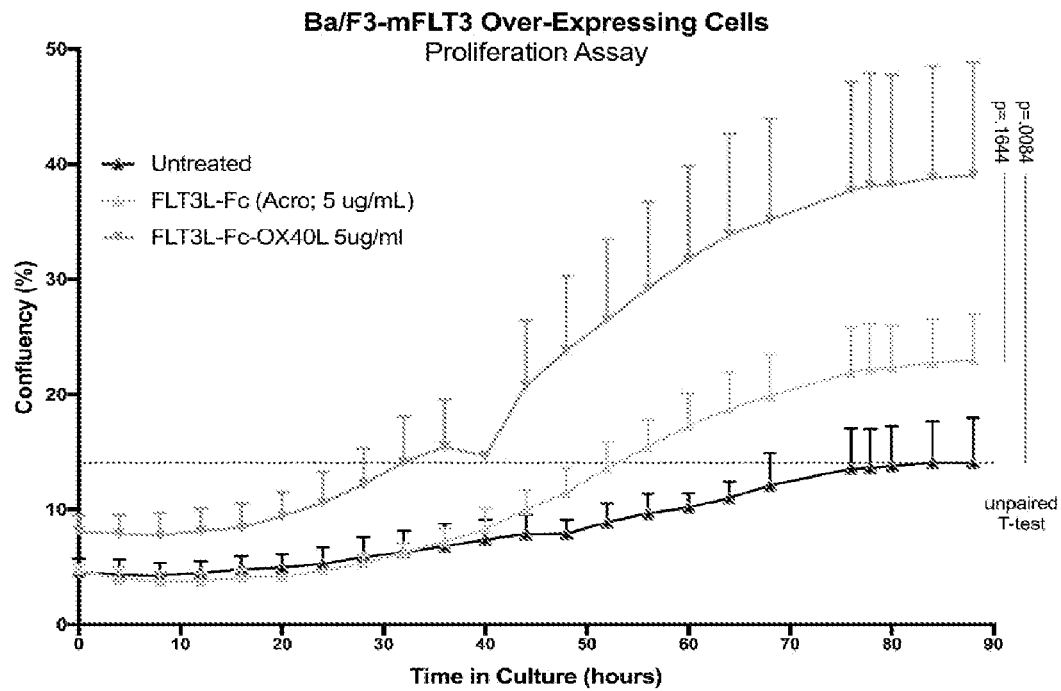
FIG. 10C shows proliferation of a model cells system (mFLT3 over-expressing Ba/F3 cells) in response to Flt3 signaling via FLT3L-Fc-OX40L. The dotted line indicates the maximum proliferation of the untreated cells and significance was determined using one-way unpaired T-test.
Figure 10D:
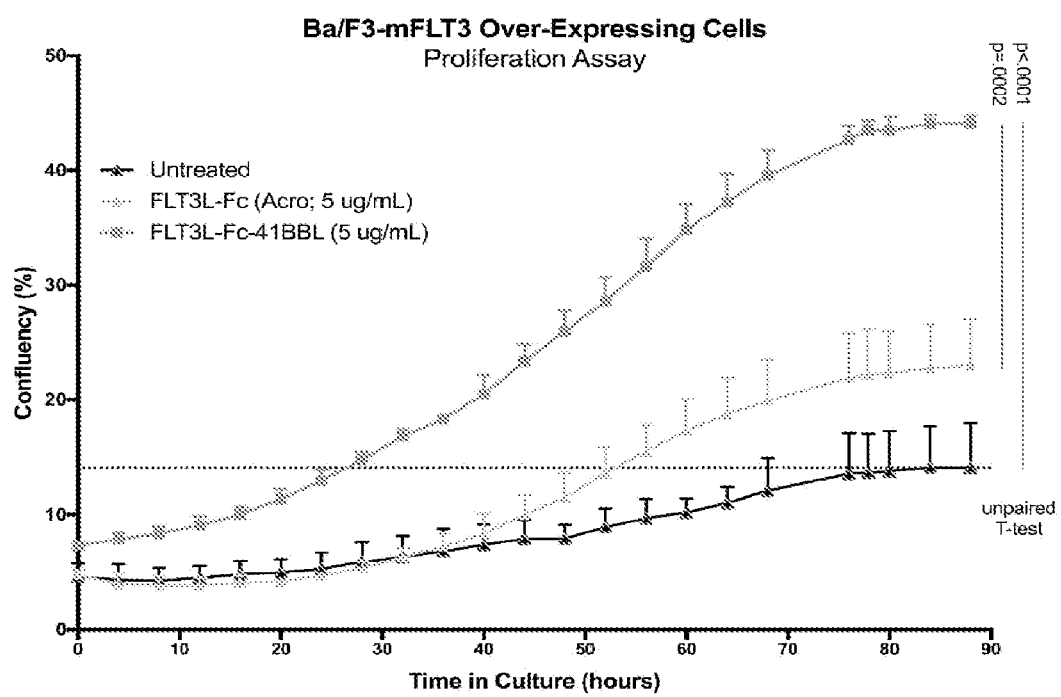
FIG. 10D shows proliferation of a model cells system (mFLT3 over-expressing Ba/F3 cells) in response to Flt3 signaling via FLT3L-Fc-4-1BBL. The dotted line indicates the maximum proliferation of the untreated cells and significance was determined using one-way unpaired T-test.

The Ba/F3 assay described above was employed to measure proliferation of other chimeric proteins. FIG. 10B shows proliferation of a model cells system (mFLT3 over-expressing Ba/F3 cells) in response to Flt3 signaling via FLT3L-Fc-GITRL. FIG. 10C shows proliferation of a model cells system (mFLT3 over-expressing Ba/F3 cells) in response to Flt3 signaling via FLT3L-Fc-OX40L. FIG. 10D shows proliferation of a model cells system (mFLT3 over-expressing Ba/F3 cells) in response to Flt3 signaling via FLT3L-Fc-4-1BBL. For all of FIGS. 10B-D, the dotted line indicates the maximum proliferation of the untreated cells and significance was determined using one-way unpaired T-test.

FIG. 10B to FIG. 10D surprisingly demonstrate that the creation of the chimeric proteins is accomplished without loss of activity on the FLT3 side and, indeed, with an increase in activity relative to a single-sided FLT3 molecule.

Example 8: In Vivo Characterization of Chimeric Protein Signaling

Mice were given 9 or 11 consecutive injections (IP) of the murine FLT3L chimeric proteins, diluted in 0.01% mouse serum albumin (MSA; also used as the vehicle control). Mice were euthanized on day 10 or on 12. Serum was collected for cytokine analysis, and spleens and mesenteric lymph nodes (MLN) were isolated. Spleen weights and total lymph node cell counts were recorded. Cell populations of dendritic cells (CD11c+) and activated dendritic cells (CD11c+/CD103+ and CD11c+/MHCII+(IA/IE)) were analyzed by flow cytometry. Serum cytokines were assessed using a Procarta multiplex kit, which was analyzed on the Luminex platform.

Figure 11:
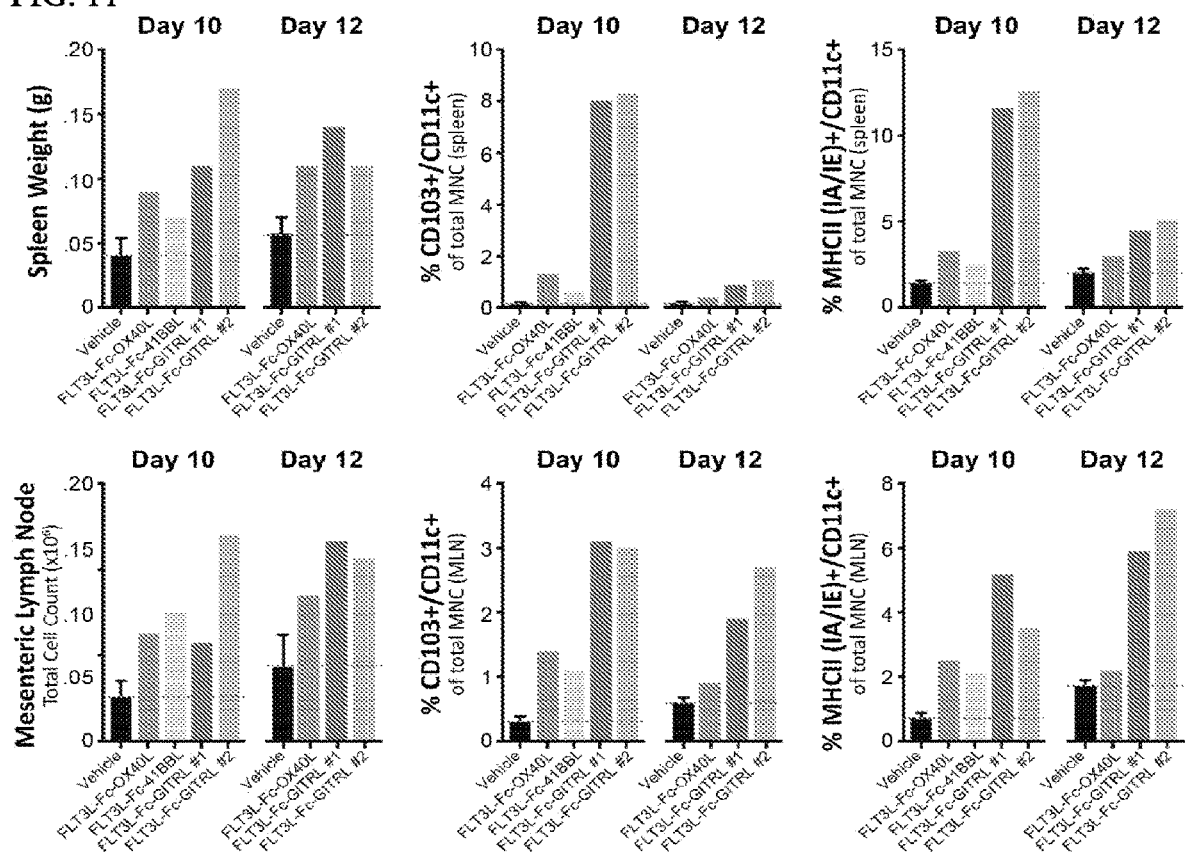
FIG. 11 shows in vivo dendritic cell activation by various FLT3L-based chimeric proteins.

FIG. 11 shows in vivo dendritic cell activation by various FLT3L-based chimeric proteins.

Figure 12A:
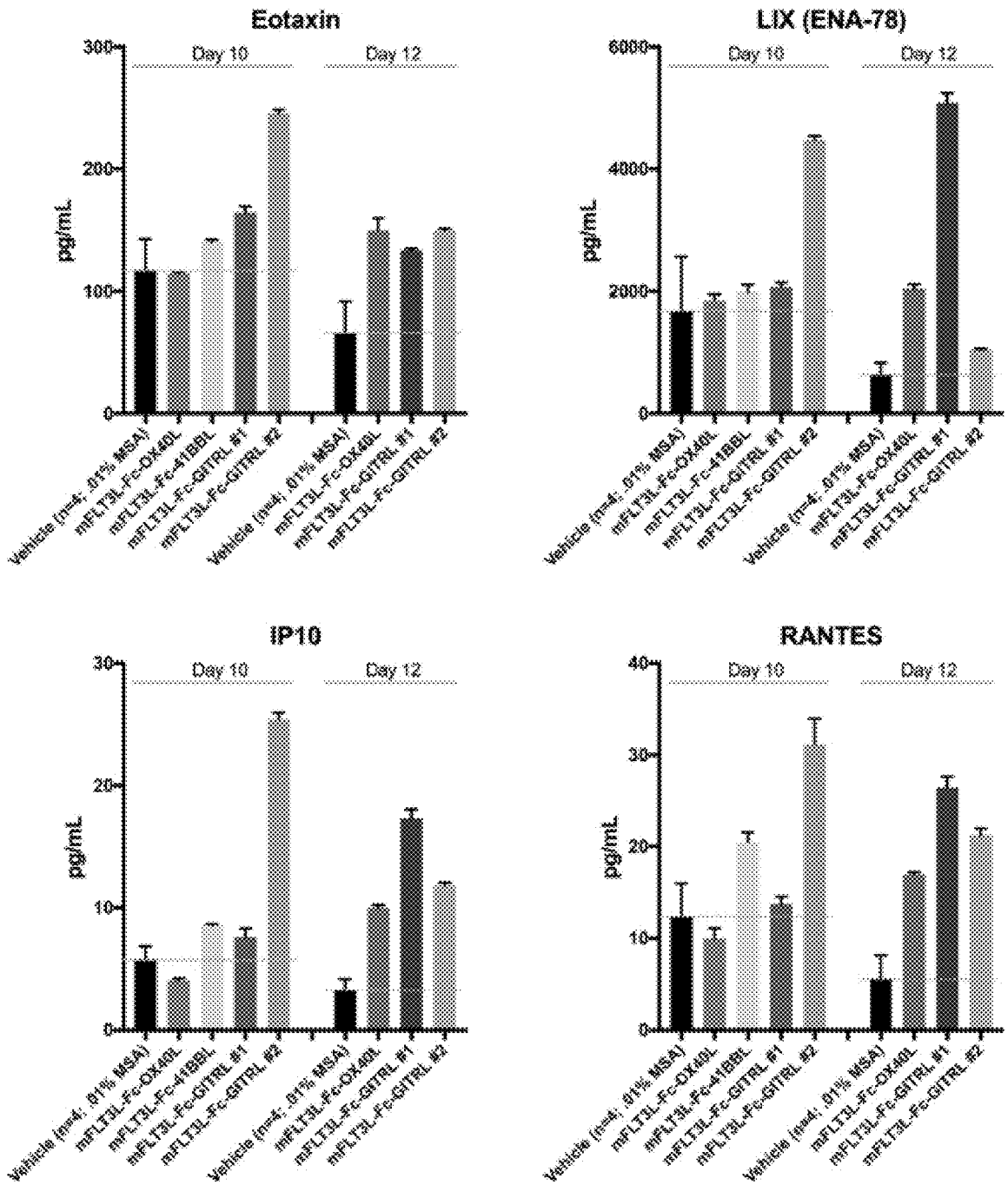
FIG. 12A shows in vivo serum cytokines by various FLT3L-based chimeric proteins. Mice were injected for 9 or 11 consecutive days, and then mesenteric lymph nodes (MLN)/Spleens were isolated on day 10 or 12 and analyzed by flow cytometry.

FIG. 12A shows in vivo serum cytokines by various FLT3L-based chimeric proteins. Mice were injected for 9 or 11 consecutive days, and then MLN/Spleens were isolated on day 10 or 12 and analyzed by flow cytometry.

Figure 12B:
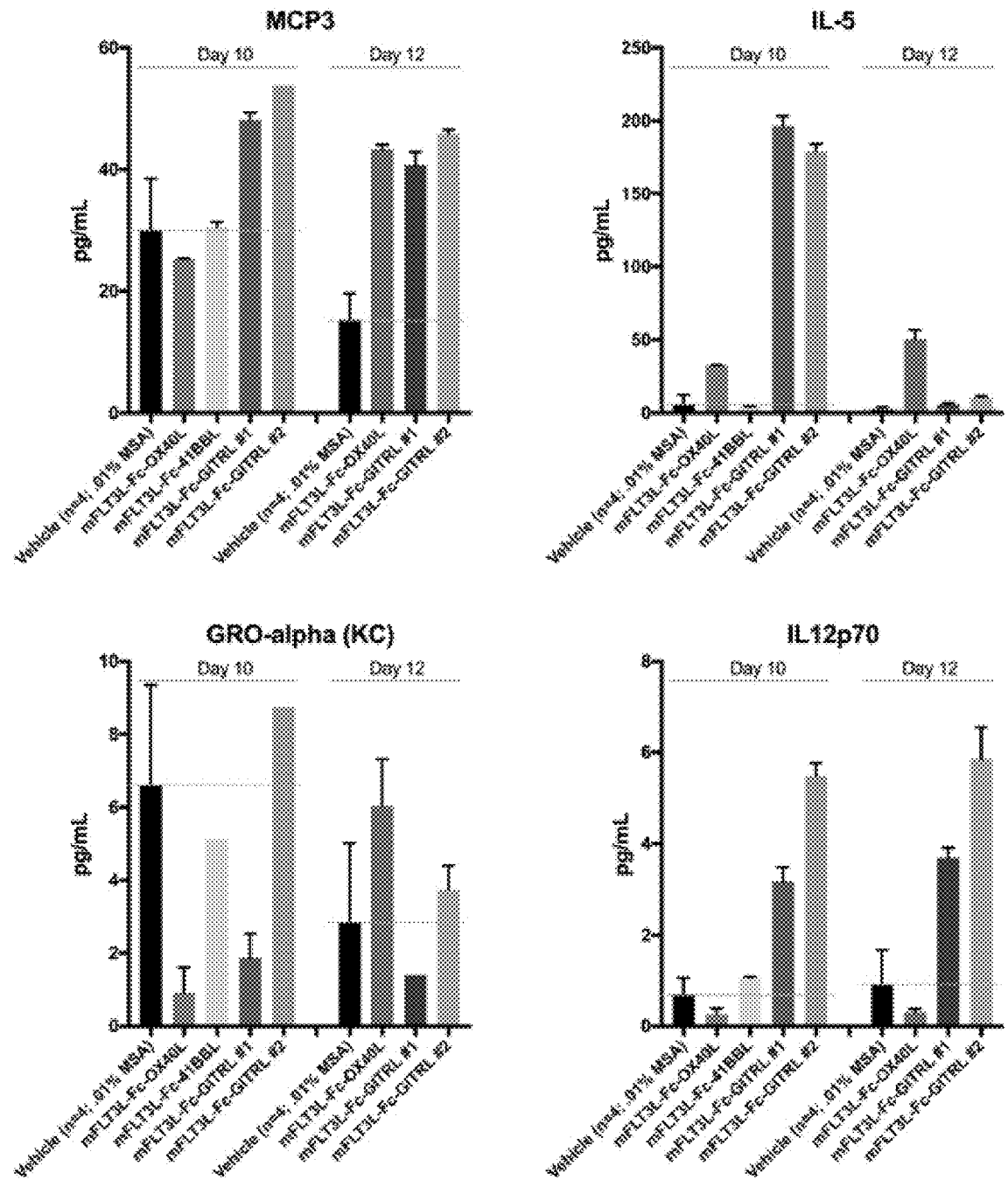
FIG. 12B shows in vivo serum cytokines by various FLT3L-based chimeric proteins. Mice were injected for 9 or 11 consecutive days, and then MLN/Spleens were isolated on day 10 or 12 and analyzed by flow cytometry.

FIG. 12B shows in vivo serum cytokines by various FLT3L-based chimeric proteins. Mice were injected for 9 or 11 consecutive days, and then MLN/Spleens were isolated on day 10 or 12 and analyzed by flow cytometry.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

EQUIVALENTS

While the invention has been disclosed in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments disclosed specifically herein. Such equivalents are intended to be encompassed in the scope of the following claims.

What is claimed is:

1. A chimeric protein of a general structure of:
N terminus-(a)-(b)-(c)-C terminus,
wherein:
(a) is a first domain comprising the extracellular domain of FMS like tyrosine kinase 3 ligand (FLT3L),
(b) is a linker adjoining the first domain and a second domain, and
(c) is the second domain comprising the extracellular domain of 4-1 BB ligand (4-1 BBL).

2. The chimeric protein of claim 1, wherein the linker comprises a Fc domain derived from IgG1 or IgG4.

3. The chimeric protein of claim 1, wherein the linker further comprises one or more joining linkers independently selected from SEQ ID NOs: 4-50.

* * * * *